US007507411B2

(12) United States Patent
Zhou et al.

(10) Patent No.: US 7,507,411 B2
(45) Date of Patent: Mar. 24, 2009

(54) ATTENUATED INFLUENZA NS1 VARIANTS

(75) Inventors: Yan Zhou, Saskatoon (CA);
Yeun-Kyung Shin, Seoul (KR); Lorne A. Babiuk, Edmonton (CA); Qiang Liu, Saskatoon (CA)

(73) Assignee: University of Saskatchewan, Saskatoon, Saskatchewan (CA)

( * ) Notice: Subject to any disclaimer, the term of this patent is extended or adjusted under 35 U.S.C. 154(b) by 0 days.

(21) Appl. No.: 11/811,642

(22) Filed: Jun. 11, 2007

(65) Prior Publication Data
US 2008/0050402 A1 Feb. 28, 2008

Related U.S. Application Data

(60) Provisional application No. 60/816,208, filed on Jun. 23, 2006.

(51) Int. Cl.
*A61K 39/12* (2006.01)
*A61K 39/145* (2006.01)
*C12P 21/04* (2006.01)
*C12P 19/34* (2006.01)

(52) U.S. Cl. .................. 424/186.1; 435/91.1; 435/71.1; 435/70.1; 424/206.1; 424/209.1; 424/205.1

(58) Field of Classification Search ....................... None
See application file for complete search history.

(56) References Cited

U.S. PATENT DOCUMENTS

| 5,578,473 | A | 11/1996 | Palese et al. |
| 6,951,754 | B2 | 10/2005 | Hoffmann |
| 6,974,686 | B2 | 12/2005 | Parkin |
| 7,037,707 | B2 | 5/2006 | Webster et al. |
| 2004/0029251 | A1 | 2/2004 | Hoffmann et al. |

OTHER PUBLICATIONS

Neumann et al., A decade after the generation of a negative-sense RNA virus from cloned cDNA—what have we learned?, 2002, Journal of General Virology, vol. 83, pp. 2635-2662.*
Shin et al., SH3 Binding Motif 1 in Influenza A Virus NS1 Protein Is Essential for PI3K/Akt Signaling Pathway Activation, 2007, Journal of Virology, vol. 81, No. 23, pp. 12730-12739.*
Orkin, Report and Recommendations of the Panel to Assess the NIH Investment in Research on Gene Therapy, 1995, NIH News, pp. 1-37.*
Verma et al., Gene therapy—promises, problems and prospects, 1997, Nature, vol. 389, pp. 239-242.*
Pleiman et al., Activation of Phosphatidylinositol-3' Kinase by Src-Family Kinase SH3 Binding to the p85 subunit, 1994, Science, vol. 263, No. 5153, pp. 1609-1612.*
Enami, et al., "Introduction Of Site-Specific Mutations Into The Genome Of Influenza Virus," *PNAS* 87:3802-3805 (1990).
Enami, et al., "High-efficiency formation of influenza virus transfectants," *J Virol* 65:2711-2713 (1991).
Fodor, et al., "Rescue Of Influenza A Virus From Recombinant DNA," *J Virol* 73:9679-9682 (1999).
Fortes, et al., "Influenza Virus NS1 Protein Inhibits Pre-Mrna Splicing And Blocks Mrna Nucleocytoplasmic Transport," *EMBO J* 13:704-712 (1994).
Garcia-Sastre, et al., "Influenza A Virus Lacking The NS1 Gene Replicates In Interferon-Deficient Systems," *Virology* 252:324-330 (1998).
Hatada, et al., "Mutant Influenza Viruses With A Defective NS1 Protein Cannot Block The Activation Of PKR In Infected Cells," *J Virol* 73:2425-2433 (1999).
Hoffman, et al., "Eight-Plasmid System For Rapid Generation Of Influenza Virus Vaccines," *Vaccine* 20:3165-3170 (2002).
Hoffman, et al., "A DNA Transfection System For Generation Of Influenza A Virus From Eight Plasmids," *PNAS* 97:6108-6113 (2000).
Lamb, et al., "Segment 8 Of The Influenza Virus Genome Is Unique In Coding For Two Polypeptides," PNAS 76:4908-4912 (1979).
Li, et al., "The 3'-End-Processing Factor CPSF Is Required For The Splicing Of Single-Intron Pre-Mrnas In Vivo," *RNA* 7:920-931 (2001).
Lu, et al., "The Influenza Virus NS1 Protein: A Novel Inhibitor Of Pre-Mrna Splicing," *Genes Dev* 8:1817-1828 (1994).
Lu, et al., "Binding Of The Influenza Virus NS1 Protein To Double-Stranded RNA Inhibits The Activation Of The Protein Kinase That Phosphorylates The Elf-2 Translation Initiation Factor," *Virology* 214:222-228 (1995).
Luytjes, et al., "Amplification, Expression, And Packaging Of Foreign Gene By Influenza Virus," *Cell* 59:1107-1113 (1989).
Neumann, et al., "Genetic Engineering Of Influenza And Other Negative-Strand RNA Viruses Containing Segmented Genomes," *Adv Virus Res* 53:265-300 (1999).
Neumann, et al., "Generation Of Influenza A Viruses Entirely From Cloned cDNAs," *PNAS* 96:9345-9350 (1999).
Noah, et al., "Cellular Antiviral Responses Against Influenza A Virus Are Countered At The Posttranscriptional Level By The Viral NS1A Protein Via Its Binding To A Cellular Protein Required For The 3' End Processing Of Cellular Pre-mRNAS," *Virology* 307:386-395 (2003).
Palese, et al., "Negative-Strand RNA Viruses: Genetic Engineering And Applications," *PNAS* 93:11354-113548 (1996).
Qian, et al., "Two Functional Domains Of The Influenza Virus NS1 Protein Are Required For Regulation Of Nuclear Export Of mRNA," *J Virol* 68:2433-2441 (1994).
Qiu, et al., "The Influenza Virus NS1 Protein Binds To A Specific Region In Human U6 Snrna And Inhibits U6-U2 And U6-U4 Snrna Interactions During Splicing," *RNA* 1:304-316 (1995).

(Continued)

*Primary Examiner*—Bruce Campell
*Assistant Examiner*—Benjamin P Blumel
(74) *Attorney, Agent, or Firm*—Robins & Pasternak LLP

(57) ABSTRACT

Attenuated influenza virus variants comprising substitutions in NS1 that interfere with viral replication and phosphatidylinositol 3-kinase activation are described. NS1 variant polypeptides, polynucleotides encoding NS1 variant polypeptides, a reverse genetics system for producing attenuated influenza virus NS1 variants, immunogenic compositions comprising live attenuated influenza virus NS1 variants, methods of stimulating an immune response against influenza virus, methods of interfering with influenza virus replication, and methods of treating and preventing influenza virus infection are described.

7 Claims, 14 Drawing Sheets

OTHER PUBLICATIONS

Shin, et al., "Influenza A Virus NS1 Protein Activates the Phosphatidylinositol 3-Kinase (PI3K)/Akt Pathway by Direct Interaction with p85 Subunit of PI3K," *J Gen Virol* 88:13-18 (2007).

Subbarao, et al., "Rescue Of An Influenza A Virus Wild-Type PB2 Gene And A Mutant Derivative Bearing A Site-Specific Temperature-Sensitive And Attenuating Mutation," *J Virol* 67:7223-7228 (1993).

Talon, et al., "Activation Of Interferon Regulatory Factor 3 Is Inhibited By The Influenza A Virus NS1 Protein," *J Virol* 74:7989-7996 (2000).

Wang, et al., "Influenza A Virus NS1 Protein Prevents Activation Of NF-Kappab And Induction Of Alpha/Beta Interferon," *J Virol* 74:11566-11573 (2000).

\* cited by examiner

GenBank Accession No. NC_002020
H1N1 Influenza A Virus (A/Puerto Rico/8/34)
NS1 gene, NS2 gene, nonstructural protein 1, nonstructural protein 2
segment 8, complete sequence

```
H1N1 segment 8 (SEQ ID NO:1)
     1 agcaaaagca gggtgacaaa gacataatgg atccaaacac tgtgtcaagc tttcaggtag
    61 attgctttct tggcatgtc  cgcaaacgag ttgcagacca agaactaggt gatgccccat
   121 tccttgatcg gcttcgccga gatcagaaat ccctaagagg aaggggcagc actcttggtc
   181 tggacatcga gacagccaca cgtgctggaa agcagatagt ggagcggatt ctgaaagaag
   241 aatccgatga ggcacttaaa atgaccatgg cctctgtacc tgcgtcgcgt tacctaaccg
   301 acatgactct tgaggaaatg tcaagggaat ggtccatgct catacccaag cagaaagtgg
   361 caggccctct ttgtatcaga atggaccagg cgatcatgga taaaaacatc atactgaaag
   421 cgaacttcag tgtgattttt gaccggctgg agactctaat attgctaagg gctttcaccg
   481 aagagggagc aattgttggc gaaatttcac cattgccttc tcttccagga catactgctg
   541 aggatgtcaa aaatgcagtt ggagtcctca tcggaggact tgaatggaat gataacacag
   601 ttcgagtctc tgaaactcta cagagattcg cttggagaag cagtaatgag aatgggagac
   661 ctccactcac tccaaaacag aaacgagaaa tggcgggaac aattaggtca gaagtttgaa
   721 gaaataagat ggttgattga agaagtgaga cacaaactga aggtaacaga gaatagtttt
   781 gagcaaataa catttatgca agccttacat ctattgcttg aagtggagca agagataaga
   841 actttctcat ttcagcttat ttaataataa aaacacccct tgtttctact
```

Nonstructural Protein NS1 (SEQ ID NO:2)
MDPNTVSSFQVDCFLWHVRKRVADQELGDAPFLDRLRRDQKSLRGRGSTLGLDIETATRAGKQIVERILKEESDEAL
KMTMASVPASRYLTDMTLEEMSREWSMLIPKQKVAGPLCIRMDQAIMDKNIILKANFSVIFDRLETLILLRAFTEEG
AIVGEISPLPSLPGHTAEDVKNAVGVLIGGLEWNDNTVRVSETLQRFAWRSSNENGRPPLTPKQKREMAGTIRSEV Nonstructural Protein NS2 (SEQ ID NO:3)
MDPNTVSSFQDILLRMSKMQLESSSEDLNGMITQFESLKLYRDSLGEAVMRMGDLHSLQNRNEKWREQLGQKFEEIR
WLIEEVRHKLKVTENSFEQITFMQALHLLLEVEQEIRTFSFQLI

Figure 10

GenBank Accession No. CY009640
H3N2 Influenza A Virus (A/Udorn/72)
NS1 gene, NS2 gene, nonstructural protein 1, nonstructural protein 2
segment 8, complete sequence

H3N2 segment 8 (SEQ ID NO:4)

```
  1 gtgacaaaga cataatggat tccaacactg tgtcaagttt tcaggtagat tgcttccttt
 61 ggcatgtccg aaaacaagtt gtagaccaag aactaggtga tgccccattc cttgatcggc
121 ttcgccgaga tcagaagtcc ctaaggggaa gaggcagcac tctcggtcta aacatcgaag
181 cagccaccca tgttggaaag cagatagtag agaagattct gaaggaagaa tctgatgagg
241 cacttaaaat gaccatggcc tccacacctg cttcgcgata cataactgac atgactattg
301 aggaattgtc aagggactgg ttcatgctaa tgcccaagca gaaagtggaa ggacctcttt
361 gcatcagaat agaccaagca atcatggata gaacatcat gttgaaagcg aatttcagtg
421 tgattttga ccggctagag accctaatat tactaagggc tttcaccgaa gagggagcaa
481 ttgttggcga aatctcacca ttgccttctt ttccaggaca tactattgag gatgtcaaaa
541 atgcaattgg ggtcctcatc ggaggacttg aatggaatga taacacagtt cgagtctcta
601 aaactctaca gagattcgct tggggaagca gtaatgagaa tgggagacct ccacttactc
661 caaaacagaa acggaaaatg gcgagaacag ctaggtcaaa agttcgaaga gataagatgg
721 ctgattgaag aagtgagaca cagactgaag acaacagaga atagttttga gcaaataaca
781 ttcatgcaag ccttacagct actatttgaa gtggaacagg agataagaac tttctcgttt
841 cagcttattt aat
```

Nonstructural Protein NS1 (SEQ ID NO:5)
MDSNTVSSFQVDCFLWHVRKQVVDQELGDAPFLDRLRRDQKSLRGRGSTLGLNIEAATHVGKQIVEKILKEESDEAL
KMTMASTPASRYITDMTIEELSRDWFMLMPKQKVEGPLCIRIDQAIMDKNIMLKANFSVIFDRLETLILLRAFTEEG
AIVGEISPLPSFPGHTIEDVKNAIGVLIGGLEWNDNTVRVSKTLQRFAWGSSNENGRPPLTPKQKRKMARTARSKVR
RDKMAD

Nonstructural Protein NS2 (SEQ ID NO:6)
MDSNTVSSFQDILLRMSKMQLGSSSEDLNGMITQFESLKLYRDSLGEAVMRMGDLHLLQNRNGKWREQLGQKFEEIR
WLIEEVRHRLKTTENSFEQITFMQALQLLFEVEQEIRTFSFQLI

Figure 11

GenBank Accession No. DQ360842
H5N1 Influenza A Virus (A/Thailand/676/2005)
NS1 gene, NS2 gene, nonstructural protein 1, nonstructural protein 2
segment 8, complete sequence H5N1 segment 8 (SEQ ID NO:7)
```
  1 ggtgacaaaa acataatgga ttccaacact gtgtcaagct ttcaggtaga ctgctttctt
 61 tggcatgtcc gcaaacgatt tgcagaccga gaactgggtg atgccccatt ccttgaccgg
121 cttcgccgag atcagaagtc cctaagagga agaggcaaca ctcttggtct ggacatcgaa
181 acagctactc gcgcaggaaa gcagatagtg gagcggattc tggaggagga gtctgataag
241 gcacttaaaa tgccggcttc acgctaccta actgacatga ctctcgaaga aatgtcaagg
301 gactggttca tgctcatgcc caagcagaaa gtggcaggtt cccttttgcat caaaatggac
361 caggcaataa tggataaagt catcatattg aaagcaaact tcagtgtgat ttttgaccga
421 ttggaaaccc taatactact tagagctttc acagaagaag gagcaatcgt gggagaaatc
481 tcaccattac cttctcttcc aggacatact ggtgaggatg tcaaaaatgc aattggcgtc
541 ctcatcggag gacttgaatg gaatgataac acagttcaag tcactgaaac tctacagaga
601 ttcgcttgga gaagcagtga tgaggatggg agacttccac tccctccaaa tcagaaacgg
661 aaaatggcga gaacaattga gtcagaagtt tgaagaaata aggtggctga ttgaagaagt
721 aagcacataga ttgaaaatta cagaaaacag cttcgaacag ataacgttta tgcaagcctt
781 acaactactg cttgaagtgg agcaagagat aagagccttc tcgtttcagc ttatttaatg
841 ataaaaaaca c
```

Nonstructural Protein NS1 (SEQ ID NO:8)
MDSNTVSSFQVDCFLWHVRKRFADRELGDAPFLDRLRRDQKSLRGRGNTLGLDIETATRAGKQIVERILEEESDKAL
KMPASRYLTDMTLEEMSRDWFMLMPKQKVAGSLCIKMDQAIMDKVIILKANFSVIFDRLETLILLRAFTEEGAIVGE
ISPLPSLPGHTGEDVKNAIGVLIGGLEWNDNTVQVTETLQRFAWRSSDEDGRLPLPPNQKRKMARTIESEV Nonstructural Protein NS2 (SEQ ID NO:9)
MDSNTVSSFQDILVRMSKMQLASSSEDLNGMITQFKSLKLYRDSLGEAVMRMGDFHSLQIRNGKWREQLSQKFEEIR
WLIEEVRHRLKITENSFEQITFMQALQLLLEVEQEIRAFSFQLI

Figure 12

GenBank Accession No. AY651552
H5N1 Influenza A Virus (A/Viet Nam/1194/2004)
NS1 gene, NS2 gene, nonstructural protein 1, nonstructural protein 2
segment 8, complete sequence H5N1 segment 8 (SEQ ID NO:10)
```
  1 atggattcca acactgtgtc aagctttcag gtagactgct ttctttggca tgtccgcaaa
 61 cgatttgcag accaagaact gggtgatgcc ccattccttg accggcttcg ccgagatcag
121 aagtccctaa gaggaagagg caacactctt ggtctggaca tcgaaacagc tactcgcgca
181 ggaaagcaga tagtggagcg aattctggag gaggagtctg ataaggcact taaaatgccg
241 gcttcacgct acctaactga catgactctc gaagaaatgt caagggactg gttcatgctc
301 atgcccaagc agaaagtggc aggttccctt tgcatcaaaa tggaccaggc aataatggat
361 aaaaccatca tattgaaagc aaacttcagt gtgattttg accggttgga accctaata
421 ctacttagag ctttcacaga agaggggca atcgtgggag aaatctcacc attccttct
481 cttccaggac atactggtga ggatgtcaaa aatgcaattg gcgtcctcat cggaggactt
541 gaatggaatg ataacacagt tcgagtcact gaaactatac agagattcgc ttggagaaac
601 agtgatgagg atgggagact tccactccct ccaaatcaga aacggaaaat ggcgagaaca
661 attgagtcag aagtttgaag aaataaggtg gctgattgaa gaagtaagac atagattgaa
721 aattacagaa aacagcttcg aacagataac gtttatgcaa gccttacaac tactgcttga
781 agtggagcaa gagataagag ccttctcgtt tcagcttatt taa
```

Nonstructural Protein NS1 (SEQ ID NO:11)
MDSNTVSSFQVDCFLWHVRKRFADQELGDAPFLDRLRRDQKSLRGRGNTLGLDIETATRAGKQIVERILEEESDKAL
KMPASRYLTDMTLEEMSRDWFMLMPKQKVAGSLCIKMDQAIMDKTIILKANFSVIFDRLETLILLRAFTEEGAIVGE
ISPLPSLPGHTGEDVKNAIGVLIGGLEWNDNTVRVTETIQRFAWRNSDEDGRLPLPPNQKRKMARTIESEV Nonstructural Protein NS2 (SEQ ID NO:12)
MDSNTVSSFQDILVRMSKMQLASSSEDLNGMITQFESLKLYRDSLGETVMRMGDFHSLQIRNGKWREQLSQKFEEIR
WLIEEVRHRLKITENSFEQITFMQALQLLLEVEQEIRAFSFQLI

Figure 13

GenBank Accession No. AF256188
H5N1 Influenza A Virus (A/Hong Kong/97/98)
NS1 gene, NS2 gene, nonstructural protein 1, nonstructural protein 2
segment 8, complete sequence

```
H5N1 segment 8 (SEQ ID NO:13)
    1 agcaaaagca gggtgacaaa aacataatgg attccaacac tgtgtcaagc tttcaggtag
   61 actgctttct ttggcgtgtc cgcaaacgat ttgcagacca agaactgggt gatgccccat
  121 tccttgaccg gcttcgccga gatcagaagt ccctaagagg aagaggcagc actcttggtc
  181 tggacatcag aactgccact cgtgaaggaa agcatatagt ggagcggatt ctggaggaag
  241 aatctgatga ggcacttaaa atgactatcg cttcagtgcc tgctccacgc tacctaactg
  301 aaatgactct tgaggaaatg tcaagggact ggttaatgct cattcccaag cagaaagtga
  361 cagggtccct ttgcattaga atggaccagg caataatgga taaagacatc atattgaaag
  421 caaactttag tgtgattttt aatcgacttg aagctctgat actacttaga gcttttacag
  481 acgaaggagc aatagtgggc gaaatctcac cattgccttc ccttccagga catactgaag
  541 aggatgtcaa aaatgcaatt ggggtcctca tcggaggact tgaatggaat gataacacag
  601 ttcgagtctc tgaaactcta cagagattca cttggagaag cagtgatgag aatgggagat
  661 ctccactccc tccaaaacag aaacggaaaa tggagagaac aattgagcca gaagtttgaa
  721 gagataagat ggttaattga agaagtgcga cataggttaa gaattacaga gaatagcttt
  781 gaacaaataa cctttatgca agccttacaa ctattgcttg aagtggagca agagataaga
  841 actttctcgt ttcagcttat ttaatgataa aaacacccct tgtttctact
```

Nonstructural Protein NS1 (SEQ ID NO:14)
MDSNTVSSFQVDCFLWRVRKRFADQELGDAPFLDRLRRDQKSLRGRGSTLGLDIRTATREGKHIVERILEEESDEAL
KMTIASVPAPRYLTEMTLEEMSRDWLMLIPKQKVTGSLCIRMDQAIMDKDIILKANFSVIFNRLEALILLRAFTDEG
AIVGEISPLPSLPGHTEEDVKNAIGVLIGGLEWNDNTVRVSETLQRFTWRSSDENGRSPLPPKQKRKMERTIEPEV Nonstructural Protein NS2 (SEQ ID NO:15)
MDSNTVSSFQDILKRMSKMQLGSSSEDLNGMITQFESLKLYRDSLGEAVMRMGDLHSLQNRNGKWREQLSQKFEEIR
WLIEEVRHRLRITENSFEQITFMQALQLLLEVEQEIRTFSFQLI

Figure 14

GenBank Accession No. AY342423
H7N7 Influenza A Virus (A/Netherlands/033/03)
NS1 gene, NS2 gene, nonstructural protein 1
segment 8, complete sequence

```
H7N7 segment 8 (SEQ ID NO:16)
     1 agcaaaagca gggtgacaaa aacataatgg attccaacac tgtgtcaagc tttcaggtag
    61 actgctttct ttggcatgtc cgcaaacgat ttgcagacca agaactgggt gatgccccat
   121 tccttgaccg gcttcgccga gatcagaaat ccctaagagg aagaggcagc actcttggtc
   181 tggacatcga gacagctact cgtgcgggaa agcagatagt ggagcggatt ctggaggaag
   241 aatctgatga ggcacttaaa atgactattg cttcagtgct ggcttcacgc tacctaactg
   301 acatgactct tgaagaaatg tcaagggact ggttcatgct catgcccaag cagaaagtgg
   361 caggttccct ttgcatcaga atggaccagg caataatgga tagaaacatc atattgaagg
   421 caaacttcag tgtggttttt gaccggctgg aaaccctaat actacttaga gctttcacag
   481 aagaaggagc aattgtggga gaaatctcac cattaccttc tcttccagga catactgatg
   541 aggatgtcaa aaatgcaatt ggggtcctca tcggaggact tgaatggaat gataacacag
   601 ttcgagtctc tgaaactcta cagagattcg cttggagaag cagtaatgag gatgggagac
   661 ctccactccc tccaaagcag aaacggaaaa tggcagaaac aattgagtca gaagtttgaa
   721 gagataagat ggctgattga agaagtgcga cataggttga agattacaga gaacagcttt
   781 gaacagatta cgtttatgca agccttacaa ctattgcttg aagtagagca agagataaga
   841 actttctcgt ttcagcttat ttaatgataa aaaacaccct tgtttctact
```

Nonstructural Protein NS1 (SEQ ID NO:17)
MDSNTVSSFQVDCFLWHVRKRFADQELGDAPFLDRLRRDQKSLRGRGSTLGLDIETATRAGKQIVERILEEESDEAL
KMTIASVLASRYLTDMTLEEMSRDWFMLMPKQKVAGSLCIRMDQAIMDRNIILKANFSVVFDRLETLILLRAFTEEG
AIVGEISPLPSLPGHTDEDVKNAIGVLIGGLEWNDNTVRVSETLQRFAWRSSNEDGRPPLPPKQKRKMARTIESEV

US 7,507,411 B2

ATTENUATED INFLUENZA NS1 VARIANTS

CROSS-REFERENCE TO RELATED APPLICATION

This application claims the benefit under 35 U.S.C. §119 (e)(1) to U.S. Provisional Application No. 60/816,208, filed Jun. 23, 2006, which application is incorporated herein by reference in its entirety.

TECHNICAL FIELD

The present invention pertains generally to influenza virus and immunogenic compositions and methods for treating and preventing influenza infection. In particular, the invention relates to the use of attenuated influenza virus variants comprising substitutions in nonstructural protein 1 (NS1) that interfere with viral replication and phosphatidylinositol 3-kinase (PI3K) activation.

BACKGROUND

Influenza is a highly contagious, acute respiratory disease that affects people of all ages. Flu viruses can be subdivided into three types, influenza A, B, and C. Of the three influenza types, influenza A and B have historically been responsible for influenza epidemics (Horimoto and Kawaoka (2001) *Clin. Microbiol. Rev.* 14:129-149; Zambon (1999) *J. Antimicrob. Chemother.* 44 Suppl B:3-9). Type A viruses are able to infect a wide variety of warm-blooded animal species including humans, pigs, horses, sea mammals, mustelids and birds. In contrast, type B and C viruses are mostly confined to humans.

The genomes of flu viruses consist of negative sense single-stranded RNA. The influenza genome is segmented and consists of seven or eight fragments of RNA encoding approximately 14 proteins (Horimoto and Kawaoka, supra; Zambon, supra). Influenza A virus contains eight segments of negative stranded RNA, including segment 8, which encodes two proteins, a nonstructural protein 1 (NS1) and a nonstructural protein 2, also referred to as nuclear export protein, (NS2/NEP) (Lamb et al. (1989) *Proc. Natl. Acad. Sci. USA* 76:4908-4912). The NS1 protein of all naturally occurring influenza A viruses is about 230 amino acids in length and is expressed at high levels in infected cells. NS1 is a multifunctional protein comprising two functional domains: an RNA binding domain near the N-terminus and an effector domain at the C-terminus (Qian et al. (1994) *J. Virol.* 68:2433-2441). The RNA binding activity of NS1 is associated with its ability to inhibit cellular pre-mRNA splicing (Fortes et al. (1994) *EMBO J.* 13:704-712; Lu et al. (1994) *Genes Dev* 8:1817-1828; Qiu et al. (1995) *RNA* 1:304-316). NS1 also acts as an antagonist of host immune responses. NS1 counteracts cellular interferon-α/β functions (Garcia-Sastre et al. (1998) *Virology* 252:324-330) by inhibiting the activation of protein kinase R (PKR) (Hatada et al. (1999) *J. Virol.* 73:2425-2433; Lu et al. (1995) *Virology* 214:222-228) and transcription factors, such as NF-κB, IRF-3 and IRF-7 (Talon et al. (2000) *J. Virol.* 74:7989-7996; Wang et al. (2000) *J. Virol.* 74:11566-11573). Within the effector domain of NS1 are two binding sites for cellular proteins. A binding site for cleavage and polyadenylation specificity factor (CPSF) is positioned around amino acid 186 and a poly(A)-binding protein II (PA-BII) binding site is located in the region from residues 223-237 (Li et al. (2001) *RNA* 7:920-931). These binding sites are required for the inhibition of 3'-end processing of cellular pre-mRNAs, and are important for influenza virus replication (Noah et al. (2003) *Virology* 307:386-395).

Each year, numerous individuals are infected with different strains and types of influenza virus. Infants, the elderly, those without adequate health care, and immuno-compromised individuals are especially at risk of dying from such infections. Compounding the problem is the rapid evolution of novel influenza virus strains that spread amongst various species, thereby necessitating the continuous production of new vaccines.

Thus, there remains a need for the development of effective strategies for the treatment and prevention of influenza infection.

SUMMARY OF THE INVENTION

The present invention relates to attenuated influenza virus variants comprising substitutions in NS1 that interfere with viral replication and PI3K activation. In particular, the invention pertains to NS1 variant polypeptides, polynucleotides encoding NS1 variant polypeptides, a reverse genetics system for producing attenuated influenza virus NS1 variants, immunogenic compositions comprising live attenuated influenza virus NS1 variants, as well as methods of stimulating an immune response against influenza virus, methods of interfering with influenza virus replication, and methods of treating and preventing influenza virus infection.

Accordingly, in one embodiment, the invention is directed to an attenuated influenza virus comprising at least one mutation in the nonstructural 1 (NS1) protein of the virus, wherein the mutation is in the Src homology 2 (SH2) binding motif, the Src homology 3 (SH3) binding motif 1, or the SH3 binding motif 2 of said NS1 protein, wherein the mutation interferes with phosphatidylinositol 3-kinase (PI3K) activation and replication of said virus.

In certain embodiments, the mutation comprises an amino acid insertion, deletion and/or substitution.

In other embodiments, the virus is of type influenza A.

In additional embodiments, the invention is directed to a composition comprising an attenuated influenza virus as described above and a pharmaceutically acceptable excipient. In certain embodiments, the composition further comprises an adjuvant. In additional embodiments, the composition further comprises one or more additional immunogenic antigens.

In further embodiments, the invention is directed to a method of eliciting an immunological response in a vertebrate subject, comprising administering a composition as above to the subject.

In additional embodiments, the invention is directed to a method of treating a vertebrate subject with an influenza infection, comprising administering to the subject a therapeutically effective amount of a composition above.

In yet further embodiments, the invention is directed to a method of prophylactically enhancing an immune response by a subject to an influenza virus, comprising administering an effective amount of the above composition to the subject.

In additional embodiments, the invention is directed to a method of vaccinating a subject against an influenza virus, comprising administering an effective amount of the composition above to the subject.

In additional embodiments, the invention is directed to an isolated mutant nonstructural 1 (NS1) polypeptide comprising at least one amino acid substitution in the SH2 binding domain, the first SH3 binding domain or the second SH3 binding domain of said NS1 protein, wherein said substitution reduces phosphatidylinositol 3-kinase (PI3K) activation activity of said NS1 polypeptide compared to the PI3K activation activity of the corresponding wild-type NS1 polypeptide.

In further embodiments, the invention is directed to an isolated polynucleotide comprising a coding sequence for mutant polypeptide above. In certain embodiments, the recombinant polynucleotide further comprises a promoter sequence operably linked to the coding sequence. In additional embodiments, the invention is directed to a cell transformed with the recombinant polynucleotide.

In additional embodiments, the invention is directed to a method of producing a polypeptide. The method comprises a) culturing a cell described above under conditions suitable for expression of the polypeptide, and b) recovering the polypeptide so expressed.

In further embodiments, the invention is directed to a reverse genetics system for producing the virus described above.

In yet further embodiments, the invention is directed to a method of producing an attenuated influenza virus, comprising transfecting a host cell with the reverse genetics system, wherein the host cell is capable of supporting the growth of said virus.

In additional embodiments, the invention is directed to a method for generating a reverse genetics system for producing attenuated influenza virus, comprising mutating a polynucleotide encoding an NS1 polypeptide in a reverse genetics system that produces influenza virus, wherein the encoded NS1 polypeptide comprises a mutation in the Src homology 2 (SH2) binding motif, the Src homology 3 (SH3) binding motif 1, or the SH3 binding motif 2 of the NS1 protein, wherein the mutation interferes with phosphatidylinositol 3-kinase (PI3K) activation and replication of said virus.

In further embodiments, the invention is directed to a cell transformed with the above reverse genetics system.

In additional embodiments, the invention is directed to a method of treating a vertebrate subject for an influenza infection, comprising administering a therapeutically effective amount of the reverse genetics system to the subject.

In further embodiments, the invention is directed to a method of producing a composition comprising combining the polypeptide above with a pharmaceutically acceptable excipient.

In yet further embodiments, the invention is directed to a method of producing an influenza vaccine comprising:
 (a) growing the an attenuated virus described above;
 (b) purifying the virus; and
 (c) combining the purified attenuated virus with a pharmaceutically acceptable excipient.

In certain embodiments, the attenuated virus is grown in embryonated chicken eggs. In other embodiments, the virus is inactivated prior to step (c).

In any of the embodiments above, the mutation can comprise a substitution of the amino acid of the NS1 protein at the position corresponding to Tyr-89 of the sequence of SEQ ID NO:2 with a phenylalanine residue.

In yet further embodiments, the mutation can comprise a substitution of the amino acid of the NS1 protein at the position corresponding to Pro-164 of the sequence of SEQ ID NO:2 with an alanine residue and a substitution of the amino acid corresponding to Pro-167 of the sequence of SEQ ID NO:2 with an alanine residue.

In additional embodiments, the mutation can comprise a substitution of the amino acid of the NS1 protein at the position corresponding to Pro-212 of the sequence of SEQ ID NO:2 with an alanine residue, a substitution of the amino acid of the NS1 protein at the position corresponding to Pro-213 of the sequence of SEQ ID NO:2 with an alanine residue, and a substitution of the amino acid of the NS1 protein at the position corresponding to Pro-216 of the sequence of SEQ ID NO:2 with an alanine residue.

In further embodiments, the mutation can comprise a substitution of the amino acid of the NS1 protein at the position corresponding to Pro-164 of the sequence of SEQ ID NO:2 with an alanine residue, a substitution of the amino acid of the NS1 protein at the position corresponding to Pro-167 of the sequence of SEQ ID NO:2 with an alanine residue, a substitution of the amino acid of the NS1 protein at the position corresponding to Pro-212 of the sequence of SEQ ID NO:2 with an alanine residue, a substitution of the amino acid of the NS1 protein at the position corresponding to Pro-213 of the sequence of SEQ ID NO:2 with an alanine residue, and a substitution of the amino acid of the NS1 protein at the position corresponding to Pro-216 of the sequence of SEQ ID NO:2 with an alanine residue.

In additional embodiments, the mutation can comprise a substitution of the amino acid of the NS1 protein at the position corresponding to Tyr-89 of the sequence of SEQ ID NO:2 with a phenylalanine residue, a substitution of the amino acid of the NS1 protein at the position corresponding to Pro-164 of the sequence of SEQ ID NO:2 with an alanine residue, a substitution of the amino acid of the NS1 protein at the position corresponding to Pro-167 of the sequence of SEQ ID NO:2 with an alanine residue, a substitution of the amino acid of the NS1 protein at the position corresponding to Pro-212 of the sequence of SEQ ID NO:2 with an alanine residue, a substitution of the amino acid of the NS1 protein at the position corresponding to Pro-213 of the sequence of SEQ ID NO:2 with an alanine residue, and a substitution of the amino acid of the NS1 protein at the position corresponding to Pro-216 of the sequence of SEQ ID NO:2 with an alanine residue.

In yet further embodiments, the mutation can comprise a sequence selected from SEQ ID NOS:18-47.

These and other embodiments of the subject invention will readily occur to those of skill in the art in view of the disclosure herein.

BRIEF DESCRIPTION OF THE FIGURES

FIG. 1A shows domains of the PI3K regulatory subunit p85, including two Src homology 2 (SH2) domains, the Src homology 3 (SH3) domain, the breakpoint cluster region (BCR) homology domain, and the p110 binding domain that binds to the PI3K catalytic subunit p110. FIG. 1B shows an alignment of NS1 proteins from influenza A H1N1 (SEQ ID NO:2), H3N2 (SEQ ID NO:5), H5N1 (SEQ ID NOS:8, 11 and 14, respectively, beginning at residue 84 for SEQ ID NOS:8 and 11) and H7N7 (SEQ ID NO:17) strains. Consensus amino acids in the SH2 and SH3 binding domains are shown in bold.

FIG. 2A depicts a Western blot showing that the NS1 protein interacts with the p85 subunit of PI3K in vivo. Serum starved A549 cells were mock infected or wild-type (wt) PR8 virus infected at a multiplicity of infection (m.o.i) of 1. Cell lysates were harvested at 6 hours post infection (h.p.i.) and incubated with either normal rabbit serum-protein A or p85 antiserum-protein A complexes. Precipitated proteins were subjected to Western blotting with polyclonal NS1 antibody. FIG. 2B shows the results from a GST pull down assay with wt virus infected cell lystates. GST alone, or fusions of GST to SH3, SH2C or SH2N domain of p85 subunit were immobilized to GA beads. Mock or wt PR8 virus (MOI of 1 PFU/cell) infected A549 cells lysates were prepared at 6 h.p.i. and incubated with GST fusion protein-GA beads complexes. Precipitated proteins were either subjected to Western blotting with polyclonal NS1 antibody (upper panel) or SDS-PAGE followed by Coomassie blue staining (lower panel).

FIG. 3A depicts a Western blot showing changes in phosphorylated Akt as a result of NS1 expression. A549 cells were electroporated and transfected with plasmid DNA expressing wt NS1 or empty vector pcDNA3.1(−). 72 hours later, cell lysates were subjected to Western blotting analysis with antibodies against phospho-Akt (top panel), total Akt (middle panel) and NS1 (bottom panel), respectively. FIG. 3B shows the results from a GST pull down assay. 293T cells were transfected with either vector or pcDNA-NS and analyzed 48 hours later by GST pull down assay as described in the legend to FIG. 2B. Precipitated proteins were either subjected to Western blotting with polyclonal NS1 antibody (upper panel) or SDS-PAGE followed by Coomassie blue staining (lower panel).

FIG. 5A shows that PR8-SH2/SH3mt fails to induce phosphorylation of Akt. Serum starved A549 cells were mock infected or wt PR8, PR8-SH2/SH3mt infected (MOI of 1 PFU/cell). Cell lysates were prepared at 6 h.p.i. and subjected to Western blotting with phospho-Akt (top panel), total Akt (middle panel) and NS1 (bottom panel) antibody, respectively. FIG. 5B shows that higher doses of mutant virus do not induce Akt phosphorylation. Serum starved A549 cells were infected with different MOI of mutant virus. Cell lysates were prepared at 6 h.p.i. and subjected to Western blotting with phospho-Akt (top panel), total Akt (middle panel) and NS1 (bottom panel) antibody, respectively. FIG. 5C shows the results of a GST pull down assay with mutant virus PR8-SH2/SH3mt infected cell lysates as described in the legend to FIG. 2B.

FIG. 6A compares plaques formed by wt PR8 and mutant PR8-SH2/SH3mt viruses in MDCK cells. FIG. 6B compares viral titers of wt PR8 and mutant PR8-SH2/SH3mt during multiple cycles of growth over 72 hours. MDCK cells were infected with either wt or mutant virus at MOI of 0.001 PFU/cell. At the indicated times post infection, virus titers in the supernatant were determined by plaque assay in MDCK cells.

FIG. 9 shows the nucleotide sequence of segment 8 from the influenza A H1N1 strain Puerto Rico/8/34 (SEQ ID NO:1) and the amino acid sequences of the encoded proteins, NS1 (SEQ ID NO:2) and NS2 (SEQ ID NO:3).

FIG. 10 shows the nucleotide sequence of segment 8 from the influenza A H3N2 strain Udorn/72 (SEQ ID NO:4) and the amino acid sequences of the encoded proteins, NS1 (SEQ ID NO:5) and NS2 (SEQ ID NO:6).

FIG. 11 shows the nucleotide sequence of segment 8 from the influenza A H5N1 strain Thailand/676/2005 (SEQ ID NO:7) and the amino acid sequences of the encoded proteins, NS1 (SEQ ID NO:8) and NS2 (SEQ ID NO:9).

FIG. 12 shows the nucleotide sequence of segment 8 from the influenza A H5N1 strain Viet Nam/1194/2004 (SEQ ID NO:10) and the amino acid sequences of the encoded proteins, NS1 (SEQ ID NO:11) and NS2 (SEQ ID NO:12).

FIG. 13 shows the nucleotide sequence of segment 8 from the influenza A H5N1 strain Hong Kong/97/98 (SEQ ID NO:13) and the amino acid sequences of the encoded proteins, NS1 (SEQ ID NO:14) and NS2 (SEQ ID NO:15).

FIG. 14 shows the nucleotide sequence of segment 8 from the influenza A H7N7 strain Netherlands/033/03 (SEQ ID NO:16) and the amino acid sequence of the encoded protein, NS1 (SEQ ID NO:17).

DETAILED DESCRIPTION OF THE INVENTION

Figure 1:
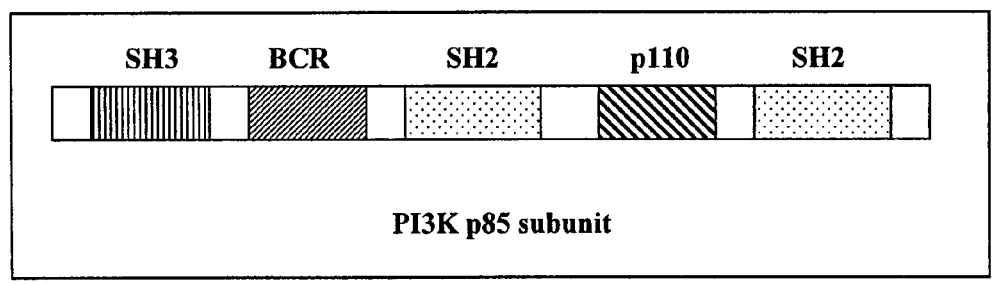
FIGS. 1A and 1B depict schematic representations of p85 and NS1.

The practice of the present invention will employ, unless otherwise indicated, conventional methods of virology, chemistry, biochemistry, recombinant DNA techniques and immunology, within the skill of the art. Such techniques are explained fully in the literature. See, e.g., *Fundamental Virology*, 3rd Edition, vol. I & II (B. N. Fields and D. M. Knipe, eds.); *Handbook of Experimental Immunology*, Vols. I-IV (D. M. Weir and C. C. Blackwell eds., Blackwell Scientific Publications); T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.).

All publications, patents and patent applications cited herein, whether supra or infra, are hereby incorporated by reference in their entireties.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "an influenza A virus" includes a mixture of two or more such viruses, and the like.

As used herein, the term "influenza virus" refers to members of the orthomyxoviridae family of enveloped viruses with a segmented antisense RNA genome (Knipe and Howley (eds.) Fields Virology, 4th edition, Lippincott Williams and Wilkins, Philadelphia, Pa., 2001). The term influenza virus may include any strain of influenza virus, such as influenza A, B, or C, which is capable of causing disease in an animal or human subject. In particular, the term encompasses any subtype of influenza A virus selected from H1-H15 and N1-N9 (e.g., H1N1, H3N2, H5N1, H7N7, and H9N2) that causes disease in humans. A large number of influenza isolates have been partially or completely sequenced. See, e.g., the Influenza Sequence Database (ISD) (website at flu.lanl.gov; described by Macken et al., "The value of a database in surveillance and vaccine selection." in *Options for the Control of Influenza IV*. A. D. M. E. Osterhaus, N. Cox & A. W. Hampson (Eds.) Amsterdam: Elsevier Science, 2001, 103-106) and the GenBank database, particularly the Influenza Virus Resource (website at ncbi.nlm.nih.gov/genomes/FLU/FLU.html). The ISD and GenBank databases contain complete sequences for influenza A, B and C genome segments.

As used herein, the term "SH2 binding motif" in reference to an influenza virus NS1 polypeptide refers to amino acid residues 89-93 in the reference sequence of SEQ ID NO:2 or the corresponding positions in NS1 polypeptides derived from any type or strain of influenza virus.

As used herein, the term "SH3 binding motif 1" in reference to an influenza virus NS1 protein refers to amino acid residues 164-167 in the reference sequence of SEQ ID NO:2 or the corresponding positions in NS1 polypeptides derived from any type or strain of influenza virus.

As used herein, the term "SH3 binding motif 2" in reference to an influenza virus NS1 protein refers to amino acid residues 212-216 in the reference sequence of SEQ ID NO:2 or the corresponding positions in NS1 polypeptides derived from any type or strain of influenza virus.

As used herein, the term "attenuated" means that an influenza virus variant exhibits a reduction in replication efficiency relative to wild-type influenza virus. The replication efficiency of an influenza virus may be determined, for example, by measuring plaque size in MDCK cells or by measuring virus titers over multiple growth cycles.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein which includes modifications, such as deletions, additions and substitutions, to the native sequence, so long as the protein maintains the desired activity. These modifications may be deliberate, as through site-directed mutagenesis, or may be accidental, such as through mutations of hosts which produce the proteins or errors due to PCR amplification.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353-358, National biomedical Research Foundation, Washington, D.C., which adapts the local homology algorithm of Smith and Waterman *Advances in Appl. Math.* 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60;

expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning, supra; Nucleic Acid Hybridization,* supra.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. In particular, DNA is deoxyribonucleic acid.

The term "derived from" is used herein to identify the original source of a molecule but is not meant to limit the method by which the molecule is made which can be, for example, by chemical synthesis or recombinant means.

An influenza virus molecule is a molecule derived from an influenza virus, including, without limitation, polypeptide, protein, polynucleotide, oligonucleotide, and nucleic acid molecules, as defined above, from any of the various isolates of influenza subtypes A, B, or C. The molecule need not be physically derived from the particular isolate in question, but may be synthetically or recombinantly produced.

Nucleic acid and polypeptide sequences for a number of influenza virus isolates are known. Representative influenza sequences are presented in FIGS. 9-14. Additional representative sequences, including sequences for hemagglutinin (HA), neuraminidase (NA), polymerase acidic protein (PA), polymerase basic proteins 1 and 2 (PB1 and PB2), matrix proteins 1 and 2 (M1 and M2), membrane ion channel (M2), nucleoprotein (NP), and nonstructural proteins 1 and 2 (NS1 and NS2) from influenza isolates found in various species of birds and mammals are listed in the National Center for Biotechnology Information (NCBI) database. For a listing of representative NS1 sequences, see, for example, GenBank entries: Puerto Rico/8/34 H1N1 segment 8, GenBank Accession No. J02150; swine H1N1 nonstructural protein 2 and nonstructural protein 1, GenBank Accession No. M55484; A/WSN/1933 TS61 H1N1 segment 8, GenBank Accession No. CY010792; A/New York/235/2001 H1N1 segment 8, GenBank Accession No. CY010856; A/New York/638/1995 H1N1 segment 8, GenBank Accession No. CY010824; A/Canterbury/42/2001H1N1 segment 8, GenBank Accession No. CY010784; A/Wilson-Smith/1933 H1N1 nonstructural protein 2 (NS2) and nonstructural protein 1 (NS1) GenBank Accession No. DQ508909; A/USSR/90/1977H1N1 nonstructural protein 2 (NS2) and nonstructural protein 1 (NS1), GenBank Accession No. DQ508901; A/Texas/36/1991 H1N1 nonstructural protein 2 (NS2) and nonstructural protein 1 (NS1) genes, GenBank Accession No. DQ508893; A/Taiwan/01/1986 H1N1 nonstructural protein 2 (NS2) and nonstructural protein 1 (NS1) genes, GenBank Accession No. DQ508877; goose H1N1 nonstructural protein NS2 (NS) gene, partial cds, alternatively spliced; and nonstructural protein NS1 (NS) gene, complete cds, GenBank Accession No. U49495; A/Puerto Rico/8/34 H1N1 segment 8, GenBank Accession No. NC__002020; swine H1N1 segment 8, GenBank Accession No. CY009920; pigeon H1N1 segment 8, GenBank Accession No. CY005870; mallard duck H1N1 segment 8, Genbank Accession No. CY005807; pintail duck H1N1 segment 8, GenBank Accession No. CY004550; swine H3N2 nonstructural protein 2 and nonstructural protein 1, GenBank Accession No. M55483; A/Alaska/6/1977 H3N2 non-structural protein NS2 and non-structural protein NS1, GenBank Accession No. K01332; A/New York/623/1995 H3N2 segment 8, GenBank Accession No. CY010816; A/Udorn/307/1972H3N2 nonstructural protein 2 (NS2) and nonstructural protein 1 (NS1) genes, GenBank Accession No. DQ508933; A/Panama/2007/1999 H3N2 nonstructural protein 2 (NS2) and nonstructural protein 1 (NS1) genes, GenBank Accession No. DQ508869; A/Leningrad/360/1986 H3N2 nonstructural protein 2 (NS2) and nonstructural protein 1 (NS1) genes, GenBank Accession No. DQ508853; A/Beijing/353/1989 H3N2 nonstructural protein 2 (NS2) and nonstructural protein 1 (NS1) genes, GenBank Accession No. DQ508837; A/Bangkok/01/1979 H3N2 nonstructural protein 2 (NS2) and nonstructural protein 1 (NS1) genes, GenBank Accession No. DQ508829; A/Memphis/101/72 H3N2 segment 8, GenBank Accession No. CY008680; A/Canterbury/71/2000 H3N2 segment 8, GenBank Accession No. CY008776; pintail duck H3N2 segment 8, GenBank Accession No. CY004580; goose H3N2 segment 8, GenBank Accession No. CY005561; A/Whanganui/386/2004 H3N2 segment 8, GenBank Accession No. CY007327; A/New York/528/1998 H3N2 segment 8, GenBank Accession No. CY006543; dove H3N2 NS1 and NS2 genes, GenBank Accession No. AY862676; duck H3N2 NS1 and NS2 genes, GenBank Accession No. AY862675; chicken H3N2 NS1 and NS2 genes, GenBank Accession No. AY862671; swine H3N2 non-structural protein NS2 and non-structural protein NS1 (NS) gene, GenBank Accession No. AY363598; A/sw/Shizuoka/119/97 H3N2 nonstructural protein (NS) RNA, complete cds, alternatively spliced, GenBank Accession No. AF225532; A/Hong Kong/1/68 H3N2 isolate MA20b nonstructural protein NS1 and nonstructural protein NS2 genes, GenBank Accession No. AF348206; A/Vietnam/CL2009/2005 H5N1 nonstructural protein 2 (NS2) and nonstructural protein 1 (NS1) genes, GenBank Accession No. DQ493254; A/Hong Kong/97/98 H5N1 nonstructural protein NS1 and nuclear export protein NS2 (NS) gene, GenBank Accession No. AF256188; A/Hong Kong/542/97(H5N1)) nonstructural protein NS1 and nuclear export protein NS2 (NS) gene, GenBank Accession No. AF256187; A/Environment/Hong Kong/437-10/99 H5N1 nonstructural protein 1 and nonstructural protein 2 genes, GenBank Accession No. AF216734; A/Hong Kong/486/97 H5N1 segment 8 nonstructural protein 1 (NS1) and nonstructural protein 2 (NS2) genes, GenBank Accession No. AF115289; chicken H5N1 nonstructural protein, GenBank Accession No. AY818148; chicken H5N1 NS2, NS1 genes for nonstructural protein 2, nonstructural protein 1, GenBank Accession No. AB189049; chicken H5N1 non-structural protein 2 and non-structural protein 1, GenBank Accession No. AY676051; chicken H5N1 segment 8, GenBank Accession No. AY737300; duck H5N1 non-structural protein 2 and non-structural protein 1, GenBank Accession No. AY676052; duck H5N1 segment 8, GenBank Accession No. AY737307; Goose H5N1 nonstructural protein 1 and nonstructural protein 2, GenBank Accession No. AY075032; Goose H5N1 nonstructural protein 1 and nonstructural protein 2, GenBank Accession No. AY028445; egret H5N1 nonstructural protein 2 and non-structural protein 1, GenBank Accession No. AY676050; quail H5N1 nonstructural protein NS1, GenBank Accession No. AY818149; crow H5N1 nonstructural protein 2, nonstructural protein 1, GenBank Accession No. AB189065; peregrine falcon H5N1 nonstructural protein 2 and nonstructural protein 1, GenBank Accession No. AY651582; black headed gull H5N1 nonstructural protein 2 and nonstructural protein 1, GenBank Accession No. AY651577; grey heron H5N1 nonstructural protein 2 and nonstructural protein 1, AY651578; pheasant H5N1 NS1 protein, GenBank Accession No. AF509070; pigeon H5N1 NS1 protein, GenBank Accession No. AF509073; feral pigeon H5N1 nonstructural protein 2 and nonstructural protein 1, GenBank Accession No. AY651579; quail H5N1 nonstructural protein NS1, GenBank Accession No. AY818149; sparrow H5N1 nonstructural protein 2, and nonstructural protein 1, GenBank Accession No. AY651580; turkey H5N1 nonstructural protein NS2 and nonstructural protein NS1, GenBank Accession No. IAU85447; tiger H5N1 nonstructural protein 1, GenBank Accession No. AY907674; leopard H5N1 nonstructural protein, GenBank Accession No. AY646178; swine H5N1 nonstructural protein NS1, GenBank Accession No. AY747613; pheasant H6N1 nonstructural protein 1, GenBank Accession No. AJ427312; duck nonstructural protein 1 H6N1 GenBank Accession No. AJ410596; duck H6N1 NS1 and NS2 genes, GenBank Accession No. AY862677; quail H6N1 nonstructural protein 1, GenBank Accession No. AJ410581; chicken H6N1 nonstructural protein GenBank Accession No. AF262212; pintail H6N1 nonstructural protein (NS), GenBank Accession No. AY633336; teal H6N1 segment 8 nonstructural protein 1 and nonstructural protein 2, GenBank Accession No. AF250483; chicken H7N7 nonstructural protein, GenBank Accession No. AY342424; chicken H7N7 nonstructural protein (NS1 and NS2), GenBank Accession No. L37798; A/FPV/Weybridge H7N7 nonstructural protein (NS2) and nonstructural protein (NS1) genes, GenBank Accession No. L37800; A/FPV/Dobson H7N7 segment 8 nonstructural protein (NS2) and nonstructural protein (NS1) genes, GenBank Accession No. L37799; duck H7N7 genomic RNA, segment 8, GenBank Accession No. AB243424; A/red knot/NJ/325/1989 H7N7 segment 8, GenBank Accession No. CY005082; A/ruddy turnstone/DE/2378/1988 H7N7 segment 8, GenBank Accession No. CY005075; A/eq/Prague/1/1956 H7N7 segment 8, GenBank Accession No. CY005804; SC35M NEP/NS2 and NS1 genes, GenBank Accession No. DQ266101; A/eq/Newmarket/1/77 H7N7 nonstructural proteins NS1 and NS2 (NS) gene, GenBank Accession No. AF001663; chicken H9N2 nonstructural protein, GenBank Accession No. AY800237; chicken H9N2 NS2 and NS1, GenBank Accession No. AY966002; duck H9N2 NS1 and NS2, GenBank Accession No. AY862666; mallard H9N2 nonstructural protein, GenBank Accession No. AY633296; pheasant H9N2 nonstructural protein 2 and nonstructural protein 1, GenBank Accession No. AY664749; pigeon H9N2 nonstructural protein 2 and nonstructural protein 1, GenBank Accession No. AY664748; guineafowl H9N2 nonstructural protein 2 and nonstructural protein 1, GenBank Accession No. AY664750; parakeet H9N2 nonstructural protein 2, nonstructural protein 1, GenBank Accession No. AB049168; and swine H9N2 NS gene, GenBank Accession No. AY790324; all of which sequences (as entered by the date of filing of this application) are herein incorporated by reference. See also Ferguson et al. (2003) Nature 422: 428-433; Lin et al. (2000) Proc. Natl. Acad. Sci. U.S.A. 97, 9654-9658; Nguyen et al. (2005) J. Virol. 79:4201-4212; Ha et al. (2002) EMBO J. 21:865-875; and Chan et al. (2004) J. Microbiol. Immunol. Infect. 37:135-144; for sequence comparisons and a discussion of genetic diversity and phylogenetic analysis of influenza virus.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

"Recombinant" as used herein to describe a nucleic acid molecule means a polynucleotide of genomic, cDNA, viral, semisynthetic, or synthetic origin which, by virtue of its origin or manipulation is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences. "Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

By "fragment" is intended a molecule consisting of only a part of the intact full-length sequence and structure. A fragment of a polypeptide can include a C-terminal deletion, an N-terminal deletion, and/or an internal deletion of the native polypeptide. A fragment of a polypeptide will generally include at least about 5-10 contiguous amino acid residues of the full-length molecule, preferably at least about 15-25 contiguous amino acid residues of the full-length molecule, and most preferably at least about 20-50 or more contiguous amino acid residues of the full-length molecule, or any integer between 5 amino acids and the number of amino acids in the full-length sequence, provided that the fragment in question retains the ability to elicit the desired biological response. A fragment of a nucleic acid can include a 5'-deletion, a 3'-deletion, and/or an internal deletion of a nucleic acid. Nucleic acid fragments will generally include at least about 5-1000 contiguous nucleotide bases of the full-length molecule and may include at least 5, 10, 15, 20, 25, 30, 40, 50, 60, 75, 100, 150, 250 or at least 500 contiguous nucleotides of the full-length molecule, or any integer between 5 nucleotides and the number of nucleotides in the full-length sequence. Such fragments may be useful in hybridization, amplification, production of immunogenic fragments, or nucleic acid immunization.

By "immunogenic fragment" is meant a fragment of an immunogen which includes one or more epitopes and thus can modulate an immune response or can act as an adjuvant for a co-administered antigen. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols, supra*. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl.*

*Acad. Sci. USA* (1981) 78:3824-3828 for determining antigenicity profiles, and the Kyte-Doolittle technique, Kyte et al., *J. Mol. Biol.* (1982) 157:105-132 for hydropathy plots.

Immunogenic fragments, for purposes of the present invention, will usually be at least about 2 amino acids in length, more preferably about 5 amino acids in length, and most preferably at least about 10 to about 15 amino acids in length. There is no critical upper limit to the length of the fragment, which could comprise nearly the full-length of the protein sequence, or even a fusion protein comprising two or more epitopes.

As used herein, the term "epitope" generally refers to the site on an antigen which is recognised by a T-cell receptor and/or an antibody. Preferably it is a short peptide derived from or as part of a protein antigen. However the term is also intended to include peptides with glycopeptides and carbohydrate epitopes. Several different epitopes may be carried by a single antigenic molecule. The term "epitope" also includes modified sequences of amino acids or carbohydrates which stimulate responses which recognize the whole organism. It is advantageous if the selected epitope is an epitope of an infectious agent, which causes the infectious disease.

The epitope can be generated from knowledge of the amino acid and corresponding DNA sequences of the peptide or polypeptide, as well as from the nature of particular amino acids (e.g., size, charge, etc.) and the codon dictionary, without undue experimentation. See, e.g., Ivan Roitt, Essential Immunology, 1988; Kendrew, supra; Janis Kuby, Immunology, 1992 e.g., pp. 79-81. Some guidelines in determining whether a protein will stimulate a response, include: Peptide length—preferably the peptide is about 8 or 9 amino acids long to fit into the MHC class I complex and about 13-25 amino acids long to fit into a class II MHC complex. This length is a minimum for the peptide to bind to the MHC complex. It is preferred for the peptides to be longer than these lengths because cells may cut peptides. The peptide may contain an appropriate anchor motif which will enable it to bind to the various class I or class II molecules with high enough specificity to generate an immune response (See Bocchia, M. et al, Specific Binding of Leukemia Oncogene Fusion Protein Peptides to HLA Class I Molecules, Blood 85:2680-2684; Englehard, V H, Structure of peptides associated with class I and class II MHC molecules Ann. Rev. Immunol. 12:181 (1994)). This can be done, without undue experimentation, by comparing the sequence of the protein of interest with published structures of peptides associated with the MHC molecules. Thus, the skilled artisan can ascertain an epitope of interest by comparing the protein sequence with sequences listed in the protein database.

An "immunological response" to an antigen or composition is the development in a subject of a humoral and/or a cellular immune response to an antigen present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface.

A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376. Recent methods of measuring cell-mediated immune response include measurement of intracellular cytokines or cytokine secretion by T-cell populations, or by measurement of epitope specific T-cells (e.g., by the tetramer technique) (reviewed by McMichael, A. J., and O'Callaghan, C. A., *J. Exp. Med.* 187(9)1367-1371, 1998; Mcheyzer-Williams, M. G., et al, *Immunol. Rev.* 150: 5-21, 1996; Lalvani, A., et al, *J. Exp. Med.* 186:859-865, 1997).

Thus, an immunological response as used herein may be one that stimulates the production of antibodies (e.g., neutralizing antibodies that block bacterial toxins and pathogens such as viruses entering cells and replicating by binding to toxins and pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art. (See, e.g., Montefiori et al. (1988) *J. Clin Microbiol.* 26:231-235; Dreyer et al. (1999) *AIDS Res Hum Retroviruses* (1999) 15(17):1563-1571). The innate immune system of mammals also recognizes and responds to molecular features of pathogenic organisms via activation of Toll-like receptors and similar receptor molecules on immune cells. Upon activation of the innate immune system, various non-adaptive immune response cells. are activated to, e.g., produce various cytokines, lymphokines and chemokines. Cells activated by an innate immune response include immature and mature Dendritic cells of the monocyte and plamsacytoid lineage (MDC, PDC), as well as gamma, delta, alpha and beta T cells and B cells and the like. Thus, the present invention also contemplates an immune response wherein the immune response involves both an innate and adaptive response.

An "immunogenic composition" is a composition that comprises an antigenic molecule where administration of the composition to a subject results in the development in the subject of a humoral and/or a cellular immune response to the antigenic molecule of interest.

The terms "immunogenic" protein or polypeptide refer to an amino acid sequence which elicits an immunological response as described above. An "immunogenic" protein or polypeptide, as used herein, includes the full-length sequence of the protein in question, including the precursor and mature forms, analogs thereof, or immunogenic fragments thereof.

An "antigen" refers to a molecule, such as a protein, polypeptide, or fragment thereof, or an attenuated virus, containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens, (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses. When used for immunization, such gene delivery expression vectors may be referred to as vaccines or vaccine vectors.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. In particular, influenza virus may be obtained from biological samples such as nasal, nasopharyngeal, throat, or conjunctival secretions, blood, or anal swabs from an individual infected with the virus.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

By "therapeutically effective amount" in the context of the immunogenic compositions is meant an amount of an immunogen (e.g., attenuated influenza virus comprising one or more substitutions in NS1 as described herein, immunogenic polypeptide, or nucleic acid encoding an antigen) which will induce an immunological response, either for antibody production or for treatment or prevention of influenza virus infection. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γδT cell populations.

For purposes of the present invention, an "effective amount" of an adjuvant will be that amount which enhances an immunological response to a coadministered antigen or nucleic acid encoding an antigen.

As used herein, "treatment" refers to any of (i) the prevention of infection or reinfection, as in a traditional vaccine, (ii) the reduction or elimination of symptoms, and (iii) the substantial or complete elimination of influenza virus from an infected individual. Treatment may be effected prophylactically (prior to infection) or therapeutically (following infection).

2. Modes of Carrying Out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention provides compositions and methods for treating or preventing influenza infection. The invention is based on the discovery that mutations in the SH2 binding and SH3 binding domains of the influenza virus NS1 protein interfere with PI3K activation, block viral protein synthesis, and attenuate viral replication. In particular, the invention pertains to immunogenic compositions comprising live attenuated influenza virus NS1 variants, a reverse genetics system for producing attenuated influenza virus NS1 variants, NS1 variant polypeptides, and polynucleotides encoding NS1 variant polypeptides, as well as methods of stimulating an immune response against influenza virus, and methods of interfering with influenza virus replication.

In order to further an understanding of the invention, a more detailed discussion is provided below regarding the production of compositions comprising nucleic acids, polypeptides, and attenuated influenza viruses and methods of using such compositions in the treatment or prevention of influenza virus infection.

A. Influenza Virus NS1 Variants

Attenuated influenza virus NS1 variants can be constructed by introducing at least one mutation as described herein into the eighth genomic segment from any pathogenic influenza virus strain or isolate. One or more mutations are introduced into the region of segment 8 coding for the NS1 protein, in particular, in the portions coding for the Src homology 2 (SH2) binding motif, Src homology 3 (SH3) binding motif 1, and/or SH3 binding motif 2. Mutations can include deletions, inversions, insertions or substitutions that impair PI3K activation and replication of the virus.

In certain embodiments, the attenuated influenza virus variant comprises a mutated segment 8 encoding an NS1 protein comprising one or more of the following mutations:

a mutation in the SH2 binding motif of NS1 at amino acid 89 (e.g., Y89F);

a mutation in the first SH3 binding motif of NS1 at prolines 164 and 167 (e.g., P164A and P167A);

a mutation in the second SH3 binding motif of NS1 at prolines 212, 213 and 216 (e.g., P212A, P213A, and P216A);

mutations in both the first and second SH3 binding motifs of NS1 (e.g., P164A, P167A, P212A, P213A, and P216A); or mutations in the SH2 binding motif and the first and second SH3 binding motifs of NS1 (e.g., Y89F, P164A, P167A, P212A, P213A, and P216A).

The foregoing numbering is relative to the reference sequence of NS1 from influenza A strain H1N1 Puerto Rico/8/34 (SEQ ID NO:2), and it is to be understood that the corresponding positions in NS1 derived from any type or strain of influenza virus are also intended to be encompassed by the present invention. In certain embodiments, the influenza virus variant encodes an NS1 polypeptide comprising a sequence selected from the group consisting of SEQ ID NOS: 18-47.

Recombinant techniques are readily used to clone a nucleic acid encoding an NS1 polypeptide, which can then be mutagenized in vitro by the replacement of the appropriate nucleotides to result in the desired amino acid changes. Such a change can include as little as one nucleotide, effecting a change in a single amino acid, or can encompass several nucleotide changes. Mutants can be produced by standard methods of site-directed mutagenesis. The mutations can be effected using a mismatched primer which hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, Methods Enzymol. (1983) 100:468; Wu (Ed.), Meth. In Enzymol. Vol. 217, San Diego: Academic Press (1993); Kunkel (1985) Proc. Natl. Acad. Sci. USA, 82:488-492; all of which are incorporated herein by reference.

Attenuated influenza virus comprising one or more NS1 mutations can be by any method well know in the art, preferably through the use of reverse genetics. Reverse genetics uses RNA polymerase complexes isolated from influenza virus-infected cells to transcribe artificial influenza virus genome segments containing the mutation(s). The synthesized RNA segment(s) are incorporated into virus particles using a helper virus, and viruses containing the desired changes are then selected. Reverse genetics methods for influenza viruses are described, for example, in Enami, et al. (1990) Proc. Natl. Acad. Sci. 87:3802 3805; Enami and Palese (1991) J Virol 65:2711-13; Luytjes (1989) Cell 59:1107-13; and in U.S. Pat. Nos. 5,578,473, 6,974,686 and 7,037,707, all of which are incorporated herein by reference in their entireties.

Recently developed reverse-genetics systems, based entirely on cDNA, have allowed the manipulation of the influenza viral genome. See, e.g, Palese et., (1996) Proc. Natl. Acad. Sci. USA 93:11354; Neumann and Kawaoka (1999) Adv. Virus Res. 53:265; Neumann et al. (1999) Proc. Natl. Acad. Sci. USA 96:9345; Fodor et al. (1999) J. Virol. 73:9679, incorporated by reference in their entireties. In one technique, modified vRNA transcripts are transcribed in vitro from cDNA constructs in the presence of purified NP, PB1, PB2, and PA proteins. The resulting synthetic RNP is then transfected into cells previously infected with an influenza helper virus. This helper virus usually has a conditional growth defect, such as host range restriction or temperature sensitivity, which allows the subsequent selection of transfectant viruses. For example, host-range helper viruses have been successfully used to rescue synthetic NA and PB2 genes. See Enami, supra, and Subbarao (1993) J Virol 67:7223-28.

In preferred embodiments, an eight plasmid system is used to generate attenuated influenza viruses. See, e.g., Hoffmann et al. (2002) Vaccine 20, 3165-3170; Hoffmann et al. (2000) Proc. Natl. Acad. Sci. USA. 97:6108-6113; and U.S. Patent Publication No. 20040029251, incorporated herein by reference in their entireties. See also, U.S. Pat. No. 6,951,754 that describes eight plasmid dual promoter reverse genetic systems for the production of attenuated influenza viruses using a pol I-pol II system, incorporated herein by reference in its entirety.

Nucleic acids for construction of mutants can be prepared in many ways (e.g., by chemical synthesis, from genomic or cDNA libraries, from the virus itself, etc.) and can take various forms (e.g., single stranded, double stranded, vectors, etc.). Preferably, nucleic acids are prepared in substantially pure form (i.e., substantially free from other host cell or non host cell nucleic acids).

For example, nucleic acids can be obtained by screening cDNA and/or genomic libraries from cells infected with virus, or by deriving the gene from a vector known to include the same. For example, polynucleotides of interest can be isolated from a genomic library derived from viral RNA from an infected individual. Alternatively, influenza virus nucleic acids can be isolated from infected humans or other mammals or from biological samples (e.g., nasal, nasopharyngeal, throat, or conjunctival secretions, blood, or anal swabs) collected from infected individuals.

Representative sequences from influenza isolates found in various species of birds and mammals are listed herein. In particular, representative sequences of segment 8 and the NS1 protein from influenza A viruses are known and are presented in FIGS. 9-14. Additional representative influenza A sequences are A/Puerto Rico/8/34 (H1N1) segment 8, GenBank Accession No. NC_002020; A/Udorn/72 (H3N2) segment 8, GenBank Accession No. CY009640; A/Thailand/676/2005 (H5N1) nonstructural protein 2 and nonstructural protein 1 genes, GenBank Accession No. DQ360842; A/Viet Nam/1194/2004 (H5N1) nonstructural protein 2 and nonstructural protein 1 (NS) gene, GenBank Accession No. AY651552; A/Hong Kong/97/98 (H5N1) nonstructural protein NS1 and nuclear export protein NS2 (NS) gene, GenBank Accession No. AF256188; and A/Netherlands/033/03 (H7N7) non-structural protein gene, GenBank Accession No. AY342423. See also Ferguson et al. (2003) Nature 422: 428-433; Lin et al. (2000) Proc. Natl. Acad. Sci. U.S.A. 97, 9654-9658; Nguyen et al. (2005) J. Virol. 79:4201-4212; Ha et al. (2002) EMBO J. 21:865-875; and Chan et al. (2004) J. Microbiol. Immunol. Infect. 37:135-144; for sequence comparisons of influenza virus subtypes from different species.

Any of these sequences, as well as variants thereof that can be used to produce attenuated influenza NS1 variants, will find use in the present methods. Thus, the invention includes variants of the above sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto.

Oligonucleotides for use in mutagenesis or nucleic acid amplification are derived from these sequences and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al., *Tetrahedron* (1992) 48:2223-2311; and Applied Biosystems User Bulletin No. 13 (1 Apr. 1987). Other chemical synthesis methods include, for example, the phosphotriester method described by Narang et al., *Meth. Enzymol.* (1979) 68:90 and the phosphodiester method disclosed by Brown et al., *Meth. Enzymol.* (1979) 68:109.

Additionally, nucleic acid can be obtained directly from the influenza virus in question. Several members of the influenza family of viruses are available from the ATCC as follows: influenza A equine/human reassortant (ATCC Accession No. VR-2070); influenza A swine H1N1 (ATCC Accession No. VR-99); influenza A human H1N1 (ATCC Accession No. VR-98); influenza A human H3N2 (ATCC Accession No. VR-547); influenza A human H3N2 (ATCC Accession No. VR-544); influenza A (ATCC Accession No. VR-95); influenza A (ATCC Accession No. VR-96); influenza A (ATCC Accession No. VR-97); influenza A (ATCC Accession No. VR-219); influenza A (ATCC Accession No. VR-317); influenza A (ATCC Accession No. VR-333); influenza A (ATCC Accession No. VR-546); influenza A (ATCC Accession No. VR-776); influenza A (ATCC Accession No. VR-777); influenza A (ATCC Accession No. VR-897); influenza A (ATCC Accession No. VR-297); influenza A (ATCC Accession No. VR-810); influenza A (ATCC Accession No. VR-822); influenza A (ATCC Accession No. VR-1520); influenza A (ATCC Accession No. VR-825); influenza A (ATCC Accession No. VR-1331); influenza B (ATCC Accession No. VR-101); influenza B (ATCC Accession No. VR-102); influenza B (ATCC Accession No. VR-103); influenza B (ATCC Accession No. VR-295); influenza B (ATCC Accession No. VR-523); influenza B (ATCC Accession No. VR-786); influenza B (ATCC Accession No. VR-787); influenza B (ATCC Accession No. VR-788); influenza B (ATCC Accession No. VR-789); influenza B (ATCC Accession No. VR-790); influenza B (ATCC Accession No. VR-823); and influenza B (ATCC Accession No. VR-1535).

Alternatively, influenza virus nucleic acid can be isolated from infected birds, humans, pigs, horses, cats, seals or other mammals, as described in e.g., Fouchier et al. (2000) J. Clin. Microbiol. 38:4096-4101. Once obtained, the virus can be propagated using known techniques, such as described in Mochalova et al. (2003) Virology 313:473-480; Lin et al. (1997) Virology 233:402-410; Hardy et al. (1995) Virology 211:302-306; Hinshaw et al. (1978) J. Gen. Virol. 41:115-127. Generally, influenza viruses are grown in embryonated chicken eggs or mammalian cells, such as Madin-Darby canine kidney (MDCK) cells, Madin Darby bovine kidney (MDBK) cells, or African green monkey kidney (Vero) cells.

An amplification method such as PCR can be used to amplify polynucleotides encoding NS1 from either influenza virus genomic RNA or cDNA encoding therefor. Alternatively, polynucleotides can be synthesized in the laboratory, for example, using an automatic synthesizer. The nucleotide sequence can be designed with the appropriate codons for the particular amino acid sequence desired. In general, one will select preferred codons for the intended host in which the sequence will be expressed. The complete sequence of the polynucleotide of interest can be assembled from overlapping oligonucleotides prepared by standard methods and assembled into a complete coding sequence. See, e.g., Edge (1981) Nature 292:756; Nambair et al. (1984) Science 223:1299; Jay et al. (1984). J. Biol. Chem. 259:6311; Stemmer et al. (1995) Gene 164:49-53. The polynucleotides can be RNA or single- or double-stranded DNA. Preferably, the polynucleotides are isolated free of other components, such as proteins and lipids.

Thus, particular nucleotide sequences can be obtained from vectors harboring the desired sequences or synthesized completely or in part using various oligonucleotide synthesis techniques known in the art, such as site-directed mutagenesis and polymerase chain reaction (PCR) techniques where appropriate. See, e.g., Sambrook, supra. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR. See, e.g., Jayaraman et al. (1991) Proc. Natl. Acad. Sci. USA 88:4084-4088. Additionally, oligonucleotide directed synthesis (Jones et al. (1986) Nature 54:75-82), oligonucleotide directed mutagenesis of pre-existing nucleotide regions (Riechmann et al. (1988) Nature 332:323-327 and Verhoeyen et al. (1988) Science 239:1534-1536), and enzymatic filling-in of gapped oligonucleotides using $T_4$ DNA polymerase (Queen et al. (1989) Proc. Natl. Acad. Sci. USA 86:10029-10033) can be used to produce modified molecules.

Mutants can be tested for impaired PI3K activation, reduced protein synthesis, and attenuated viral replication (see, e.g., Examples 6-8 for a description of assays). For example, the effects of mutations on PI3K activation can be determined by measuring PI3K phosphorylation of Akt and binding of NS1 variants to the SH2 and SH3 domains of the p85 subunit of PI3K (see Example 6). The replication efficiency of influenza virus mutants may be determined, for example, by measuring plaque size in MDCK cells or by measuring virus titers over multiple growth cycles (see Example 7). The effect of mutations on protein synthesis can be determined by Western blot assays (see Example 8).

B. Production of Polypeptides

NS1 polypeptides described herein can be prepared in any suitable manner (e.g. recombinant expression, purification from cell culture, chemical synthesis, etc.) and in various forms (e.g. native, mutant, fusions, etc.). Such polypeptides include naturally-occurring polypeptides, recombinantly produced polypeptides, synthetically produced polypeptides, or polypeptides produced by a combination of these methods. Means for preparing such polypeptides are well understood in the art. Polypeptides are preferably prepared in substantially pure form (i.e. substantially free from other host cell or non host cell proteins).

Polypeptides can be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides: Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptides of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Alternatively, the above-described NS1 polypeptides can be produced recombinantly. Once coding sequences for the desired proteins have been isolated or synthesized, they can be cloned into any suitable vector or replicon for expression. Numerous cloning vectors are known to those of skill in the art, and the selection of an appropriate cloning vector is a matter of choice. A variety of bacterial, yeast, plant, mammalian and insect expression systems are available in the art and any such expression system can be used (e.g., see Examples 1 and 2 for construction of exemplary expression cassettes for expression in yeast and insect cells, respectively). Optionally, a polynucleotide encoding these proteins can be translated in a cell-free translation system. Such methods are well known in the art.

Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, DNA Cloning: Vols. I & II, supra; Sambrook et al., supra; B. Perbal, supra.

Insect cell expression systems, such as baculovirus systems, can also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego Calif. ("MaxBac" kit).

Plant expression systems can also be used to produce the immunogenic proteins. Generally, such systems use virusbased vectors to transfect plant cells with heterologous genes. For a description of such systems see, e.g., Porta et al., Mol. Biotech. (1996) 5:209-221; and Hackiand et al., Arch. Virol. (1994) 139:1-22.

Viral systems, such as a vaccinia based infection/transfection system, as described in Tomei et al., J. Virol. (1993) 67:4017-4026 and Selby et al., J. Gen. Virol. (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired immunogenic polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the tpa leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the immunogenic polypeptides. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; Nucleic Acid Hybridization, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli*, *Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the proteins of the present invention are produced by growing host cells transformed by an expression vector described above under conditions whereby the protein of interest is expressed. The selection of the appropriate growth conditions is within the skill of the art. The cells are then disrupted, using chemical, physical or mechanical means, which lyse the cells yet keep the influenza virus polypeptides substantially intact. Intracellular proteins can also be obtained by removing components from the cell wall or membrane, e.g., by the use of detergents or organic solvents, such that leakage of the immunogenic polypeptides occurs. Such methods are known to those of skill in the art and are described in, e.g., Protein Purification Applications: A Practical Approach, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pretreatment used.

Following disruption of the cells, cellular debris is removed, generally by centrifugation, and the intracellularly produced NS1 polypeptide is further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular NS1 polypeptide of the present invention involves affinity purification, such as by immunoaffinity chromatography using specific antibodies. The choice of a suitable affinity resin is within the skill in the art. After affinity purification, the NS1 polypeptide can be further purified using conventional techniques well known in the art, such as by any of the techniques described above.

It may be desirable to produce multiple polypeptides simultaneously (e.g., structural and/or nonstructural proteins from one or more influenza viral strains or viral polypeptides in combination with polypeptide adjuvants). Production of two or more different polypeptides can readily be accomplished by e.g., co-transfecting host cells with constructs encoding the different polypeptides. Co-transfection can be accomplished either in trans or cis, i.e., by using separate vectors or by using a single vector encoding the polypeptides. If a single vector is used, expression of the polypeptides can be driven by a single set of control elements or, alternatively, the sequences coding for the polypeptides can be present on the vector in individual expression cassettes, regulated by individual control elements.

C. Nucleic Acid Delivery

Delivery of nucleic acids, described herein, encoding NS1 variant polypeptides and/or attenuated influenza virus variants, and optionally other viral polypeptides (e.g., structural and nonstructural proteins), can be used to elicit an immune response in a subject and/or block influenza virus replication, for example, to treat or prevent influenza virus infection.

Nucleic acids described herein can be inserted into an expression vector to create an expression cassette capable of producing the viral polypeptides and/or attenuated virus in a suitable host cell. The ability of constructs to produce attenuated influenza virus can be empirically determined (e.g, see Example 7 describing plaque assay and measurement of viral titers).

Expression cassettes typically include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., EMPO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Once complete, the constructs are used for nucleic acid immunization or the like using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, BioTechniques (1989) 7:980-990; Miller, A. D., Human Gene Therapy (1990) 1:5-14; Scarpa et al., Virology (1991) 180:849-852; Burns et al., Proc. Natl.

Acad. Sci. USA (1993) 90:8033-8037; and Boris-Lawrie and Temin, Cur. Opin. Genet. Develop. (1993) 3:102-109).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Additional viral vectors which will find use for delivering the nucleic acid molecules comprising the influenza virus sequences of interest include those derived from the pox family of viruses, including vaccinia virus and avian poxvirus. By way of example, vaccinia virus recombinants comprising influenza virus sequences can be constructed as follows. DNA comprising a particular influenza virus sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with. respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos. WO 02/099035, WO 02/080982, WO 01/81609, and WO 00/61772; herein incorporated by reference in their entireties.

A vaccinia based infection/transfection system can be conveniently used to provide for inducible, transient expression of the coding sequences of interest (for example, an NS1 variant expression cassette) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

The synthetic expression cassette of interest can also be delivered without a viral vector. For example, the synthetic expression cassette can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, Biochim. Biophys. Acta. (1991.) 1097:1-17; Straubinger et al., in Methods of Enzymology (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., Proc. Natl. Acad. Sci. USA (1987) 84:7413-7416); mRNA (Malone et al., Proc. Natl. Acad. Sci. USA (1989) 86:6077-6081); and purified transcription factors (Debs et al., J. Biol. Chem. (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., Proc. Natl. Acad. Sci. USA (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials.

Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., Proc. Natl. Acad. Sci. USA (1978) 75:4194-4198; Papahadjopoulos et al., Biochim. Biophys. Acta (1975) 394:483; Wilson et al., Cell (1979) 17:77); Deamer and Bangham, Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); Enoch and Strittmatter, Proc. Natl. Acad. Sci. USA (1979) 76:145); Fraley et al., J. Biol. Chem. (1980) 255:10431; Szoka and Papahadjopoulos, Proc. Natl. Acad. Sci. USA (1978) 75:145; and Schaefer-Ridder et al., Science (1982) 215:166.

The DNA and/or protein antigen(s) can also be delivered in cochleate lipid compositions similar to those described by Papahadjopoulos et al., Biochem. Biophys. Acta. (1975) 394: 483-491. See, also, U.S. Pat. Nos. 4,663,161 and 4,871,488.

The expression cassette of interest may also be encapsulated, adsorbed to, or associated with, particulate carriers. Such carriers present multiple copies-of a selected antigen to the immune system and promote migration, trapping and retention of antigens in local lymph nodes. The particles can be taken up by profession antigen presenting cells such as macrophages and dendritic cells, and/or can enhance antigen presentation through other mechanisms such as stimulation of cytokine release. Examples of particulate carriers include those derived from polymethyl methacrylate polymers, as well as microparticles derived from poly(lactides) and poly (lactide-co-glycolides), known as PLG. See, e.g., Jeffery et al., Pharm. Res. (1993) 10:362-368; McGee J. P., et al., J. Microencapsul. 14(2):197-210, 1997; O'Hagan D. T., et al., Vaccine 11(2):149-54, 1993.

Furthermore, other particulate systems and polymers can be used for the in vivo or ex vivo delivery of the gene of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371, 015; and 5,478,744. Also, needle-less injection systems can be used (Davis, H. L., et al, Vaccine 12:1503-1509, 1994; Bioject, Inc., Portland, Oreg.).

Recombinant vectors carrying a synthetic expression cassette of the present invention are formulated into compositions for delivery to a vertebrate subject. These compositions may either be prophylactic (to prevent infection) or therapeutic (to treat disease after infection). The compositions will comprise a "therapeutically effective amount" of the gene(s) of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, surfactants and the like, may be present in such vehicles. Certain facilitators of immunogenicity or of nucleic acid uptake and/ or expression can also be included in the compositions or coadministered, such as, but not limited to, bupivacaine, cardiotoxin and sucrose.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) (with or without the corresponding antigen) in liposomes, and direct microinjection of the DNA into nuclei.

Direct delivery of synthetic expression cassette compositions in vivo will generally be accomplished with or without viral vectors, as described above, by injection using either a conventional syringe, needless devices such as Bioject™ or a gene gun, such as the Accell™ gene delivery system (PowderMed Ltd, Oxford, England). The constructs can be delivered (e.g., injected) either subcutaneously, epidermally, intradermally, intramuscularly, intravenous, intramucosally (such as nasally, rectally and vaginally), intraperitoneally or orally. Delivery of DNA into cells of the epidermis is particularly preferred as this mode of administration provides access to skin-associated lymphoid cells and provides for a transient presence of DNA in the recipient. Other modes of administration include oral ingestion and pulmonary administration, suppositories, needle-less injection, transcutaneous, topical, and transdermal applications. Dosage treatment may be a single dose schedule or a multiple dose schedule.

D. Anti-Viral Compositions

The attenuated influenza virus variants, as well as attenuated influenza virus that has been subsequently inactivated, nucleic acids, and/or polypeptides described herein can be formulated into compositions for delivery to subjects for either inhibiting infection, or for enhancing an immune response to influenza virus. Production of live attenuated virus vaccine formulations is accomplished using conventional methods involving propagation of the attenuated virus in cell culture or in the allantois of the chick embryo followed by purification. Generally, influenza viruses are grown in embryonated chicken eggs or mammalian cells, such as Madin-Darby canine kidney (MDCK) cells, Madin Darby bovine kidney (MDBK) cells, or African green monkey kidney (Vero) cells, using known techniques. See, e.g., Mochalova et al. (2003) Virology 313:473-480; Lin et al. (1997) Virology 233:402-410; Hardy et al. (1995) Virology 211:302-306; Hinshaw et al. (1978) J. Gen. Virol. 41:115-127.

Methods of purification are known in the art and may include one or more of, for instance, gradient centrifugation, ultracentrifugation, zonal ultracentrifugation, continuous-flow ultracentrifugation and chromatography, such as ion exchange chromatography, size exclusion chromatography, and liquid affinity chromatography, polyethylene glycol or ammonium sulfate precipitation.

In another embodiment, inactivated vaccine formulations may be prepared using conventional techniques to "kill" the attenuated viruses. Inactivated vaccines are "dead" in the sense that their infectivity has been destroyed. Ideally, the infectivity of the virus is destroyed without affecting is immunogenicity. In order to prepare inactivated vaccines, the attenuated virus is grown and purified as described above. The purified virus is then inactivated using one of several methods known in the art. Such methods include both chemical or physical means. Chemical means for inactivating an influenza virus include treatment of the virus with an effective amount of one or more of the following agents: detergents, formaldehyde, formalin, β-propiolactone, or UV light. Other methods of viral inactivation are known in the art, such as for example binary ethylamine, acetyl ethyleneimine, or gamma irradiation.

Compositions of the invention may comprise or be co-administered with a non-influenza antigen or combination of antigens, such as with a combination influenza vaccine. Methods of preparing such formulations are described in, e.g., *Remington's Pharmaceutical Sciences*, Mack Publishing Company, Easton, Pa., 18 Edition, 1990. The compositions of the present invention can be prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

If used to modulate an immune response, additional adjuvants which enhance the effectiveness of the composition may also be added to the formulation. Adjuvants may include for example, muramyl dipeptides, pyridine, aluminum hydroxide, dimethyldioctadecyl ammonium bromide (DDA), oils, oil-in-water emulsions, saponins, cytokines, and other substances known in the art.

Influenza polypeptides may also be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

Influenza polypeptides may be used in their native form or their functional group content may be modified by, for example, succinylation of lysine residues or reaction with Cys-thiolactone. A sulfhydryl group may also be incorporated by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides. Other suitable carriers include VP6 polypeptides of rotaviruses, or functional fragments thereof, as disclosed in U.S. Pat. No. 5,071,651. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Methods of coupling peptides to proteins or cells are known to those of skill in the art.

Furthermore, influenza molecules (or complexes thereof) may be formulated into compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Injectable formulations will contain a "pharmaceutically effective amount" of the active ingredient, that is, an amount capable of achieving the desired response in a subject to which the composition is administered. In the treatment and prevention of influenza infection, for example, a "pharmaceutically effective amount" would preferably be an amount which reduces or ameliorates the symptoms of flu. The exact amount is readily determined by one skilled in the art using standard tests. The influenza virus variant, nucleic acid, and/or polypeptide will typically range from about 1% to about 95% (w/w) of the composition, or even higher or lower if appropriate. With the present formulations, 1 μg to 2 mg, such as 100 μg to 1 mg, of active ingredient per ml of injected solution should be adequate to treat or prevent infection when a dose of 1 to 3 ml per subject is administered. If an adjuvant is used to enhance the immune response to co-delivered influenza antigen or combination of antigens, the amount of adjuvant delivered will generally be in the range of 2 ng to 5 mg, more generally 5 ng to 500 ng, for example 10 ng to 250 ng, or any amount within these stated ranges. The quantity to be administered depends on the subject to be treated, the capacity of the subject's immune system to synthesize antibodies, and the degree of protection desired. Effective dosages can be readily established by one of ordinary skill in the art through routine trials establishing dose response curves.

The composition can be administered parenterally, e.g., by intratracheal, intramuscular, subcutaneous, intraperitoneal, intravenous injection, or by delivery directly to the lungs, such as through aerosol administration. The subject is administered at least one dose of the composition. Moreover, the subject may be administered as many doses as is required to bring about the desired biological effect.

Additional formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and HYTREL copolymers, swellable polymers such as hydrogels, resorbable polymers such as collagen and certain polyacids or polyesters such as those used to make resorbable sutures, polyphosphazenes, alginate, microparticles, gelatin nanospheres, chitosan nanoparticles, and the like. The influenza virus variants, nucleic acids, and/or polypeptides described herein can also be delivered using implanted mini-pumps, well known in the art.

E. Administration

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal (See e.g. WO99/27961) or transcutaneous (See e.g. WO02/074244 and WO02/064162), intranasal (See e.g. WO03/028760), ocular, aural, pulmonary or other mucosal administration. Immunogenic compositions can also be administered topically by direct transfer to the surface of the skin. Topical administration can be accomplished without utilizing any devices, or by contacting naked skin with the immunogenic composition utilizing a bandage or a bandage-like device (see, e.g., U.S. Pat. No. 6,348,450).

Preferably the mode of administration is parenteral, mucosal or a combination of mucosal and parenteral immunizations. Even more preferably, the mode of administration is parenteral, mucosal or a combination of mucosal and parenteral immunizations in a total of 1-2 vaccinations 1-3 weeks apart. Preferably the route of administration includes but is not limited to oral delivery, intra-muscular delivery and a combination of oral and intra-muscular delivery.

In one embodiment, the method for treating an infection by an influenza virus, comprises mucosally administering to a subject in need thereof a first immunogenic composition comprising one or more influenza virus antigens followed by parenterally administering a therapeutically effective amount of a second immunogenic composition comprising one or more influenza virus antigens.

The immunogenic composition may be used to elicit systemic and/or mucosal immunity, preferably to elicit an enhanced systemic and/or mucosal immunity. Preferably the immune response is characterized by the induction of a serum IgG and/or intestinal IgA immune response.

As noted above, prime-boost methods can be employed where one or more gene delivery vectors, and/or attenuated virus variants, and/or polypeptide antigens are delivered in a "priming" step and, subsequently, one or more second gene delivery vectors, and/or attenuated virus variants, and/or polypeptide antigens are delivered in a "boosting" step. In certain embodiments, priming and boosting with one or more gene delivery vectors, attenuated virus variants, and/or polypeptide antigens described herein is followed by additional boosting with one or more polypeptide-containing compositions (e.g., polypeptides comprising influenza virus antigens).

In any method involving co-administration, the various compositions can be delivered in any order. Thus, in embodiments including delivery of multiple different compositions or molecules, the attenuated influenza virus need not be all delivered before immunogenic polypeptides. For example, the priming step may include delivery of one or more polypeptides and the boosting comprises delivery of one or more attenuated influenza virus variants and/or nucleic acids. Multiple administrations of attenuated influenza virus can be followed by multiple administrations of nucleic acids or polypeptides. Administrations can be performed in any order. Thus, one or more of the gene delivery vectors or attenuated influenza virus variants described herein and one or more of the polypeptides described herein can be co-administered in any order and via any administration route. Therefore, any combination of attenuated influenza virus variant, polynucleotides, and polypeptides described herein can be used to elicit an immune reaction.

Dosage Regime

Dosage treatment can be according to a single dose schedule or a multiple dose schedule. Multiple doses may be used in a primary immunization schedule and/or in a booster immunization schedule. In a multiple dose schedule, the various doses may be given by the same or different routes, e.g. a parenteral prime and mucosal boost, a mucosal prime and parenteral boost, etc.

Preferably the dosage regime enhances the avidity of the antibody response leading to antibodies with a neutralizing characteristic. An in-vitro neutralization assay may be used to test for neutralizing antibodies (see for example Asanaka et al (2005) J of Virology 102: 10327; Wobus et al (2004) PLOS Biology 2(12); e432; and Dubekti et al (2002) J Medical Virology 66: 400).

F. Tests to Determine the Efficacy of an Immune Response

One way of assessing efficacy of therapeutic treatment involves monitoring infection after administration of a composition of the invention. One way of assessing efficacy of prophylactic treatment involves monitoring immune responses against the antigens in the compositions of the invention after administration of the composition.

Another way of assessing the immunogenicity of the component proteins of the immunogenic compositions of the present invention is to express the proteins recombinantly and to screen patient sera or mucosal secretions by immunoblot. A positive reaction between the protein and the patient serum indicates that the patient has previously mounted an immune response to the protein in question-that is, the protein is an immunogen. This method may also be used to identify immunodominant proteins and/or epitopes.

Another way of checking efficacy of therapeutic treatment involves monitoring infection after administration of the compositions of the invention. One way of checking efficacy of prophylactic treatment involves monitoring immune responses both systemically (such as monitoring the level of IgG1 and IgG2a production) and mucosally (such as monitoring the level of IgA production) against the antigens in the compositions of the invention after administration of the composition. Typically, serum specific antibody responses are determined post-immunization but pre-challenge whereas mucosal specific antibody body responses are determined post-immunization and post-challenge. The immunogenic compositions of the present invention can be evaluated in in vitro and in vivo animal models prior to host, e.g., human, administration. Particularly useful mouse models include those in which intraperitoneal immunization is followed by either intraperitoneal challenge or intranasal challenge.

The efficacy of immunogenic compositions of the invention can also be determined in vivo by challenging animal models of infection, e.g., guinea pigs or mice or rhesus macaques, with the immunogenic compositions. The immunogenic compositions may or may not be derived from the same strains as the challenge strains. Preferably the immunogenic compositions are derivable from the same strains as the challenge strains.

In vivo efficacy models include but are not limited to: (i) A murine infection model using human strains; (ii) a murine disease model which is a murine model using a mouse-adapted strain, such as strains which are particularly virulent in mice and (iii) a primate model using human isolates. A human challenge model, which is supported by the NIH and Center for Disease Control (CDC) is also available (see for example, Lindesmith et al (2003) Nature Medicine 9: 548-553 and Journal of Virology (2005) 79: 2900).

The immune response may be one or both of a TH1 immune response and a TH2 response. The immune response may be an improved or an enhanced or an altered immune response. The immune response may be one or both of a systemic and a mucosal immune response. Preferably the immune response is an enhanced systemic and/or mucosal response.

An enhanced systemic and/or mucosal immunity is reflected in an enhanced TH1 and/or TH2 immune response. Preferably, the enhanced immune response includes an increase in the production of IgG1 and/or IgG2a and/or IgA. Preferably the mucosal immune response is a TH2 immune response. Preferably, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH1 immune response may include one or more of an increase in CTLs, an increase in one or more of the cytokines associated with a TH1 immune response (such as IL-2, IFNγ, and TNFβ), an increase in activated macrophages, an increase in NK activity, or an increase in the production of IgG2a. Preferably, the enhanced TH1 immune response will include an increase in IgG2a production.

Immunogenic compositions of the invention, in particular, immunogenic composition comprising one or more antigens of the present invention may be used either alone or in combination with other antigens optionally with an immunoregulatory agent capable of eliciting a Th1 and/or Th2 response.

The immunogenic compositions of the invention will preferably elicit both a cell mediated immune response as well as a humoral immune response in order to effectively address an infection. This immune response will preferably induce long lasting (e.g., neutralizing) antibodies and a cell mediated immunity that can quickly respond upon exposure to one or more infectious antigens. By way of example, evidence of neutralizing antibodies in patient blood samples is considered as a surrogate parameter for protection since their formation is of decisive importance for virus elimination in TBE infections (see Kaiser and Holzmann (2000) Infection 28; 78-84).

G. Use of the Immunogenic Compositions as Medicaments

The invention also provides a composition of the invention for use as a medicament. The medicament is preferably able to raise an immune response in a mammal (i.e. it is an immunogenic composition) and is more preferably a vaccine. The invention also provides the use of the compositions of the invention in the manufacture of a medicament for raising an immune response in a mammal. The medicament is preferably a vaccine. Preferably the vaccine is used to prevent and/or treat an influenza infection.

The invention provides methods for inducing or increasing an immune response using the compositions described above. The immune response is preferably protective and can include antibodies and/or cell-mediated immunity (including systemic and mucosal immunity). Immune responses include booster responses.

The invention also provides a method for raising an immune response in a mammal comprising the step of administering an effective amount of a composition of the invention. The immune response is preferably protective and preferably involves antibodies and/or cell-mediated immunity. Preferably, the immune response includes one or both of a TH1 immune response and a TH2 immune response. The method may raise a booster response.

The mammal is preferably a human. Target groups for the immunogenic compositions (e.g., vaccines) of the present invention include:

Adults and children, including but not limited to the following:

Transplant and immunocompromised individuals;

Food handlers;

Healthcare workers such as but not limited to Hospital and Nursing home personnel;

Day care children;

Travelers including cruise ship travelers;

Military personnel; and

Pediatric and/or elderly populations.

H. Kits

The invention also provides kits comprising one or more containers of compositions of the invention. Compositions can be in liquid form or can be lyophilized, as can individual antigens. Suitable containers for the compositions include, for example, bottles, vials, syringes, and test tubes. Containers can be formed from a variety of materials, including glass or plastic. A container may have a sterile access port (for example, the container may be an intravenous solution bag or a vial having a stopper pierceable by a hypodermic injection needle).

The kit can further comprise a second container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery device. The kit may further include a third component comprising an adjuvant.

The kit can also comprise a package insert containing written instructions for methods of inducing immunity or for treating infections. The package insert can be an unapproved draft package insert or can be a package insert approved by the Food and Drug Administration (FDA) or other regulatory body.

The invention also provides a delivery device pre-filled with the immunogenic compositions of the invention.

3. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Materials and Methods

A. Cells and Virus

A549 cells (human lung carcinoma cells) and 293T (human embryonic kidney) cells were maintained in Dulbecco's modified Eagle's medium (DMEM) (Invitrogen) containing 10% fetal bovine serum (FBS). Madin-Darby canine kidney (MDCK) cells were cultivated in minimal essential medium (MEM) (Invitrogen) supplemented with 10% FBS. Influenza A/PR/8/34 (H1N1) (PR8) was propagated at 37° C. in 11-day-old embryonated chicken eggs. Virus titers were determined on MDCK cells by plaque assay.

B. Antibodies

Rabbit monoclonal phospho-Akt (Ser473) antibody, rabbit polyclonal Akt antibody and horseradish peroxidase (HRP)-conjugated anti-rabbit IgG were purchased from Cell Signaling Technology. Rabbit polyclonal PI3K p85 antibody was purchased from Upstate Biotechnology, Inc. Monoclonal NP antibody was purchased from Serotec and used in immunofluorescence staining analysis. Alkaline Phosphotase (AP)-conjugated anti rabbit IgG and Cy3-conjugated anti mouse IgG were purchased from Jackson ImmunoResearch Lab.

Rabbit antisera against NP (06-3/4) and M1 (06-1/2) were described previously (Submitted manuscript). Rabbit antiserum against NS1 (05-21/22) was generated by immunization of rabbits with purified His-NS1 protein. Briefly, NS1 cDNA was PCR amplified by using pHW198-NS (Hoffmann et al. (2002) *Vaccine* 20, 3165-3170) as a DNA template and primers XhoI-NS-27-Fw (SEQ ID NO:48): 5'-ATC GCT CGA GAT GGA TCC AAA CAC TGT GTC A-3'/EcoRI-NS-718-Bw (SEQ ID NO:49): 5'-AGC GGA ATT CAA ACT TCT GAC CTA ATT GTTC-3'. The PCR product was digested by XhoI and EcoRI and inserted into the XhoI/EcoRI sites of pRSETA vector (Invitrogen), His-tagged proteins were induced in *Escherichia coli* BL21 cells by isopropyl-β-D-(−) thiogalactopyranoside and purified by Ni-NTA agarose beads (Qiagen) under denaturing conditions according to the manufacturer's protocol. Purified proteins were dialyzed against phosphate-buffered saline (PBS). Each rabbit was subcutaneously injected with 500 μg of antigen mixed with an equal volume of Freund's complete adjuvant (Sigma) followed by two injections with 250 μg of antigen mixed with an equal volume of Freund's incomplete adjuvant at 4 weeks intervals. Rabbits were bled 2 weeks after the last injection. Antiserum was characterized, aliquoted and stored at −20° C.

C. Plasmid Construction

Mutations in the NS1 protein coding sequence were introduced into the plasmid pHW198-NS (Hoffmann et al., supra). Plasmid pHW198-NS-Y89F, encoding a mutant NS1 with tyrosine at position 89 replaced by phenylalanine (Y89F), and plasmid pHW-NS-P212-216A, encoding a mutant NS1 with prolines at positions 212, 213 and 216 replaced by alanines (P212-216A), were generated by site-directed mutagenesis using the following forward (Fw) and backwards (Bw) primers: NS1-Y89F-Fw (SEQ ID NO:50): 5'-GGC CTC TGT ACC TGC GTC TAG ATT TCT AAC TGA CAT GAC TC-3'/ NS1-Y89F-Bw (SEQ ID NO:51): 5'-GAG TCA TGT CAG TTA GAA ATC TAG ACG CAG GTA CAG AGG CC-3' and NS-P212-216A-Fw (SEQ ID NO:52): 5'-ATG AGA ATG GGA GAT CTG CAC TCA CTG CAA AAC AGA AAC G-3'/NS-P212-216A-Bw (SEQ ID NO:53): 5'-CGT TTC TGT TTT GCA GTG AGT GCA GAT CTC CCA TTC TCA T-3', respectively. To introduce mutations on NS1 with prolines at 164 and 167 replaced by alanines (P1164-167A) in the background of pHW-NS P212-216A, pHW-NS P212-216A was digested by MfeI and BbvCI, the 48 nucleotide sequence was replaced by oligo pair (Fw (SEQ ID NO:54): 5'-AAT TGT TGG CGA AAT TTC TGC ATT GGC TTC TCT TGC AGG ACA TAC TGC-3'/Bw (SEQ ID NO:55): 5'-TCA GCA GTA TGT CCT GCA AGA GAA GCC AAT GCA GAA ATT TCG CCA AC-3'), resulting in the plasmid pHWNS-SH3-PP1/2mt. To combine all the mutations into one plasmid, pHWNS-SH3-PP1/2mt was digested by BamHI and XcmI, the 324 nucleotide fragment was replaced with 324 nucleotide fragment derived from pHW198-NS-Y89F, resulting in the plasmid pHW-NS-SH2/SH3mt, which encodes NS1 protein with mutations at Y89F, P164-167A and P212-216A.

To generate CMV promoter-controlled wt NS1 expression plasmids, the wt NS1 was amplified from pHW198-NS by PCR (primers NheI-NS-27 Fw (SEQ ID NO:56): 5'-ACG TGC TAG CAT GGA TCC AAA CAC TGT GTCA-3', XhoI-NS-864 Bw (SEQ ID NO:57): 5'-CTG ACT CGA GCT AAA TAA GCT GAA ACG AGA A-3') and was inserted into pcDNA3.1(−) at sites NheI/XhoI, resulting plasmids pcDNA-NS. All the mutations were confirmed by restriction enzyme digestions followed by DNA sequencing.

D. Generation of NS1 Mutant Virus

NS1 mutant virus was generated by using an 8-plasmid reverse genetics system described by Hoffmann et al. (Proc. Natl. Acad. Sci. U. S. A. 97, 6108-6113). Plasmids pHW191-PB2, pHW192-PB1, pHW193-PA, pHW194-HA, pHW195-NP, pHW196-NA, pHW197-M and pHW198-NS (Hoffmann et al. (2002), supra) were kindly obtained from Dr. E. Hoffmann and Dr. R. G. Webster (St. Jude Children's Research Hospital, Memphis, Tenn.). The cocultured MDCK and 293T cells (0.3×10$^6$ cells per well of 6-well plate each) were transfected with 8 plasmids (pHW191-PB2, pHW192-PB1, pHW193-PA, pHW194-HA, pHW195-NP, pHW196-NA, pHW197-M and pHW-NS-SH2/SH3mt) using TransIT LT-1 (Mirus) according to the manufacturer's instructions. 2 μl of TransIT LT-1 per 1 μg of DNA was mixed, incubated at room temperature for 45 minutes, and added to the cells. Six hours later, the DNA-transfection mixture was replaced by 1 ml of Opti-MEM (Invitrogen). Twenty-four hours later, 1 ml of Opti-MEM containing TPCK-trypsin (1 μg/ml) was added to the cells. Seventy-two hours later, the supernatant was harvested and passaged once on MDCK cells. Mutant virus PR8-SH2/SH3mt was characterized by sequencing of RT-PCR product derived from the NS segment. The mutant virus was then propagated in 10-day-old embryonated chicken eggs.

E. Western Blotting Analysis

About 1×10⁶ A549 cells were plated into 35 mm dishes and were mock infected or infected with influenza viruses at a determined multiplicity of infection (MOI). At the indicated times, cell monolayers were washed with PBS and lysed with RIPA buffer (0.5 M Tris pH 8.0; 0.15 M NaCl; 0.1% sodium dodecyl sulfate; 1% NP-40; 1% deoxycholic acid) containing 1×COMPLETE protease inhibitor cocktail (Roche). The lysates were collected, homogenized by passage several times through a 1 ml syringe with a 22 gauge needle and incubated on ice for 10 minutes. Lysates were cleared by centrifugation for 5 minutes at 12,000×g. The supernatant was analyzed for total protein content using a Bradford assay (Bio-Rad). Thirty μg of total protein was resolved on sodium dodecyl sulfate—10% polyacrylamide gels (SDS-PAGE), and transferred onto nitrocellulose membranes (Bio-Rad). Membranes were blocked for nonspecific binding with Tris buffered saline (TBS) (0.1M Tris pH7.6; 0.9% NaCl) containing 0.1% Tween-20 and 10% skim milk for 1 hour at room temperature. For examination of phosphorylated Akt or total Akt, a primary antibody either rabbit monoclonal phospho-Akt (Ser473) (1:1000) or rabbit polyclonal Akt antibody (1:1000) was applied overnight at 4° C. A secondary antibody of HRP-conjugated anti-rabbit IgG (1:3,000) was then added at room temperature for 1 hour. The immunoblots were visualized with an enhanced chemiluminescence reagent using the ECL ADVANCE Western blotting detection kit (GE Healthcare). For examination of viral proteins, cell lysates were probed with rabbit polyclonal NP (1:2000), M1 (1:2000) or NS1 (1:2000) antibody followed by an incubation with AP-conjugated anti rabbit IgG (1:10,000). The immunoblots were then visualized by incubating with BCIB/NBT premix solution (Sigma).

F. Co-Immunoprecipitation Analysis

A549 cells were mock infected or wt PR8 virus infected at an MOI of 1 PFU/cell. At 6 h.p.i., cell lysates were prepared as described above. Five μl of anti-PI3K p85 or normal rabbit serum was pre-incubated with 60 μl (30 μl packed beads) of washed protein A sepharose beads (GE Healthcare) slurry and incubated at 4° C. for 1 hour. Beads were then washed 3 times with ice-cold PBS. To 500 μg (1 μg/μl) of cell lysates, add antibody-protein A complex and incubated at 4° C. for overnight. Following extensive washes with RIPA buffer, the resulting precipitates were resuspended in 60 μl of Laemmli sample buffer and boiled for 5 minutes. Ten μl of supernatant was subjected to SDS-PAGE. Western blotting was performed by using rabbit antiserum against NS1 as described above.

G. Transfection and Electroporation 293T cells were seeded in 10-cm dishes at a density of 8×10⁶/well. Five μg of pcDNA3.1(−) or pcDNA-NS was transfected using LIPOFECTAMINE cationic lipid reagent (Invitrogen). Forty-eight hours later, cell lysates were harvested as described above and subjected to GST pull down assay.

Five million of A549 cells were resuspended in 400 μl of PBS. Thirty μg of pcDNA3.1(−) or pcDNA-NS was electroporated into the cells by using a GENE PULSER II electroporation apparatus (Bio-Rad) with the following settings: 960 μF of capacitance and 0.220 kV of voltage. Cells were harvested 72 hours later and cell lysates were subjected to Western blotting analysis.

H. GST Pull Down Assay

The plasmid constructs for expression of GST-p85-SH2N, GST-p85-SH2C and GST-p85-SH3 were kindly provided by Dr. Lucia Rameh (Boston Biomedical Research Institute, Watertown, Mass.). *E. coli* BL21 cultures expressing GST-fusion proteins were grown to mid-log phase and were induced with 1 mM IPTG at 37° C. for 3 hours. The bacterial pellets were resuspended in PBS and were sonicatated to lyse the cells. 20% of Triton X-100 was added to the lysates (final concentration is 1%) and the mixture were incubated for 30 minutes to aid in solubilization of the fusion protein. Pellets were removed by centrifugation at 12000×g for 10 minutes at 4° C. Protein concentration was measured by Bradford assay. Aliquots of the supernatant were stored at −20° C.

Two hundred and fifty μg of each GST fusion protein lysates were bound to 25 μl of 50% preequilibrated glutathione-agarose (GA) beads slurry (GE Healthcare) for 1 hour at room temp, beads were then washed 5 times with PBS. Five hundred μl of lysates (1 μg/μl) from infected A549 cells or transfected 293T cells were incubated with GA beads/GST fusion protein complexes in RIPA-complete buffer. After an overnight incubation at 4° C., beads were washed 5 times in RIPA buffer. Bound proteins were resolved on SDS-PAGE followed by Western blotting using rabbit antiserum against NS1.

I. Immunofluorescence Staining

About 1×10⁴ of MDCK cells were plated on an 8 well-chamber slide and infected by wt or mutant viruses at an m.o.i of 1 in the presence of 20 μM LY294002 or 0.4% of DMSO. At 8 h.p.i., cells were fixed in a mixture of acetone and methanol (1:1) for 15 min at −20° C. After rehydrated with PBS, cells were incubated with monoclonal NP antibody (1:200) for 1 hour at room temperature. Cells were rinsed 3 times in PBS and incubated with secondary antibody Cy3-conjugated anti mouse IgG (1:400) for 45 minutes at room temperature. Finally cells were counter stained by DAPI (Roche) for 5 minutes. Images were obtained on a Carl Zeiss Axiovert 200M inverted fluorescent microscope.

EXAMPLE 2

Interaction of NS1 with p85 Subunit of PI3K

Figure 2:
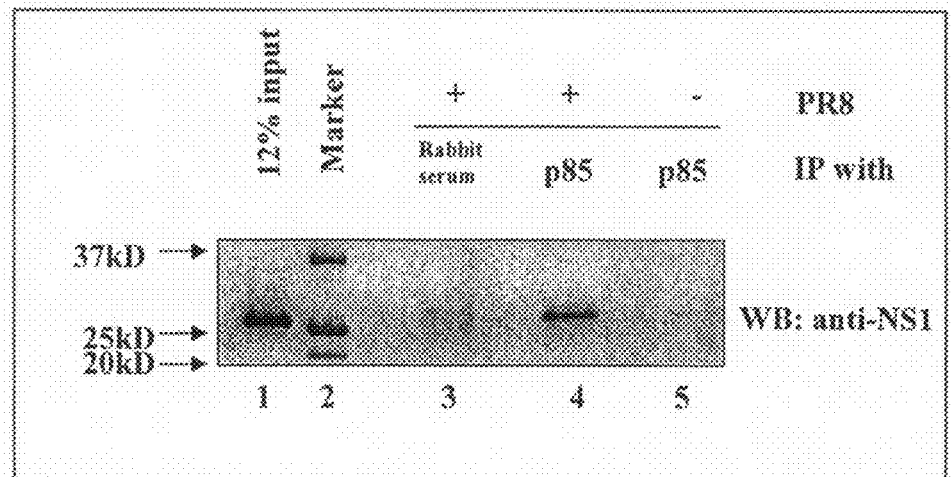
FIGS. 2A and 2B show that the NS1 protein interacts with the p85 subunit of PI3K via binding to the SH2 and SH3 domains of p85.
Figure 2:
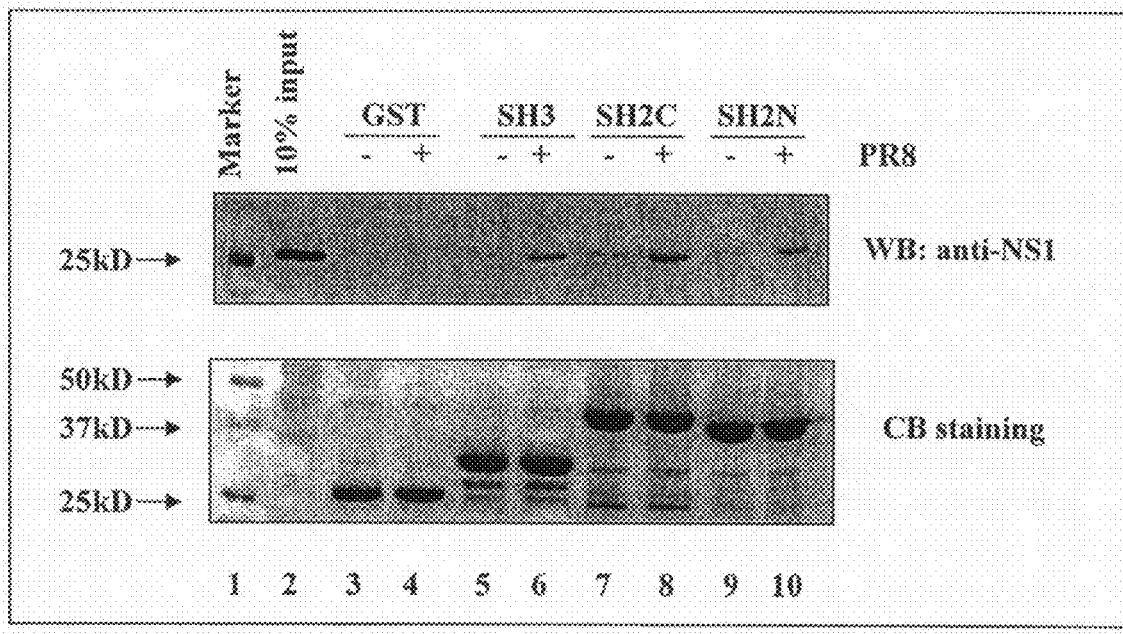

The interaction of the NS1 protein with the p85 subunit of PI3K was found to be mediated through binding of NS1 to the SH2 and SH3 domains of p85. Co-immunoprecipitation of NS1 and the p85 subunit of PI3K followed by Western blotting analysis was used to provide evidence of the interactions between NS1 and p85 in vivo. p85 antibody and normal rabbit serum were incubated with lysates of wt PR8 virus infected cells harvested at 6 h.p.i., or p85 antibody was incubated with mock infected cell lysates. Precipitated proteins were subjected to Western blotting analysis with a rabbit polyclonal NS1 antibody. As seen in FIG. 2, while normal rabbit serum failed to precipitate NS1 protein (lane 3), p85 antibody did precipitate NS1 protein (lane 4). No NS1 protein could be immunoprecipitated by p85 antibody from mock infected cell lysates (lane 5). 12% of input PR8 infected cell lysate was loaded as control (lane 1). This result demonstrates that NS1 protein interacts with p85 subunit of PI3K in vivo.

Next, the ability of the NS1 protein to interact with the SH2 and/or SH3 domains of the p85 subunit of PI3K was tested. A GST pull down assay was performed with mock or wt PR8 infected A549 cell lysates and a panel of different purified GST fusion proteins. After extensive washes, bound proteins were resolved by SDS-PAGE and detected with a polyclonal antibody against NS1. As seen in FIG. 2B upper panel, GST-SH3, GST-SH2C and GST-SH2N precipitated NS1 (lane 6, 8 and 10). GST did not precipitate NS1 from infected cell lysate (lane 4). NS1 was not precipitated from mock infected cell lysate by all purified GST fusion proteins (lane 3, 5, 7 and 9). Bound proteins were also resolved on SDS-PAGE and stained by Commassie blue to verify equal amount and integrity of GST fusion proteins (FIG. 2B, lower panel). These results demonstrate that NS1 is able to directly and specifically interact with the SH3, SH2C and to a lesser extent, with the SH2N domains of the p85 subunit of PI3K.

EXAMPLE 3

Transient Expression of NS1 Induces PI3K/Akt Activation

Figure 3:
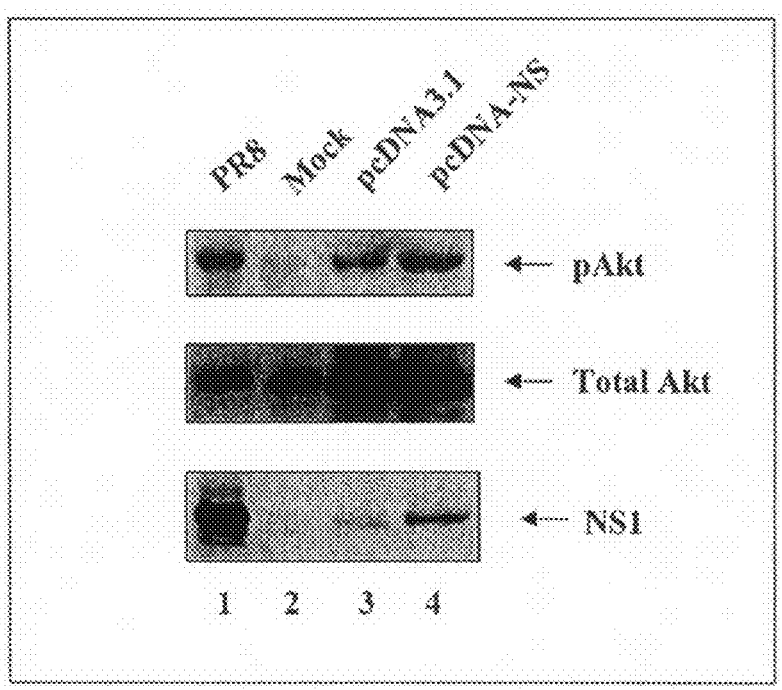
FIGS. 3A and 3B show that NS1 protein alone induces PI3K/Akt activation.
Figure 3:
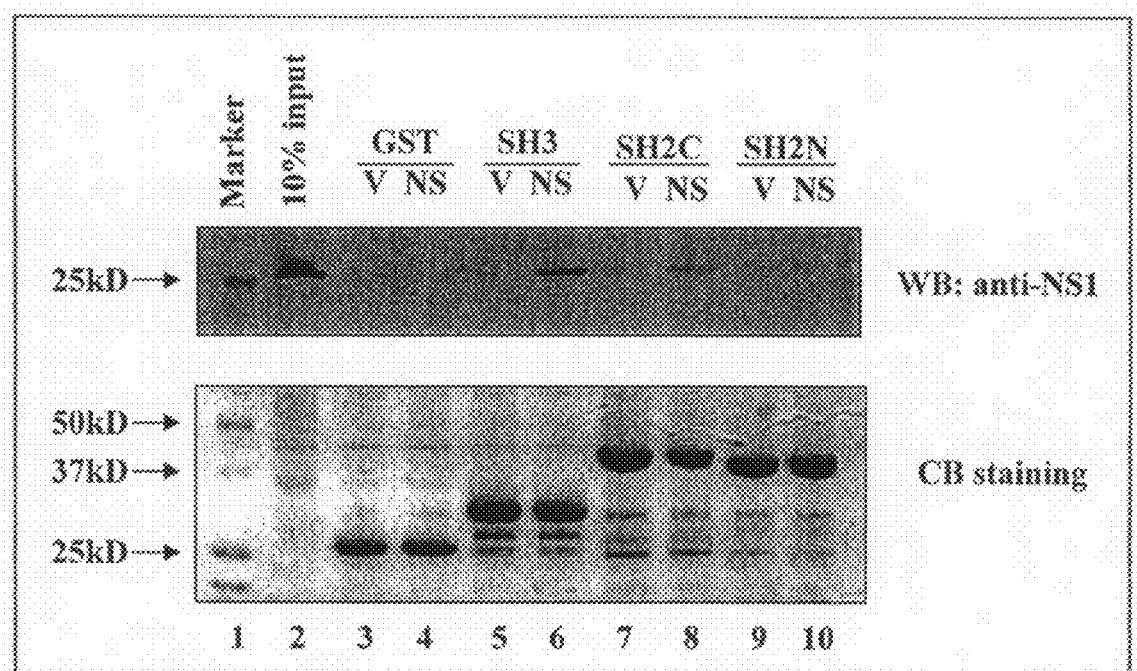

The ability of NS1 expression to activate PI3K/Akt was tested by using the plasmid pcDNA-NS, which encodes wt NS1 protein under the control of a CMV promoter. A549 cells were transiently transfected with NS1 by using LIPOFECTIN, LIPOFECTAMINE and FUGENE6 cationic lipid transfection reagents. Phosphorylated Akt was detected in the vector control sample as well as in the sample expressing NS1 subsequent to transfection (data not shown). Other investigators have reported that cationic lipid reagents can increase signal transduction (Giorgione et al., 1998), including marked activation of the kinase activity of the insulin receptor due to the formation of hexagonal phases in the cell membrane (Pramfalk et al., 2004). To circumvent the problem of activation of the PI3K/Akt pathway by cationic lipid agents during transfection experiments, electroporation was used instead to transiently express NS1. After electroporation, cells were maintained in medium containing 10% FCS for 48 hours followed by serum starvation for 24 hours. Cell lysates were then subjected to Western blotting by Phospho-Akt, total Akt and NS1 antibody respectively. As seen in FIG. 3A, while no phosphorylated Akt could be detected in mock infected cells (lane 2), Akt phosphorylation was evident in cells infected by wt PR8 (MOI of 1 PFU/cell. Cells were harvested at 6 h.p.i. (lane 1). Although vector electroporated cells induced phosphorylation of Akt (lane 3), NS1 expressing cells induced a greater degree of Akt phosphorylation (lane 4). Electroporated cells expressed elevated amounts of total Akt compared to mock and wt PR8 infected cells. Nevertheless, both vector and NS1 expressing cells have the same level of total Akt.

EXAMPLE 4

NS1 Alone Binds P85 SH2 and SH3 Domains

The ability of NS1 alone to bind P85 SH2 and/or SH3 domains in the absence of other viral components was tested. 293T cells were transfected with pcDNA-NS1, which expressed wt NS1 protein, or empty vector pcDNA3.1. Cell lysates were subjected to GST pull down assay. As shown in FIG. 3B, wt NS1 interacted with the p85 SH3 and SH2C domains, but not with the SH2N domain (upper panel, lane 6, 8 and 10). No interactions were seen in samples transfected with empty vector (lanes 3, 5, 7, 9). 10% input of pcDNA-NS1 transfected cell lysates was loaded on lane 2. The integrity of GST fusion proteins and their presence in equal amounts in each sample were verified by Commassie blue staining (FIG. 3B, lower panel).

EXAMPLE 5

Construction of Mutant Influenza Viruses with Substitutions in the SH2 Binding and SH3 Binding Motifs In order to establish the role of the three p85 binding motifs in the NS1 protein (designated SH2 binding motif, SH3 binding motif 1, and SH3 binding motif 2) on activation of the PI3K/Akt pathway, 5 mutant influenza viruses were constructed with mutations in the p85 binding sites. The following influenza virus mutants were constructed by using reverse genetics for strain A/PR/8/34:

- Mutant virus PR8-Y89Fmt encodes NS1 with a mutation in the SH2 binding motif at amino acid 89 (Y89F; SEQ ID NO:18).
- Mutant virus PR8-SH3-motif1mt encodes NS1 with prolines at 164 and 167 in the first SH3 binding motif replaced by alanines (P164A, P167A; SEQ ID NO:19).
- Mutant virus PR8-SH3-motif2mt encodes mutant NS1 with prolines at 212, 213 and 216 in the second SH3 binding motif replaced by alanines (P212A, P213A, P216A; SEQ ID NO:20).
- Mutant virus PR8-SH3-motif1/2mt encodes NS1 with mutations in both SH3 binding motif 1 and motif 2 (SEQ ID NO:21).
- Mutant virus PR8-SH2/SH3mt encodes NS1 with mutations in the SH2 binding motif, SH3 binding motif 1, and SH3 binding motif 2 (SEQ ID NO:22).

Figure 4:
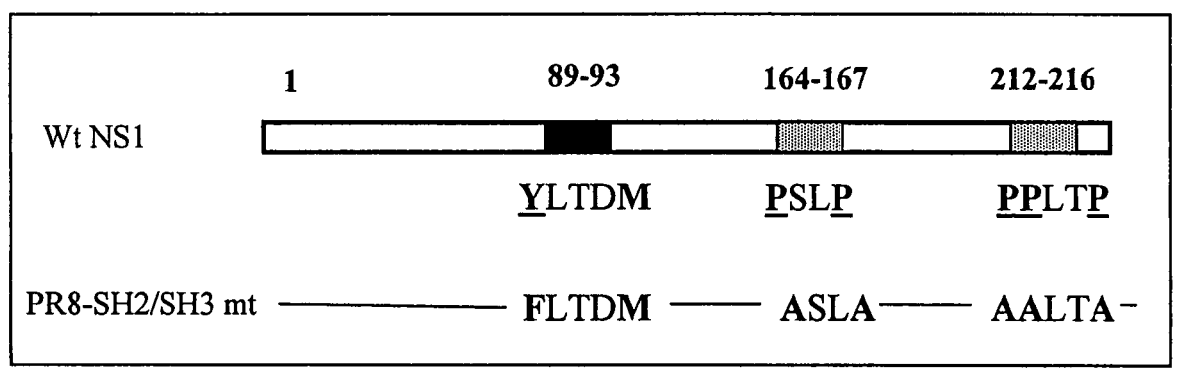
FIG. 4 depicts a schematic diagram showing the locations of one SH2 binding motif and two SH3 polyproline motifs on the wt NS1 protein (SEQ ID NO:58) and the changes in the amino acid sequence on mutant (mt) NS1 protein (SEQ ID NO:22).

For example, the mutant virus PR8-SH2/SH3-mt was generated by using the 8 plasmid reverse genetic system. Mutant virus PR8-SH2/SH3mt encoded the full-length NS1 protein with mutations at amino acid 89 (from Y to F, Y89F), amino acids 164-167 (from PSLP to ASLA, P164-167A) and amino acids 212-216 (from PPLTP to AALTA, P212-216A) (FIG. 4). Introduction of mutations at amino acid 164-167 and 212-216 does not disturb the NS2/NEP mRNA splicing donor site and NS2/NEP protein sequence. The genotype of the PR8-SH2/SH3mt was characterized and confirmed by DNA sequencing of the RT-PCR products derived from the NS gene of PR8-SH2/SH3mt virus. The virus was grown in 9 to 10-day old embryonated eggs with titer of $1.22 \times 10^8$ PFU/ml.

EXAMPLE 6

Mutant Influenza Virus PR8-SH2/SH3mt Fails to Activate PI3K/Akt Pathway

Figure 5:
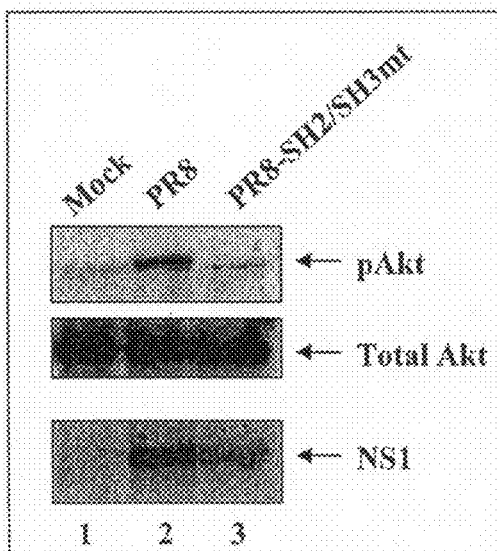
FIGS. 5A-5C show that the SH2 and SH3 binding motifs in NS1 contribute to PI3K/Akt pathway activation.
Figure 5:
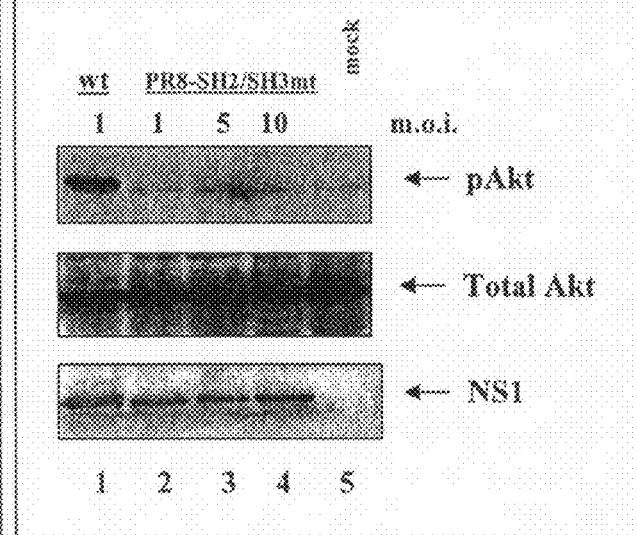
Figure 5:
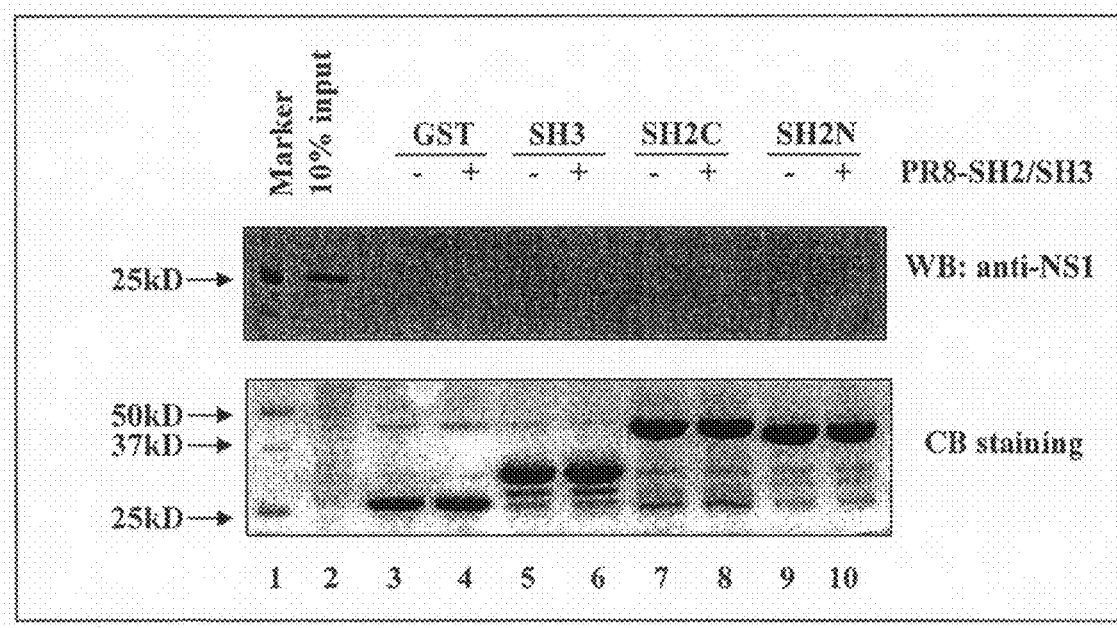

The ability of the PR8-SH2/SH3mt to induce Akt phosphorylation was tested. A549 cells were mock, wt PR8 or PR8-SH2/SH3mt infected at an MOI of 1 PFU/cell. Lysates of cell harvested at 6 h.p.i. were subjected to Western blotting using phospho-Akt (Ser473), total Akt, or NS1 antibody respectively. As shown in FIG. 5A, while the mutant virus PR8-SH2/SH3mt produced only slightly less NS1 than the wt virus at 6 h.p.i., the PR8-SH2/SH3mt failed to induce Akt phosphorylation. Both wt and mutant virus infections did not alter the levels of total cellular Akt.

To ascertain that PR8-SH2/SH3mt lacks the ability to activate PI3K/Akt, phosphorylation of Akt was assessed with cells infected with mutant virus at higher MOI. As seen in FIG. 5B, while wt PR8 infection induced high levels of Akt phosphorylation (lane 1), PR8-SH2/SH3mt infection did not lead to Akt phosphorylation at MOI of 1, 5 and 10 PFU/cell (lane 2-4). Total Akt levels and NS1 protein expression were monitored from the same samples by Western blotting using antibodies against total Akt or NS1.

The ability of mutant NS1 to interact with SH2 and SH3 domains of the p85 subunit of PI3K was examined by GST pull down assay. Mock or PR8-SH2/SH3mt virus infected A549 cell lysates were incubated with a panel of different purified GST fusion proteins. Pulled down proteins were analyzed by Western blotting using polyclonal NS1 antibodies. As shown in FIG. 5C upper panel, none of the SH3, SH2C or SH2N domains of p85 interacted with mutant NS1. Again, commassie blue staining showed that the same amounts of the GST fusion proteins were present in each sample (lower panel).

EXAMPLE 7

Attenuated Replication of PR8-SH2/SH3mt

Figure 6:
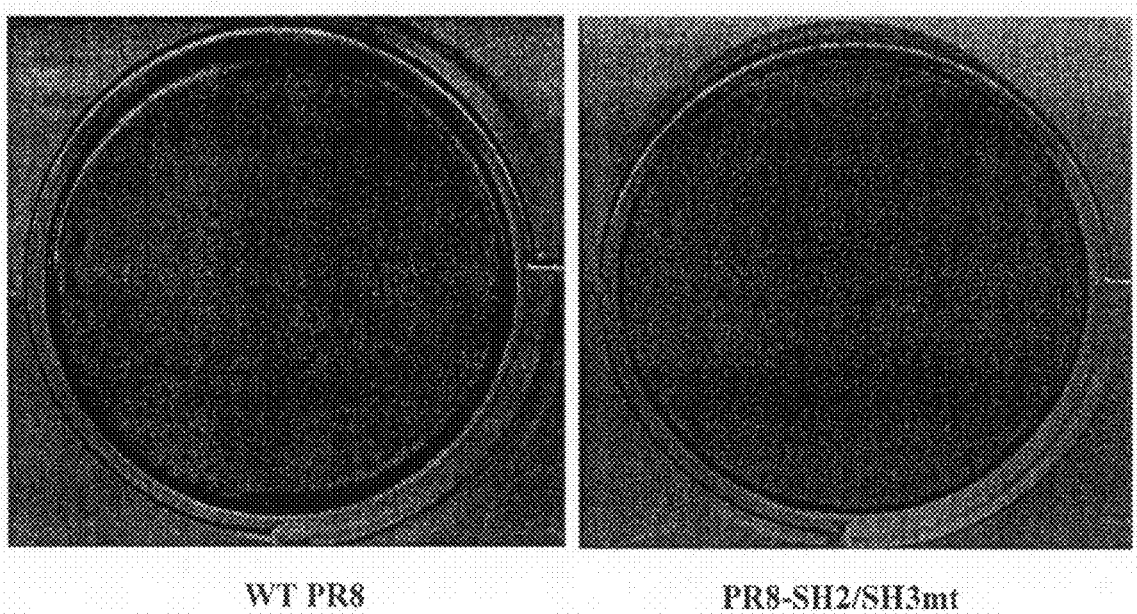
FIGS. 6A and 6B show that mutant virus PR8-SH2/SH3mt exhibits attenuated replication.
Figure 6:
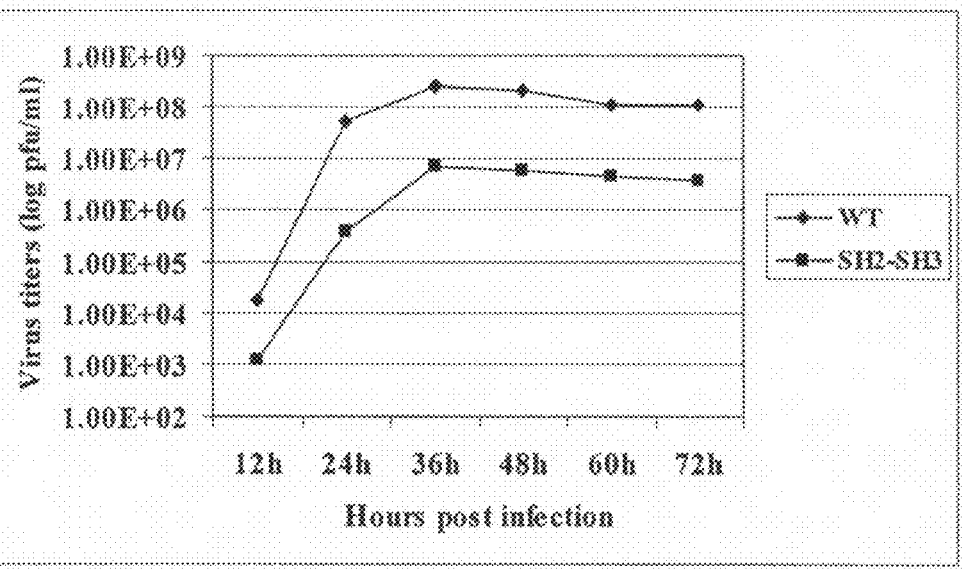
Figure 7:
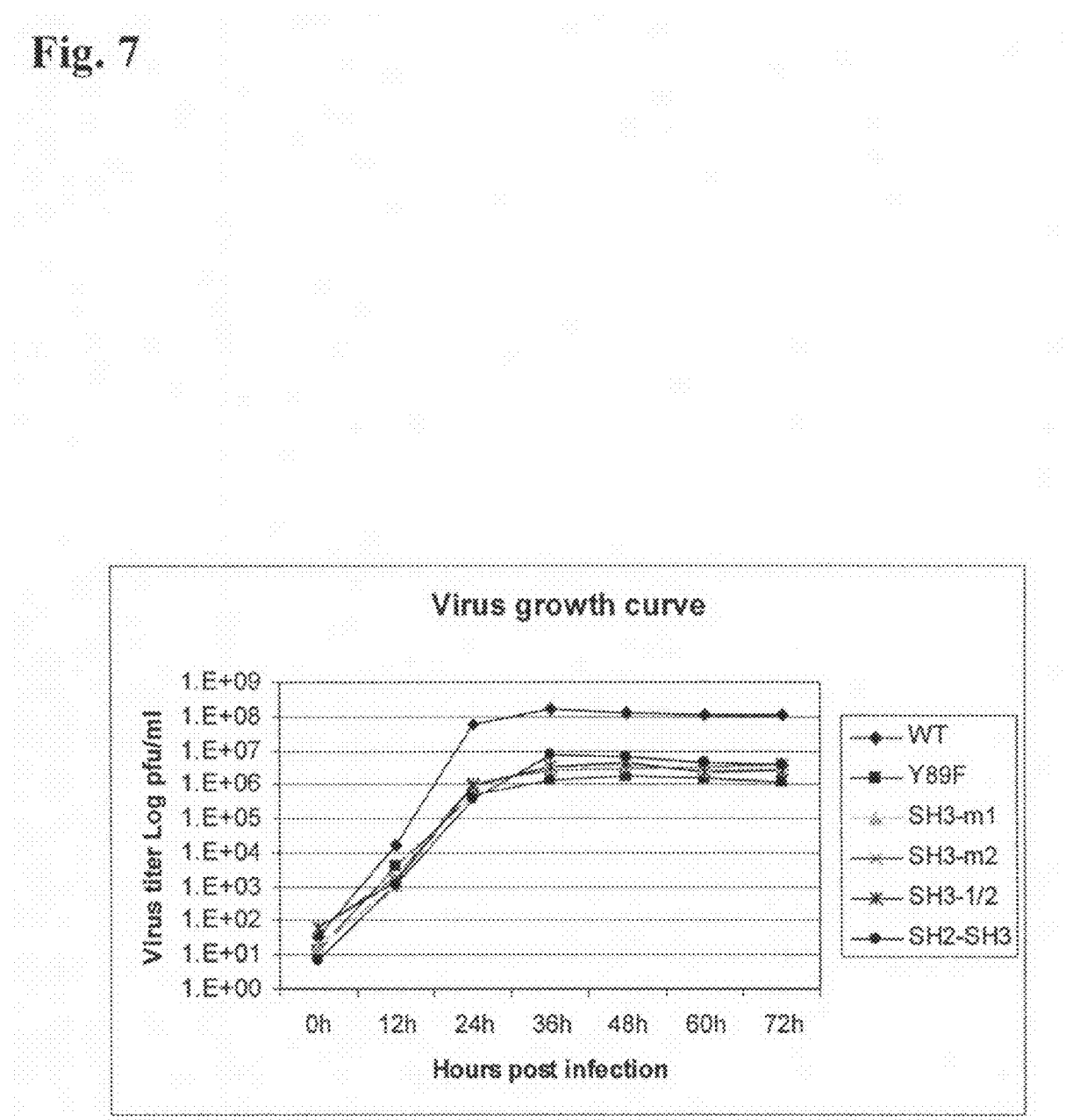
FIG. 7 compares viral titers of wt PR8 and five mutant PR8 viruses (described in Example 5) during multiple cycles of growth over 72 hours. MDCK cells were infected with either wt or mutant viruses at MOI of 0.001 PFU/cell. At the indicated times post infection, virus titers in the supernatant were determined by plaque assay in MDCK cells.

To investigate the consequences of mutations in the NS1 SH2 and SH3 binding domains on virus growth, mutant virus replication was examined by monitoring plaque size. As seen in FIG. 6A, the mutant PR8-SH2/SH3mt formed small plaques in MDCK cells, indicating that this mutant virus was attenuated for growth. To assess the degree of attenuation of the viruses, growth kinetics of the mutant viruses and the wt PR8 virus were compared during multiple cycles of growth of MDCK cells. MDCK cells were infected at an MOI of 0.001 PFU/cell. Supernatant was harvested at 12 hour intervals until 72 h.p.i., and virus titers were determined by plaque assay. Virus growth reached a plateau around 36 h.p.i. However, wt PR8 grew to over $10^8$ pfu/ml after 36 hours, whereas all mutant virus titers were 1 to 2 log lower than the wt PR8 virus (FIG. 6B and FIG. 7).

EXAMPLE 8

Blocked Viral Protein Expression in Cells Infected with PR8-SH2/SH3mt

Figure 8:
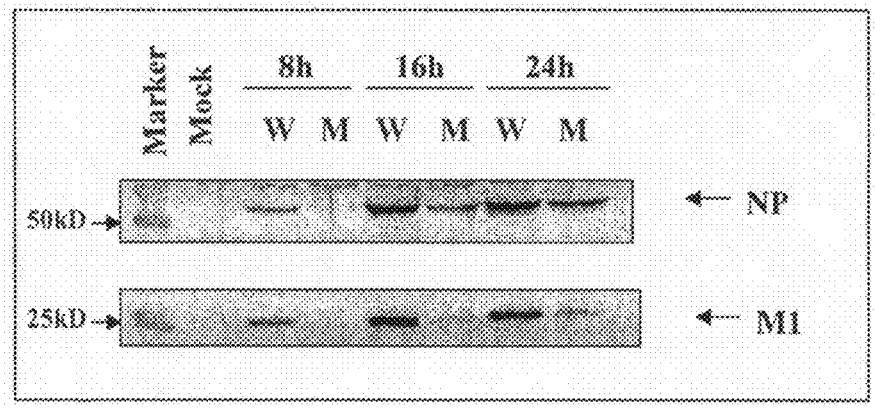
FIG. 8 shows that viral protein synthesis is blocked in mutant PR8-SH2/SH3mt virus infected cells. A549 cells were infected with wt or mutant virus (MOI of 0.01 PFU/ml), NP and M1 protein accumulation were determined by Western blotting analysis and band density was quantified by QUANTITY 1 software (Bio-Rad, Hercules, Calif.).
Figure 8:
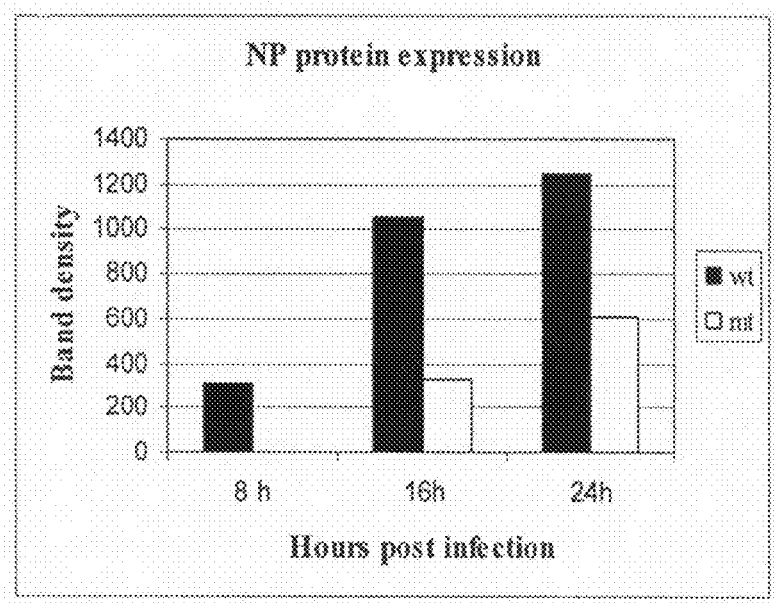
Figure 8:
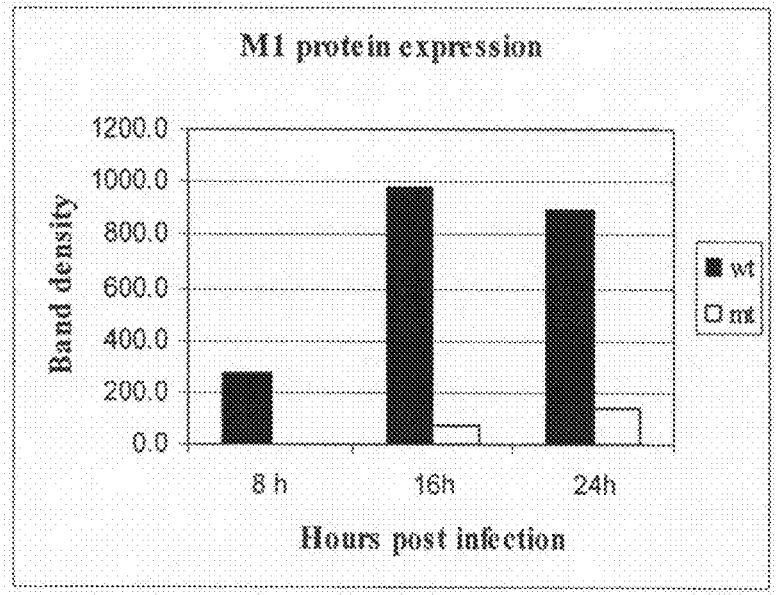

To examine the effects of mutations of NS1 SH2 and SH3 binding domains on viral protein expression, A549 cells infected with wt PR8 or mutant PR8-SH2/SH3mt at an MOI of 0.01 were harvested and subjected to Western blotting using antibodies against NP and M1 proteins. Quantification of the density of the protein bands was performed by QUANTITY ONE software (Bio-Rad). Reduced NP protein expression was observed in mutant virus infected cells at 8, 16 and 24 h.p.i. (FIG. 8, upper panel, lanes 4, 6 and 8). M1 protein expression was also significantly blocked in mutant virus infected cells (FIG. 8, lower panel lanes 4, 6 and 8).

In summary, binding of NS1 to SH2 and SH3 domains of the p85 regulatory subunit of PI3K is mediated via one SH2 binding domain (tyrosine at amino acid 89) and two SH3 binding domains (polyproline regions around residues 164 and 212) of the NS1 protein. Mutant viruses encoding full-length NS1 proteins with mutations in one or more of the SH2 binding and SH3 binding domains failed to activate the PI3K/Akt pathway and were attenuated in replication. Further study showed that viral protein synthesis was also substantially blocked in cells infected with mutant viruses.

Thus, the present application describes influenza virus variants, comprising substitutions in the NS1 protein that interfere with viral replication, protein expression, and phosphatidylinositol 3-kinase (PI3K) activation, as well as methods of using live attenuated influenza virus NS1 variants, NS1 variant polypeptides, and/or polynucleotides encoding them to elicit an immune response against influenza virus and/or interfere with viral replication. Although preferred embodiments of the subject invention have been described in some detail, it is understood that obvious variations can be made without departing from the spirit and the scope of the invention as defined by the claims herein.

The invention claimed is:

1. An isolated polynucleotide comprising a coding sequence for an influenza nonstructural 1 (NS1) polypeptide comprising at least one amino acid substitution in the Src homology 2 (SH2) binding domain, the first first Src homology 3 (SH3) binding domain or the second second Src homology 3 (SH3) binding domain of said NS1 protein, wherein said substitution reduces phosphatidylinositol 3-kinase (PI3K) activation activity of said NS1 polypeptide compared to the PI3K activation activity of the corresponding wild-type NS1 polypeptide.

2. The polynucleotide of claim 1, further comprising a promoter sequence operably linked to the coding sequence of the polynucleotide of claim 1.

3. The polynucleotide of claim 1, wherein the polynucleotide encodes a polypeptide comprising a sequence selected from SEQ ID NOS: 18-22.

4. An isolated host cell transformed with the recombinant polynucleotide of claim 1.

5. A method of producing a polypeptide, the method comprising:
   a) culturing a cell according to claim 4 under conditions suitable for expression of the polypeptide, and b) recovering the polypeptide so expressed.

6. The method of claim 5, wherein the polypeptide comprises an amino acid sequence selected from SEQ ID NOS: 18-22.

7. A method for producing an attenuated influenza virus with a reverse genetics system, comprising mutating a polynucleotide encoding an NS1 polypeptide in a reverse genetics system that produces influenza virus, wherein said encoded NS1 polypeptide comprises a mutation in the Src homology 2 (SH2) binding motif, the Src homology 3 (SH3) binding motif 1, or the SH3 binding motif 2 of said NS1 protein, wherein said mutation interferes with phosphatidylinositol 3-kinase (PI3K) activation and replication of said virus, and further wherein the NS1 polypeptide comprises a sequence selected from SEQ ID NOS:18-22.

* * * * *

SEQUENCE LISTING

<160> NUMBER OF SEQ ID NOS: 57

<210> SEQ ID NO 1
<211> LENGTH: 890
<212> TYPE: DNA
<213> ORGANISM: Influenza A H1N1

<400> SEQUENCE: 1

```
agcaaaagca gggtgacaaa gacataatgg atccaaacac tgtgtcaagc tttcaggtag      60
attgctttct ttggcatgtc cgcaaacgag ttgcagacca agaactaggt gatgccccat     120
tccttgatcg gcttcgccga gatcagaaat ccctaagagg aagggcagc actcttggtc      180 tggacatcga gacagccaca cgtgctggaa agcagatagt ggagcggatt ctgaaagaag     240
aatccgatga ggcacttaaa atgaccatgg cctctgtacc tgcgtcgcgt tacctaaccg     300
acatgactct tgaggaaatg tcaagggaat ggtccatgct catacccaag cagaaagtgg     360
caggccctct ttgtatcaga atggaccagg cgatcatgga taaaaacatc atactgaaag     420
cgaacttcag tgtgattttt gaccggctgg agactctaat attgctaagg gctttcaccg     480
aagagggagc aattgttggc gaaatttcac cattgccttc tcttccagga catactgctg     540
```

-continued

```
aggatgtcaa aaatgcagtt ggagtcctca tcggaggact tgaatggaat gataacacag      600
ttcgagtctc tgaaactcta cagagattcg cttggagaag cagtaatgag aatgggagac      660
ctccactcac tccaaaacag aaacgagaaa tggcggaac aattaggtca gaagtttgaa       720
gaaataagat ggttgattga agaagtgaga cacaaactga aggtaacaga gaatagtttt      780
gagcaaataa catttatgca agccttacat ctattgcttg aagtgggagca agagataaga    840 actttctcat ttcagcttat ttaataataa aaaacaccct tgtttctact                890
```

<210> SEQ ID NO 2
<211> LENGTH: 230
<212> TYPE: PRT
<213> ORGANISM: Influenza A H1N1

<400

-continued

```
Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Glu Lys
    50                  55                  60

Trp Arg Glu Gln Leu Gly Gln Lys Phe Glu Glu Ile Arg Trp Leu Ile
65                  70                  75                  80

Glu Glu Val Arg His Lys Leu Lys Val Thr Glu Asn Ser Phe Glu Gln
                85                  90                  95

Ile Thr Phe Met Gln Ala Leu His Leu Leu Leu Glu Val Glu Gln Glu
            100                 105                 110

Ile Arg Thr Phe Ser Phe Gln Leu Ile
        115                 120

<210> SEQ ID NO 4
<211> LENGTH: 853
<212> TYPE: DNA
<213> ORGANISM: Influenza A H3N2

<400> SEQUENCE: 4
gtgacaaaga cataatggat tccaacactg tgtcaagttt tcaggtagat tgcttccttt     60
ggcatgtccg aaaacaagtt gtagaccaag aactaggtga tgccccattc cttgatcggc    120
ttcgccgaga tcagaagtcc ctaaggggaa gaggcagcac tctcggtcta aacatcgaag    180
cagccaccca tgttggaaag cagatagtag agaagattct gaaggaagaa tctgatgagg    240
cacttaaaat gaccatggcc tccacacctg cttcgcgata cataactgac atgactattg    300
aggaattgtc aagggactgg ttcatgctaa tgcccaagca gaaagtggaa ggacctcttt    360
gcatcagaat agaccaagca atcatggata agaacatcat gttgaaagcg aatttcagtg    420
tgatttttga ccggctagag accctaatat tactaagggc tttcaccgaa gagggagcaa    480
ttgttggcga aatctcacca ttgccttctt ttccaggaca tactattgag gatgtcaaaa    540
atgcaattgg ggtcctcatc ggaggacttg aatggaatga taacacagtt cgagtctcta    600
aaactctaca gagattcgct tggggaagca gtaatgagaa tgggagacct ccacttactc    660
caaaacagaa acggaaaatg gcgagaacag ctaggtcaaa agttcgaaga gataagatgg    720
ctgattgaag aagtgagaca cagactgaag acaacagaga atagttttga gcaaataaca    780
ttcatgcaag ccttacagct actatttgaa gtggaacagg agataagaac tttctcgttt    840
cagcttattt aat                                                       853

<210> SEQ ID NO 5
<211> LENGTH: 237
<212> TYPE: PRT
<213> ORGANISM: Influenza A H3N2

<400> SEQUENCE: 5

Met Asp Ser Asn Thr Val Ser Ser Phe Gln Val Asp Cys Phe Leu Trp
1               5                   10                  15

His Val Arg Lys Gln Val Val Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asn Ile Glu Ala Ala Thr His Val Gly Lys Gln Ile
    50                  55                  60

Val Glu Lys Ile Leu Lys Glu Glu Ser Asp Glu Ala Leu Lys Met Thr
65                  70                  75                  80
```

```
Met Ala Ser Thr Pro Ala Ser Arg Tyr Ile Thr Asp Met Thr Ile Glu
                85                  90                  95

Glu Leu Ser Arg Asp Trp Phe Met Leu Met Pro Lys Gln Lys Val Glu
            100                 105                 110

Gly Pro Leu Cys Ile Arg Ile Asp Gln Ala Ile Met Asp Lys Asn Ile
        115                 120                 125

Met Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Gly Ser Ser Asn Glu
        195                 200                 205

Asn Gly Arg Pro Pro Leu Thr Pro Lys Gln Lys Arg Lys Met Ala Arg
    210                 215                 220

Thr Ala Arg Ser Lys Val Arg Arg Asp Lys Met Ala Asp
225                 230                 235

<210> SEQ ID NO 6
<211> LENGTH: 121
<212> TYPE: PRT
<213> ORGANISM: Influenza A H3N2

<400> SEQUENCE: 6

Met Asp Ser Asn Thr Val Ser Ser Phe Gln Asp Ile Leu Leu Arg Met
1               5                   10                  15

Ser Lys Met Gln Leu Gly Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Leu Leu Gln Asn Arg Asn Gly Lys
    50                  55                  60

Trp Arg Glu Gln Leu Gly Gln Lys Phe Glu Glu Ile Arg Trp Leu Ile
65                  70                  75                  80

Glu Glu Val Arg His Arg Leu Lys Thr Thr Glu Asn Ser Phe Glu Gln
                85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
        115                 120

<210> SEQ ID NO 7
<211> LENGTH: 851
<212> TYPE: DNA
<213> ORGANISM: Influenza A H5N1

<400> SEQUENCE: 7
ggtgacaaaa acataatgga ttccaacact gtgtcaagct ttcaggtaga ctgctttctt    60
tggcatgtcc gcaaacgatt tgcagaccga gaactgggtg atgccccatt ccttgaccgg   120
cttcgccgag atcagaagtc cctaagagga agaggcaaca ctcttggtct ggacatcgaa   180
acagctactc gcgcaggaaa gcagatagtg gagcggattc tggaggagga gtctgataag   240
gcacttaaaa tgccggcttc acgctaccta actgacatga ctctcgaaga aatgtcaagg   300
```

```
gactggttca tgctcatgcc caagcagaaa gtggcaggtt ccctttgcat caaaatggac    360
caggcaataa tggataaagt catcatattg aaagcaaact tcagtgtgat ttttgaccga    420
ttggaaaccc taatactact tagagctttc acagaagaag gagcaatcgt gggagaaatc    480
tcaccattac cttctcttcc aggacatact ggtgaggatg tcaaaaatgc aattggcgtc    540
ctcatcggag acttgaatg gaatgataac acagttcaag tcactgaaac tctacagaga     600
ttcgcttgga agcagtga tgaggatggg agacttccac tccctccaaa tcagaaacgg      660
aaaatggcga aacaattga gtcagaagtt tgaagaaata ggtggctga ttgaagaagt      720 aagcataga ttgaaaatta cagaaaacag cttcgaacag ataacgttta tgcaagcctt     780
acaactactg cttgaagtgg agcaagagat aagagccttc tcgtttcagc ttatttaatg    840
ataaaaaaca c                                                         851
```

<210> SEQ ID NO 8
<211> LENGTH: 225
<212> TYPE: PRT
<213> ORGANISM: Influenza A H5N1

<400> SEQUENCE: 8

```
Met Asp Ser Asn Thr Val Ser Ser Phe Gln Val Asp Cys Phe Leu Trp
1               5                   10                  15

His Val Arg Lys Arg Phe Ala Asp Arg Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Lys Ala Leu Lys Met Pro
65                  70                  75                  80

Ala Ser Arg Tyr Leu Thr Asp Met Thr Leu Glu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Val Ile Ile Leu Lys Ala Asn
        115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Pro Ser
145                 150                 155                 160

Leu Pro Gly His Thr Gly Glu Asp Val Lys Asn Ala Ile Gly Val Leu
                165                 170                 175

Ile Gly Gly Leu Glu Trp Asn Asp Asn Thr Val Gln Val Thr Glu Thr
            180                 185                 190

Leu Gln Arg Phe Ala Trp Arg Ser Ser Asp Glu Asp Gly Arg Leu Pro
        195                 200                 205

Leu Pro Pro Asn Gln Lys Arg Lys Met Ala Arg Thr Ile Glu Ser Glu
    210                 215                 220

Val
225
```

<210> SEQ ID NO 9
<211> LENGTH: 121
<212> TYPE: PRT
<213> ORGANISM: Influenza A H5N1

<400> SEQUENCE: 9

Met Asp Ser Asn Thr Val Ser Ser Phe Gln Asp Ile Leu Val Arg Met
1               5                   10                  15

Ser Lys Met Gln Leu Ala Ser Ser Glu Asp Leu Asn Gly Met Ile
            20                  25                  30

Thr Gln Phe Lys Ser Leu Lys Leu Tyr Arg Asp Ser Leu Gly Glu Ala
                35                  40                  45

Val Met Arg Met Gly Asp Phe His Ser Leu Gln Ile Arg Asn Gly Lys
    50                  55                  60

Trp Arg Glu Gln Leu Ser Gln Lys Phe Glu Glu Ile Arg Trp Leu Ile
65                  70                  75                  80

Glu Glu Val Arg His Arg Leu Lys Ile Thr Glu Asn Ser Phe Glu Gln
                85                  90                  95

Ile Thr Phe Met Gln Ala Leu Gln Leu Leu Glu Val Glu Gln Glu
            100                 105                 110

Ile Arg Ala Phe Ser Phe Gln Leu Ile
        115                 120

<210> SEQ ID NO 10
<211> LENGTH: 823
<212> TYPE: DNA
<213> ORGANISM: Influenza A H5N1

<400> SEQUENCE: 10
atggattcca acactgtgtc aagctttcag gtagactgct ttctttggca tgtccgcaaa     60
cgatttgcag accaagaact gggtgatgcc ccattccttg accggcttcg ccgagatcag    120
aagtccctaa aggaagagg caacactctt ggtctggaca tcgaaacagc tactcgcgca    180
ggaaagcaga tagtggagcg aattctggag gaggagtctg ataaggcact aaaaatgccg    240
gcttcacgct acctaactga catgactctc gaagaaatgt caagggactg gttcatgctc    300
atgcccaagc agaaagtggc aggttcccct tgcatcaaaa tggaccaggc aataatggat    360
aaaaccatca tattgaaagc aaacttcagt gtgattttg accggttgga acccctaata    420
ctacttagag cttttcacaga agaaggggca atcgtgggag aaatctcacc attaccttct    480
cttccaggac atactggtga ggatgtcaaa atgcaattg cgtcctcat cggaggactt    540
gaatggaatg ataacacagt tcgagtcact gaaactatac agagattcgc ttggagaaac    600
agtgatgagg atgggagact tccactccct ccaaatcaga aacggaaaat ggcgagaaca    660
attgagtcag aagtttgaag aaataaggtg gctgattgaa gaagtaagac atagattgaa    720
aattacagaa aacagcttcg aacagataac gtttatgcaa gccttacaac tactgcttga    780
agtggagcaa gagataagag ccttctcgtt tcagcttatt taa                      823

<210> SEQ ID NO 11
<211> LENGTH: 225
<212> TYPE: PRT
<213> ORGANISM: Influenza A H5N1

<400> SEQUENCE: 11

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Asn
        35                  40                  45

```
Thr Leu Gly Leu Asp Ile Glu Thr Ala Thr Arg Ala Gly Lys Gln Ile
    50                  55                  60

Val Glu Arg Ile Leu Glu Glu Ser Asp Lys Ala Leu Lys Met Pro
65                  70                  75                  80

Ala Ser Arg Tyr Leu Thr Asp Met Thr Leu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Thr Ile Ile Leu Lys Ala Asn
            115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Pro Ser
145                 150                 155                 160

Leu Pro Gly His Thr Gly Glu Asp Val Lys Asn Ala Ile Gly Val Leu
                165                 170                 175

Ile Gly Gly Leu Glu Trp Asn Asp Asn Thr Val Arg Val Thr Glu Thr
            180                 185                 190

Ile Gln Arg Phe Ala Trp Arg Asn Ser Asp Glu Asp Gly Arg Leu Pro
        195                 200                 205

Leu Pro Pro Asn Gln Lys Arg Lys Met Ala Arg Thr Ile Glu Ser Glu
        210                 215                 220

Val
225

<210> SEQ ID NO 12
<211> LENGTH: 121
<212> TYPE: PRT
<213> ORGANISM: Influenza A H5N1

<400> SEQUENCE: 12

Met Asp Ser Asn Thr Val Ser Ser Phe Gln Asp Ile Leu Val Arg Met
1               5                   10                  15

Ser Lys Met Gln Leu Ala Ser Ser Ser Glu Asp Leu Asn Gly Met Ile
            20                  25                  30

Thr Gln Phe Glu Ser Leu Lys Leu Tyr Arg Asp Ser Leu Gly Glu Thr
        35                  40                  45

Val Met Arg Met Gly Asp Phe His Ser Leu Gln Ile Arg Asn Gly Lys
    50                  55                  60

Trp Arg Glu Gln Leu Ser Gln Lys Phe Glu Glu Ile Arg Trp Leu Ile
65                  70                  75                  80

Glu Glu Val Arg His Arg Leu Lys Ile Thr Glu Asn Ser Phe Glu Gln
                85                  90                  95

Ile Thr Phe Met Gln Ala Leu Gln Leu Leu Leu Glu Val Glu Gln Glu
            100                 105                 110

Ile Arg Ala Phe Ser Phe Gln Leu Ile
        115                 120

<210> SEQ ID NO 13
<211> LENGTH: 890
<212> TYPE: DNA
<213> ORGANISM: Influenza A H5N1

<400> SEQUENCE: 13
agcaaaagca gggtgacaaa aacataatgg attccaacac tgtgtcaagc tttcaggtag    60
```

-continued

```
actgctttct ttggcgtgtc cgcaaacgat ttgcagacca agaactgggt gatgccccat    120
tccttgaccg gcttcgccga gatcagaagt ccctaagagg aagaggcagc actcttggtc    180
tggacatcag aactgccact cgtgaaggaa agcatatagt ggagcggatt ctggaggaag    240
aatctgatga ggcacttaaa atgactatcg cttcagtgcc tgctccacgc tacctaactg    300
aaatgactct tgaggaaatg tcaagggact ggttaatgct cattcccaag cagaaagtga    360
cagggtccct ttgcattaga atggaccagg caataatgga taaagacatc atattgaaag    420
caaactttag tgtgattttt aatcgacttg aagctctgat actacttaga gcttttacag    480
acgaaggagc aatagtgggc gaaatctcac cattgccttc ccttccagga catactgaag    540
aggatgtcaa aaatgcaatt ggggtcctca tcggaggact tgaatggaat gataacacag    600
ttcgagtctc tgaaactcta cagagattca cttggagaag cagtgatgag aatgggagat    660
ctccactccc tccaaaacag aaacggaaaa tggagagaac aattgagcca gaagtttgaa    720
gagataagat ggttaattga agaagtgcga cataggttaa gaattacaga gaatagcttt    780
gaacaaataa cctttatgca agccttacaa ctattgcttg aagtggagca agagataaga    840
actttctcgt ttcagcttat ttaatgataa aaaacaccct tgtttctact              890
```

<210> SEQ ID NO 14
<211> LENGTH: 230
<212> TYPE: PRT
<213> ORGANISM: Influenza A H5N1

<400> SEQUENCE: 14

```
Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Ser Asp Glu Ala Leu Lys Met Thr
65                  70                  75                  80

Ile Ala Ser Val Pro Ala Pro Arg Tyr Leu Thr Glu Met Thr Leu Glu
                85                  90                  95

Glu Met Ser Arg Asp Trp Leu Met Leu Ile Pro Lys Gln Lys Val Thr
            100                 105                 110

Gly Ser Leu Cys Ile Arg Met Asp Gln Ala Ile Met Asp Lys Asp Ile
        115                 120                 125

Ile Leu Lys Ala Asn Phe Ser Val Ile Phe Asn Arg Leu Glu Ala Leu
    130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Glu Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Ser Pro Leu Pro Pro Lys Gln Lys Arg Lys Met Glu Arg
    210                 215                 220

Thr Ile Glu Pro Glu Val
```

<210> SEQ ID NO 15
<211> LENGTH: 121
<212> TYPE: PRT
<213> ORGANISM: Influenza A H5N1

<400> SEQUENCE: 15

Met Asp Ser Asn Thr Val Ser Ser Phe Gln Asp Ile Leu Lys Arg Met
1               5                   10                  15

Ser Lys Met Gln Leu Gly Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Gly Lys
    50                  55                  60

Trp Arg Glu Gln Leu Ser Gln Lys Phe Glu Glu Ile Arg Trp Leu Ile
65                  70                  75                  80

Glu Glu Val Arg His Arg Leu Arg Ile Thr Glu Asn Ser Phe Glu Gln
                85                  90                  95

Ile Thr Phe Met Gln Ala Leu Gln Leu Leu Leu Glu Val Glu Gln Glu
            100                 105                 110

Ile Arg Thr Phe Ser Phe Gln Leu Ile
        115                 120

<210> SEQ ID NO 16
<211> LENGTH: 890
<212> TYPE: DNA
<213> ORGANISM: Influenza A H7N7

<400> SEQUENCE: 16
agcaaaagca gggtgacaaa acataatgg attccaacac tgtgtcaagc tttcaggtag      60
actgctttct ttggcatgtc cgcaaacgat ttgcagacca gaactgggt gatgccccat     120
tccttgaccg gcttcgccga gatcagaaat ccctaagagg aagaggcagc actcttggtc    180
tggacatcga cagctact cgtgcgggaa agcagatagt ggagcggatt ctggaggaag      240
aatctgatga ggcacttaaa atgactattg cttcagtgct ggcttcacgc tacctaactg    300
acatgactct tgaagaaatg tcaagggact ggttcatgct catgcccaag cagaaagtgg    360
caggttccct ttgcatcaga atggaccagg caataatgga tagaaacatc atattgaagg    420
caaacttcag tgtggttttt gaccggctgg aaaccctaat actacttaga gctttcacag    480
aagaaggagc aattgtggga gaaatctcac cattaccttc tcttccagga catactgatg    540
aggatgtcaa aaatgcaatt gggtcctca tcgaggact tgaatggaat gataacacag     600
ttcgagtctc tgaaactcta cagagattcg cttggagaag cagtaatgag gatgggagac    660
ctccactccc tccaaagcag aaacggaaaa tggcagaac aattgagtca gaagtttgaa    720
gagataagat ggctgattga agaagtgcga cataggttga agattacaga gaacagcttt    780
gaacagatta cgtttatgca agccttacaa ctattgcttg aagtagagca agagataaga    840
actttctcgt ttcagcttat ttaatgataa aaaacaccct gtttctact                890

<210> SEQ ID NO 17
<211> LENGTH: 230
<212> TYPE: PRT
<213> ORGANISM: Influenza A H7N7

<400> SEQUENCE: 17

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Glu Ala Leu Lys Met Thr
65                  70                  75                  80

Ile Ala Ser Val Leu Ala Ser Arg Tyr Leu Thr Asp Met Thr Leu Glu
                85                  90                  95

Glu Met Ser Arg Asp Trp Phe Met Leu Met Pro Lys Gln Lys Val Ala
                100                 105                 110

Gly Ser Leu Cys Ile Arg Met Asp Gln Ala Ile Met Asp Arg Asn Ile
            115                 120                 125

Ile Leu Lys Ala Asn Phe Ser Val Val Phe Asp Arg Leu Glu Thr Leu
        130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Asp Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asp Gly Arg Pro Pro Leu Pro Lys Gln Lys Arg Lys Met Ala Arg
    210                 215                 220

Thr Ile Glu Ser Glu Val
225             230

<210> SEQ ID NO 18
<211> LENGTH: 230
<212> TYPE: PRT
<213> ORGANISM: Artificial
<220> FEATURE:
<223> OTHER INFORMATION: H1N1 PR8-SH2-motif-mt Y89F

<400> SEQUENCE: 18

Met Asp Pro Asn Thr Val

```
Ile Leu Lys Ala Asn Phe Ser Val Ile Phe Asp Arg Leu Glu Thr Leu
        130                 135                 140
Ile Leu Arg Ala Phe Thr Glu Glu Gly Ala Ile Val Gly Glu Ile
145                 150                 155                 160
Ser Pro Leu Pro Ser Leu Pro Gly His Thr Ala Glu Asp Val Lys Asn
                165                 170                 175
Ala Val Gly Val Leu Ile Gly Gly Leu Glu Trp Asn Asp Asn Thr Val
            180                 185                 190
Arg Val Ser Glu Thr Leu Gln Arg Phe Ala Trp Arg Ser Ser Asn Glu
        195                 200                 205
Asn Gly Arg Pro Pro Leu Thr Pro Lys Gln Lys Arg Glu Met Ala Gly
    210                 215                 220
Thr Ile Arg Ser Glu Val
225                 230
```

<210> SEQ ID NO 19
<211> LENGTH: 230
<212> TYPE: PRT
<213> ORGANISM: Artificial
<220> FEATURE:
<223> OTHER INFORMATION: H1N1 PR8-SH3-motif1-mt P164A P167A

<400> SEQUENCE: 19

```
Met Asp Pro Asn Thr Val Ser Ser Phe Gln Val Asp Cys Phe Leu Trp
1               5                   10                  15
His Val Arg Lys Arg Val Ala Asp Gln Glu Leu Gly Asp Ala Pro Phe
            20                  25                  30
Leu Asp Arg Leu Arg Arg Asp Gln Lys Ser Leu Arg Gly Arg Gly Ser
        35                  40                  45
Thr Leu Gly Leu Asp Ile Glu Thr Ala Thr Arg Ala Gly Lys Gln Ile
    50                  55                  60
Val Glu Arg Ile Leu Lys Glu Glu Ser Asp Glu Ala Leu Lys Met Thr
65                  70                  75                  80
Met Ala Ser Val Pro Ala Ser Arg Tyr Leu Thr Asp Met Thr Leu Glu
                85                  90                  95
Glu Met Ser Arg Glu Trp Ser Met Leu Ile Pro Lys Gln Lys Val Ala
            100                 105                 110
Gly Pro Leu Cys Ile Arg Met Asp Gln Ala Ile Met Asp Lys Asn Ile
        115                 120                 125
Ile Leu Lys Ala Asn Phe Ser Val Ile Phe Asp Arg Leu Glu Thr Leu
    130                 135                 140
Ile Leu Arg Ala Phe Thr Glu Glu Gly Ala Ile Val Gly Glu Ile
145                 150                 155                 160
Ser Pro Leu Ala Ser Leu Ala Gly His Thr Ala Glu Asp Val Lys Asn
                165                 170                 175
Ala Val Gly Val Leu Ile Gly Gly Leu Glu Trp Asn Asp Asn Thr Val
            180                 185                 190
Arg Val Ser Glu Thr Leu Gln Arg Phe Ala Trp Arg Ser Ser Asn Glu
        195                 200                 205
Asn Gly Arg Pro Pro Leu Thr Pro Lys Gln Lys Arg Glu Met Ala Gly
    210                 215                 220
Thr Ile Arg Ser Glu Val
225                 230
```

<210> SEQ ID NO 20

```
<211> LENGTH: 230
<212> TYPE: PRT
<213> ORGANISM: Artificial
<220> FEATURE:
<223> OTHER INFORMATION: H1N1 PR8-SH3-motif2-mt P212A P213A P216A

<400> SEQUENCE: 20

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Leu Pro Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Ala Ala Leu Thr Ala Lys Gln Lys Arg Glu Met Ala Gly
    210                 215                 220

Thr Ile Arg Ser Glu Val
225                 230

<210> SEQ ID NO 21
<211> LENGTH: 230
<212> TYPE: PRT
<213> ORGANISM: Artificial
<220> FEATURE:
<223> OTHER INFORMATION: H1N1 PR8-SH3-motif1/2-mt P164A P167A P212A
      P213A P216A

<400> SEQUENCE: 21

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80
```

```
Met Ala Ser Val Pro Ala Ser Arg Tyr Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Ala Ser Leu Ala Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asn Gly Arg Ala Ala Leu Thr Ala Lys Gln Lys Arg Glu Met Ala Gly
    210                 215                 220

Thr Ile Arg Ser Glu Val
225                 230

<210> SEQ ID NO 22
<211> LENGTH: 230
<212> TYPE: PRT
<213> ORGANISM: Artificial
<220> FEATURE:
<223> OTHER INFORMATION: H1N1 PR8-SH2/SH3-mt Y89F P164A P167A P212A
      P213A P216A

<400> SEQUENCE: 22

Met Asp Pro Asn Thr Val Ser Ser Phe Gln Val Asp Cys Phe Leu Trp
1               5                   10                  15

His Val Arg Lys Arg Val Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Lys Glu Glu Ser Asp Glu Ala Leu Lys Met Thr
65                  70                  75                  80

Met Ala Ser Val Pro Ala Ser Arg Phe Leu Thr Asp Met Thr Leu Glu
                85                  90                  95

Glu Met Ser Arg Glu Trp Ser Met Leu Ile Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Ala Ser Leu Ala Gly His Thr Ala Glu Asp Val Lys Asn
                165                 170                 175

Ala Val Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205
```

Asn Gly Arg Ala Ala Leu Thr Ala Lys Gln Lys Arg Glu Met Ala Gly
    210                 215                 220

Thr Ile Arg Ser Glu Val
225                 230

<210> SEQ ID NO 23
<211> LENGTH: 237
<212> TYPE: PRT
<213> ORGANISM: Artificial
<220> FEATURE:
<223> OTHER INFORMATION: H3N2 Udorn-SH2-motif-mt Y89F

<400> SEQUENCE: 23

Met Asp Ser Asn Thr Val Ser Ser Phe Gln Val Asp Cys Phe Leu Trp
1               5                   10                  15

His Val Arg Lys Gln Val Val Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asn Ile Glu Ala Ala Thr His Val Gly Lys Gln Ile
    50                  55                  60

Val Glu Lys Ile Leu Lys Glu Glu Ser Asp Glu Ala Leu Lys Met Thr
65                  70                  75                  80

Met Ala Ser Thr Pro Ala Ser Arg Phe Ile Thr Asp Met Thr Ile Glu
                85                  90                  95

Glu Leu Ser Arg Asp Trp Phe Met Leu Met Pro Lys Gln Lys Val Glu
            100                 105                 110

Gly Pro Leu Cys Ile Arg Ile Asp Gln Ala Ile Met Asp Lys Asn Ile
        115                 120                 125

Met Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Gly Ser Ser Asn Glu
        195                 200                 205

Asn Gly Arg Pro Pro Leu Thr Pro Lys Gln Lys Arg Lys Met Ala Arg
    210                 215                 220

Thr Ala Arg Ser Lys Val Arg Arg Asp Lys Met Ala Asp
225                 230                 235

<210> SEQ ID NO 24
<211> LENGTH: 237
<212> TYPE: PRT
<213> ORGANISM: Artificial
<220> FEATURE:
<223> OTHER INFORMATION: H3N2 Udorn-SH3-motif1-mt P164A P167A

<400> SEQUENCE: 24

Met Asp Ser Asn Thr Val Ser Ser Phe Gln Val Asp Cys Phe Leu Trp
1               5                   10                  15

His Val Arg Lys Gln Val Val Asp Gln Glu Leu Gly Asp Ala Pro Phe
            20                  25                  30

Leu Asp Arg Leu Arg Arg Asp Gln Lys Ser Leu Arg Gly Arg Gly Ser

```
                35                  40                  45
Thr Leu Gly Leu Asn Ile Glu Ala Ala Thr His Val Gly Lys Gln Ile
 50                  55                  60

Val Glu Lys Ile Leu Lys Glu Glu Ser Asp Glu Ala Leu Lys Met Thr
 65                  70                  75                  80

Met Ala Ser Thr Pro Ala Ser Arg Tyr Ile Thr Asp Met Thr Ile Glu
                 85                  90                  95

Glu Leu Ser Arg Asp Trp Phe Met Leu Met Pro Lys Gln Lys Val Glu
            100                 105                 110

Gly Pro Leu Cys Ile Arg Ile Asp Gln Ala Ile Met Asp Lys Asn Ile
        115                 120                 125

Met Leu Lys Ala Asn Phe Ser Val Ile Phe Asp Arg Leu Glu Thr Leu
130                 135                 140

Ile Leu Leu Arg Ala Phe Thr Glu Glu Gly Ala Ile Val Gly Glu Ile
145                 150                 155                 160

Ser Pro Leu Ala Ser Phe Ala Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Gly Ser Ser Asn Glu
        195                 200                 205

Asn Gly Arg Pro Pro Leu Thr Pro Lys Gln Lys Arg Lys Met Ala Arg
210                 215                 220

Thr Ala Arg Ser Lys Val Arg Arg Asp Lys Met Ala Asp
225                 230                 235

<210> SEQ ID NO 25
<211> LENGTH: 237
<212> TYPE: PRT
<213> ORGANISM: Artificial
<220> FEATURE:
<223> OTHER INFORMATION: H3N2 Udorn-SH3-motif2-mt P212A P213A P216A

<400> SEQUENCE: 25

Met Asp Ser Asn Thr Val Ser Ser Phe Gln Val Asp Cys Phe Leu Trp
 1               5                  10                  15

His Val Arg Lys Gln Val Val Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asn Ile Glu Ala Ala Thr His Val Gly Lys Gln Ile
 50                  55                  60

Val Glu Lys Ile Leu Lys Glu Glu Ser Asp Glu Ala Leu Lys Met Thr
 65                  70                  75                  80

Met Ala Ser Thr Pro Ala Ser Arg Tyr Ile Thr Asp Met Thr Ile Glu
                 85                  90                  95

Glu Leu Ser Arg Asp Trp Phe Met Leu Met Pro Lys Gln Lys Val Glu
            100                 105                 110

Gly Pro Leu Cys Ile Arg Ile Asp Gln Ala Ile Met Asp Lys Asn Ile
        115                 120                 125

Met Leu Lys Ala Asn Phe Ser Val Ile Phe Asp Arg Leu Glu Thr Leu
130                 135                 140

Ile Leu Leu Arg Ala Phe Thr Glu Glu Gly Ala Ile Val Gly Glu Ile
145                 150                 155                 160

Ser Pro Leu Pro Ser Phe Pro Gly His Thr Ile Glu Asp Val Lys Asn
```

-continued

```
                    165                 170                 175
Ala Ile Gly Val Leu Ile Gly Gly Leu Glu Trp Asn Asp Asn Thr Val
                180                 185                 190

Arg Val Ser Lys Thr Leu Gln Arg Phe Ala Trp Gly Ser Ser Asn Glu
            195                 200                 205

Asn Gly Arg Ala Ala Leu Thr Ala Lys Gln Lys Arg Lys Met Ala Arg
        210                 215                 220

Thr Ala Arg Ser Lys Val Arg Arg Asp Lys Met Ala Asp
225                 230                 235

<210> SEQ ID NO 26
<211> LENGTH: 237
<212> TYPE: PRT
<213> ORGANISM: Artificial
<220> FEATURE:
<223> OTHER INFORMATION: H3N2 Udorn-SH3-motif1/2-mt P164A P167A P212A
      P213A P216A

<400> SEQUENCE: 26

Met Asp Ser Asn Thr Val Ser Ser Phe Gln Val Asp Cys Phe Leu Trp
1               5                   10                  15

His Val Arg Lys Gln Val Val Asp Gln Glu Leu Gly Asp Ala Pro Phe
                20                  25                  30

Leu Asp Arg Leu Arg Arg Asp Gln Lys Ser Leu Arg Gly Arg Gly Ser
            35                  40                  45

Thr Leu Gly Leu Asn Ile Glu Ala Ala Thr His Val Gly Lys Gln Ile
        50                  55                  60

Val Glu Lys Ile Leu Lys Glu Ser Asp Glu Ala Leu Lys Met Thr
65                  70                  75                  80

Met Ala Ser Thr Pro Ala Ser Arg Tyr Ile Thr Asp Met Thr Ile Glu
                85                  90                  95

Glu Leu Ser Arg Asp Trp Phe Met Leu Met Pro Lys Gln Lys Val Glu
            100                 105                 110

Gly Pro Leu Cys Ile Arg Ile Asp Gln Ala Ile Met Asp Lys Asn Ile
        115                 120                 125

Met Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Ala Ser Phe Ala Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Gly Ser Ser Asn Glu
        195                 200                 205

Asn Gly Arg Ala Ala Leu Thr Ala Lys Gln Lys Arg Lys Met Ala Arg
    210                 215                 220

Thr Ala Arg Ser Lys Val Arg Arg Asp Lys Met Ala Asp
225                 230                 235

<210> SEQ ID NO 27
<211> LENGTH: 237
<212> TYPE: PRT
<213> ORGANISM: Artificial
<220> FEATURE:
<223> OTHER INFORMATION: H3N2 Udorn-SH2/SH3-mt Y89F P164A P167A P212A
      P213A P216A
```

<400> SEQUENCE: 27

Met Asp Ser Asn Thr Val Ser Ser Phe Gln Val Asp Cys Phe Leu Trp
1               5                   10                  15

His Val Arg Lys Gln Val Val Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asn Ile Glu Ala Ala Thr His Val Gly Lys Gln Ile
    50                  55                  60

Val Glu Lys Ile Leu Lys Glu Glu Ser Asp Glu Ala Leu Lys Met Thr
65                  70                  75                  80

Met Ala Ser Thr Pro Ala Ser Arg Phe Ile Thr Asp Met Thr Ile Glu
                85                  90                  95

Glu Leu Ser Arg Asp Trp Phe Met Leu Met Pro Lys Gln Lys Val Glu
            100                 105                 110

Gly Pro Leu Cys Ile Arg Ile Asp Gln Ala Ile Met Asp Lys Asn Ile
        115                 120                 125

Met Leu Lys Ala Asn Phe Ser Val Ile Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Ala Ser Phe Ala Gly His Thr Ile Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Gly Ser Ser Asn Glu
        195                 200                 205

Asn Gly Arg Ala Ala Leu Thr Ala Lys Gln Leu Arg Lys Met Ala Arg
    210                 215                 220

Thr Ala Arg Ser Lys Val Arg Arg Asp Lys Met Ala Asp
225                 230                 235

<210> SEQ ID NO 28
<211> LENGTH: 225
<212> TYPE: PRT
<213> ORGANISM: Artificial
<220> FEATURE:
<223> OTHER INFORMATION: H5N1 Thailand-SH2-mt Y84F

<400> SEQUENCE: 28

Met Asp Ser Asn Thr Val Ser Ser Phe Gln Val Asp Cys Phe Leu Trp
1               5                   10                  15

His Val Arg Lys Arg Phe Ala Asp Arg Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Glu Ser Asp Lys Ala Leu Lys Met Pro
65                  70                  75                  80

Ala Ser Arg Phe Leu Thr Asp Met Thr Leu Glu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Val Ile Ile Leu Lys Ala Asn

```
                115                 120                 125
Phe Ser Val Ile Phe Asp Arg Leu Glu Thr Leu Ile Leu Leu Arg Ala
    130                 135                 140
Phe Thr Glu Glu Gly Ala Ile Val Gly Glu Ile Ser Pro Leu Pro Ser
145                 150                 155                 160
Leu Pro Gly His Thr Gly Glu Asp Val Lys Asn Ala Ile Gly Val Leu
                165                 170                 175
Ile Gly Gly Leu Glu Trp Asn Asp Asn Thr Val Gln Val Thr Glu Thr
                180                 185                 190
Leu Gln Arg Phe Ala Trp Arg Ser Ser Asp Glu Asp Gly Arg Leu Pro
                195                 200                 205
Leu Pro Pro Asn Gln Lys Arg Lys Met Ala Arg Thr Ile Glu Ser Glu
    210                 215                 220
Val
225

<210> SEQ ID NO 29
<211> LENGTH: 225
<212> TYPE: PRT
<213> ORGANISM: Artificial
<220> FEATURE:
<223> OTHER INFORMATION: H5N1 Thailand-SH3-motif1-mt P159A P162A

<400> SEQUENCE: 29

Met Asp Ser Asn Thr Val Ser Ser Phe Gln Val Asp Cys Phe Leu Trp
1               5                   10                  15
His Val Arg Lys Arg Phe Ala Asp Arg Glu Leu Gly Asp Ala Pro Phe
                20                  25                  30
Leu Asp Arg Leu Arg Arg Asp Gln Lys Ser Leu Arg Gly Arg Gly Asn
            35                  40                  45
Thr Leu Gly Leu Asp Ile Glu Thr Ala Thr Arg Ala Gly Lys Gln Ile
    50                  55                  60
Val Glu Arg Ile Leu Glu Glu Ser Asp Lys Ala Leu Lys Met Pro
65                  70                  75                  80
Ala Ser Arg Tyr Leu Thr Asp Met Thr Leu Glu Glu Met Ser Arg Asp
                85                  90                  95
Trp Phe Met Leu Met Pro Lys Gln Lys Val Ala Gly Ser Leu Cys Ile
                100                 105                 110
Lys Met Asp Gln Ala Ile Met Asp Lys Val Ile Ile Leu Lys Ala Asn
    115                 120                 125
Phe Ser Val Ile Phe Asp Arg Leu Glu Thr Leu Ile Leu Leu Arg Ala
    130                 135                 140
Phe Thr Glu Glu Gly Ala Ile Val Gly Glu Ile Ser Pro Leu Ala Ser
145                 150                 155                 160
Leu Ala Gly His Thr Gly Glu Asp Val Lys Asn Ala Ile Gly Val Leu
                165                 170                 175
Ile Gly Gly Leu Glu Trp Asn Asp Asn Thr Val Gln Val Thr Glu Thr
                180                 185                 190
Leu Gln Arg Phe Ala Trp Arg Ser Ser Asp Glu Asp Gly Arg Leu Pro
                195                 200                 205
Leu Pro Pro Asn Gln Lys Arg Lys Met Ala Arg Thr Ile Glu Ser Glu
    210                 215                 220
Val
225
```

<210> SEQ ID NO 30
<211> LENGTH: 225
<212> TYPE: PRT
<213> ORGANISM: Artificial
<220> FEATURE:
<223> OTHER INFORMATION: H5N1 Thailand-SH3-motif2-mt L207A P208A P211A

<400> SEQUENCE: 30

```
Met Asp Ser Asn Thr Val Ser Ser Phe Gln Val Asp Cys Phe Leu Trp
1               5                   10                  15

His Val Arg Lys Arg Phe Ala Asp Arg Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Lys Ala Leu Lys Met Pro
65                  70                  75                  80

Ala Ser Arg Tyr Leu Thr Asp Met Thr Leu Glu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Val Ile Ile Leu Lys Ala Asn
        115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Pro Ser
145                 150                 155                 160

Leu Pro Gly His Thr Gly Glu Asp Val Lys Asn Ala Ile Gly Val Leu
                165                 170                 175

Ile Gly Gly Leu Glu Trp Asn Asp Asn Thr Val Gln Val Thr Glu Thr
            180                 185                 190

Leu Gln Arg Phe Ala Trp Arg Ser Ser Asp Glu Asp Gly Arg Ala Ala
        195                 200                 205

Leu Pro Ala Asn Gln Lys Arg Lys Met Ala Arg Thr Ile Glu Ser Glu
    210                 215                 220

Val
225
```

<210> SEQ ID NO 31
<211> LENGTH: 225
<212> TYPE: PRT
<213> ORGANISM: Artificial
<220> FEATURE:
<223> OTHER INFORMATION: H5N1 Thailand-SH3-motif1/2-mt P159A P162A L207A
    P208A P211A

<400> SEQUENCE: 31

```
Met Asp Ser Asn Thr Val Ser Ser Phe Gln Val Asp Cys Phe Leu Trp
1               5                   10                  15

His Val Arg Lys Arg Phe Ala Asp Arg Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Lys Ala Leu Lys Met Pro
65                  70                  75                  80
```

```
Ala Ser Arg Tyr Leu Thr Asp Met Thr Leu Glu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Val Ile Ile Leu Lys Ala Asn
        115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Ala Ser
145                 150                 155                 160

Leu Ala Gly His Thr Gly Glu Asp Val Lys Asn Ala Ile Gly Val Leu
                165                 170                 175

Ile Gly Gly Leu Glu Trp Asn Asp Asn Thr Val Gln Val Thr Glu Thr
            180                 185                 190

Leu Gln Arg Phe Ala Trp Arg Ser Ser Asp Glu Asp Gly Arg Ala Ala
        195                 200                 205

Leu Pro Ala Asn Gln Lys Arg Lys Met Ala Arg Thr Ile Glu Ser Glu
    210                 215                 220

Val
225

<210> SEQ ID NO 32
<211> LENGTH: 225
<212> TYPE: PRT
<213> ORGANISM: Artificial
<220> FEATURE:
<223> OTHER INFORMATION: H5N1 Thailand-SH2/SH3-mt Y84F P159A P162A L207A
      P208A P211A

<400> SEQUENCE: 32

Met Asp Ser Asn Thr Val Ser Ser Phe Gln Val Asp Cys Phe Leu Trp
1               5                   10                  15

His Val Arg Lys Arg Phe Ala Asp Arg Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Lys Ala Leu Lys Met Pro
65                  70                  75                  80

Ala Ser Arg Phe Leu Thr Asp Met Thr Leu Glu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Val Ile Ile Leu Lys Ala Asn
        115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Ala Ser
145                 150                 155                 160

Leu Ala Gly His Thr Gly Glu Asp Val Lys Asn Ala Ile Gly Val Leu
                165                 170                 175

Ile Gly Gly Leu Glu Trp Asn Asp Asn Thr Val Gln Val Thr Glu Thr
            180                 185                 190

Leu Gln Arg Phe Ala Trp Arg Ser Ser Asp Glu Asp Gly Arg Ala Ala
```

```
                        195                 200                 205
Leu Pro Ala Asn Gln Lys Arg Lys Met Ala Arg Thr Ile Glu Ser Glu
    210                 215                 220
Val
225

<210> SEQ ID NO 33
<211> LENGTH: 225
<212> TYPE: PRT
<213> ORGANISM: Artificial
<220> FEATURE:
<223> OTHER INFORMATION: H5N1 Viet Nam-SH2-mt Y84F

<400> SEQUENCE: 33

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Lys Ala Leu Lys Met Pro
65                  70                  75                  80

Ala Ser Arg Phe Leu Thr Asp Met Thr Leu Glu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Thr Ile Ile Leu Lys Ala Asn
        115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Pro Ser
145                 150                 155                 160

Leu Pro Gly His Thr Gly Glu Asp Val Lys Asn Ala Ile Gly Val Leu
                165                 170                 175

Ile Gly Gly Leu Glu Trp Asn Asp Asn Thr Val Arg Val Thr Glu Thr
            180                 185                 190

Ile Gln Arg Phe Ala Trp Arg Asn Ser Asp Glu Asp Gly Arg Leu Pro
        195                 200                 205

Leu Pro Pro Asn Gln Lys Arg Lys Met Ala Arg Thr Ile Glu Ser Glu
    210                 215                 220

Val
225

<210> SEQ ID NO 34
<211> LENGTH: 225
<212> TYPE: PRT
<213> ORGANISM: Artificial
<220> FEATURE:
<223> OTHER INFORMATION: H5N1 Viet Nam-SH3-motif1-mt P159A P162A

<400> SEQUENCE: 34

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30
```

```
Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
 50                  55                  60

Val Glu Arg Ile Leu Glu Glu Ser Asp Lys Ala Leu Lys Met Pro
 65                  70                  75                  80

Ala Ser Arg Tyr Leu Thr Asp Met Thr Leu Glu Glu Met Ser Arg Asp
                 85                  90                  95

Trp Phe Met Leu Met Pro Lys Gln Lys Val Ala Gly Ser Leu Cys Ile
            100                 105                 110

Lys Met Asp Gln Ala Ile Met Asp Lys Thr Ile Ile Leu Lys Ala Asn
            115                 120                 125

Phe Ser Val Ile Phe Asp Arg Leu Glu Thr Leu Ile Leu Leu Arg Ala
            130                 135                 140

Phe Thr Glu Glu Gly Ala Ile Val Gly Glu Ile Ser Pro Leu Ala Ser
145                 150                 155                 160

Leu Ala Gly His Thr Gly Glu Asp Val Lys Asn Ala Ile Gly Val Leu
                165                 170                 175

Ile Gly Gly Leu Glu Trp Asn Asp Asn Thr Val Arg Val Thr Glu Thr
            180                 185                 190

Ile Gln Arg Phe Ala Trp Arg Asn Ser Asp Glu Asp Gly Arg Leu Pro
            195                 200                 205

Leu Pro Pro Asn Gln Lys Arg Lys Met Ala Arg Thr Ile Glu Ser Glu
        210                 215                 220

Val
225

<210> SEQ ID NO 35
<211> LENGTH: 225
<212> TYPE: PRT
<213> ORGANISM: Artificial
<220> FEATURE:
<223> OTHER INFORMATION: H5N1 Viet Nam-SH3-motif2-mt L207A P208A P211A

<400> SEQUENCE: 35

Met Asp Ser Asn Thr Val Ser Ser Phe Gln Val Asp Cys Phe Leu Trp
1               5                  10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
 50                  55                  60

Val Glu Arg Ile Leu Glu Glu Ser Asp Lys Ala Leu Lys Met Pro
 65                  70                  75                  80

Ala Ser Arg Tyr Leu Thr Asp Met Thr Leu Glu Glu Met Ser Arg Asp
                 85                  90                  95

Trp Phe Met Leu Met Pro Lys Gln Lys Val Ala Gly Ser Leu Cys Ile
            100                 105                 110

Lys Met Asp Gln Ala Ile Met Asp Lys Thr Ile Ile Leu Lys Ala Asn
            115                 120                 125

Phe Ser Val Ile Phe Asp Arg Leu Glu Thr Leu Ile Leu Leu Arg Ala
            130                 135                 140

Phe Thr Glu Glu Gly Ala Ile Val Gly Glu Ile Ser Pro Leu Pro Ser
145                 150                 155                 160
```

```
Leu Pro Gly His Thr Gly Glu Asp Val Lys Asn Ala Ile Gly Val Leu
            165                 170                 175

Ile Gly Gly Leu Glu Trp Asn Asp Asn Thr Val Arg Val Thr Glu Thr
            180                 185                 190

Ile Gln Arg Phe Ala Trp Arg Asn Ser Asp Glu Asp Gly Arg Ala Ala
        195                 200                 205

Leu Pro Ala Asn Gln Lys Arg Lys Met Ala Arg Thr Ile Glu Ser Glu
    210                 215                 220

Val
225

<210> SEQ ID NO 36
<211> LENGTH: 225
<212> TYPE: PRT
<213> ORGANISM: Artificial
<220> FEATURE:
<223> OTHER INFORMATION: H5N1 Viet Nam-SH3-motif1/2-mt P159A P162A L207A
      P208A P211A

<400> SEQUENCE: 36

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Lys Ala Leu Lys Met Pro
65                  70                  75                  80

Ala Ser Arg Tyr Leu Thr Asp Met Thr Leu Glu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Thr Ile Ile Leu Lys Ala Asn
        115                 120                 125

Phe Ser Val Ile Phe Asp Arg Leu Glu Thr Leu Ile Leu Leu Arg Ala
    130                 135                 140

Phe Thr Glu Glu Gly Ala Ile Val Gly Glu Ile Ser Pro Leu Ala Ser
145                 150                 155                 160

Leu Ala Gly His Thr Gly Glu Asp Val Lys Asn Ala Ile Gly Val Leu
            165                 170                 175

Ile Gly Gly Leu Glu Trp Asn Asp Asn Thr Val Arg Val Thr Glu Thr
            180                 185                 190

Ile Gln Arg Phe Ala Trp Arg Asn Ser Asp Glu Asp Gly Arg Ala Ala
        195                 200                 205

Leu Pro Ala Asn Gln Lys Arg Lys Met Ala Arg Thr Ile Glu Ser Glu
    210                 215                 220

Val
225

<210> SEQ ID NO 37
<211> LENGTH: 225
<212> TYPE: PRT
<213> ORGANISM: Artificial
<220> FEATURE:
<223> OTHER INFORMATION: H5N1 Viet Nam-SH2/SH3-mt Y84F P159A P162A L207A
      P208A P211A
```

<400> SEQUENCE: 37

```
Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Asn
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Lys Ala Leu Lys Met Pro
65                  70                  75                  80

Ala Ser Arg Phe Leu Thr Asp Met Thr Leu Glu Glu Met Ser Arg Asp
                85                  90                  95

Trp Phe Met Leu Met Pro Lys Gln Lys Val Ala Gly Ser Leu Cys Ile
            100                 105                 110

Lys Met Asp Gln Ala Ile Met Asp Lys Thr Ile Ile Leu Lys Ala Asn
            115                 120                 125

Phe Ser Val Ile Phe Asp Arg Leu Glu Thr Leu Ile Leu Leu Arg Ala
        130                 135                 140

Phe Thr Glu Glu Gly Ala Ile Val Gly Glu Ile Ser Pro Leu Ala Ser
145                 150                 155                 160

Leu Ala Gly His Thr Gly Glu Asp Val Lys Asn Ala Ile Gly Val Leu
                165                 170                 175

Ile Gly Gly Leu Glu Trp Asn Asp Asn Thr Val Arg Val Thr Glu Thr
            180                 185                 190

Ile Gln Arg Phe Ala Trp Arg Asn Ser Asp Glu Asp Gly Arg Ala Ala
        195                 200                 205

Leu Pro Ala Asn Gln Lys Arg Lys Met Ala Arg Thr Ile Glu Ser Glu
    210                 215                 220

Val
225
```

<210> SEQ ID NO 38
<211> LENGTH: 230
<212> TYPE: PRT
<213> ORGANISM: Artificial
<220> FEATURE:
<223> OTHER INFORMATION: H5N1 Hong Kong-SH2-mt Y89F

<400> SEQUENCE: 38

```
Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Ser Asp Glu Ala Leu Lys Met Thr
65                  70                  75                  80

Ile Ala Ser Val Pro Ala Pro Arg Phe Leu Thr Glu Met Thr Leu Glu
                85                  90                  95

Glu Met Ser Arg Asp Trp Leu Met Leu Ile Pro Lys Gln Lys Val Thr
            100                 105                 110
```

```
Gly Ser Leu Cys Ile Arg Met Asp Gln Ala Ile Met Asp Lys Asp Ile
            115                 120                 125

Ile Leu Lys Ala Asn Phe Ser Val Ile Phe Asn Arg Leu Glu Ala Leu
130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Glu Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Ser Pro Leu Pro Pro Lys Gln Lys Arg Lys Met Glu Arg
    210                 215                 220

Thr Ile Glu Pro Glu Val
225                 230

<210> SEQ ID NO 39
<211> LENGTH: 230
<212> TYPE: PRT
<213> ORGANISM: Artificial
<220> FEATURE:
<223> OTHER INFORMATION: H5N1 Hong Kong-SH3-motif1-mt P164A P167A

<400> SEQUENCE: 39

Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Ser Asp Glu Ala Leu Lys Met Thr
65                  70                  75                  80

Ile Ala Ser Val Pro Ala Pro Arg Tyr Leu Thr Glu Met Thr Leu Glu
                85                  90                  95

Glu Met Ser Arg Asp Trp Leu Met Leu Ile Pro Lys Gln Lys Val Thr
            100                 105                 110

Gly Ser Leu Cys Ile Arg Met Asp Gln Ala Ile Met Asp Lys Asp Ile
        115                 120                 125

Ile Leu Lys Ala Asn Phe Ser Val Ile Phe Asn Arg Leu Glu Ala Leu
130                 135                 140

Ile Leu Leu Arg Ala Phe Thr Asp Glu Gly Ala Ile Val Gly Glu Ile
145                 150                 155                 160

Ser Pro Leu Ala Ser Leu Ala Gly His Thr Glu Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Ser Pro Leu Pro Pro Lys Gln Lys Arg Lys Met Glu Arg
    210                 215                 220

Thr Ile Glu Pro Glu Val
225                 230
```

-continued

```
<210> SEQ ID NO 40
<211> LENGTH: 230
<212> TYPE: PRT
<213> ORGANISM: Artificial
<220> FEATURE:
<223> OTHER INFORMATION: H5N1 Hong Kong-SH3-motif2-mt S212A P213A P216A

<400> SEQUENCE: 40

Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Glu Ser Asp Glu Ala Leu Lys Met Thr
65                  70                  75                  80

Ile Ala Ser Val Pro Ala Pro Arg Tyr Leu Thr Glu Met Thr Leu Glu
                85                  90                  95

Glu Met Ser Arg Asp Trp Leu Met Leu Ile Pro Lys Gln Lys Val Thr
            100                 105                 110

Gly Ser Leu Cys Ile Arg Met Asp Gln Ala Ile Met Asp Lys Asp Ile
        115                 120                 125

Ile Leu Lys Ala Asn Phe Ser Val Ile Phe Asn Arg Leu Glu Ala Leu
    130                 135                 140

Ile Leu Leu Arg Ala Phe Thr Asp Glu Gly Ala Ile Val Gly Glu Ile
145                 150                 155                 160

Ser Pro Leu Pro Ser Leu Pro Gly His Thr Glu Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Ala Ala Leu Pro Ala Lys Gln Lys Arg Lys Met Glu Arg
    210                 215                 220

Thr Ile Glu Pro Glu Val
225                 230

<210> SEQ ID NO 41
<211> LENGTH: 230
<212> TYPE: PRT
<213> ORGANISM: Artificial
<220> FEATURE:
<223> OTHER INFORMATION: H5N1 Hong Kong-SH3-motif1/2-mt P164A P167A
    S212A P213A P216A

<400> SEQUENCE: 41

Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Glu Ser Asp Glu Ala Leu Lys Met Thr
```

-continued

```
            65                  70                  75                  80
Ile Ala Ser Val Pro Ala Pro Arg Tyr Leu Thr Glu Met Thr Leu Glu
                    85                  90                  95

Glu Met Ser Arg Asp Trp Leu Met Leu Ile Pro Lys Gln Lys Val Thr
                100                 105                 110

Gly Ser Leu Cys Ile Arg Met Asp Gln Ala Ile Met Asp Lys Asp Ile
            115                 120                 125

Ile Leu Lys Ala Asn Phe Ser Val Ile Phe Asn Arg Leu Glu Ala Leu
        130                 135                 140

Ile Leu Leu Arg Ala Phe Thr Asp Glu Gly Ala Ile Val Gly Glu Ile
145                 150                 155                 160

Ser Pro Leu Ala Ser Leu Ala Gly His Thr Glu Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Thr Trp Arg Ser Ser Asp Glu
        195                 200                 205

Asn Gly Arg Ala Ala Leu Pro Ala Lys Gln Lys Arg Lys Met Glu Arg
    210                 215                 220

Thr Ile Glu Pro Glu Val
225                 230

<210> SEQ ID NO 42
<211> LENGTH: 230
<212> TYPE: PRT
<213> ORGANISM: Artificial
<220> FEATURE:
<223> OTHER INFORMATION: H5N1 Hong Kong-SH2/SH3-mt Y89F P164A P167A
      S212A P213A P215A

<400> SEQUENCE: 42

Met Asp Ser Asn Thr Val Ser Ser Phe Gln Val Asp Cys Phe Leu Trp
1               5                   10                  15

Arg Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Arg Thr Ala Thr Arg Glu Gly Lys His Ile
    50                  55                  60

Val Glu Arg Ile Leu Glu Glu Glu Ser Asp Glu Ala Leu Lys Met Thr
65                  70                  75                  80

Ile Ala Ser Val Pro Ala Pro Arg Phe Leu Thr Glu Met Thr Leu Glu
                    85                  90                  95

Glu Met Ser Arg Asp Trp Leu Met Leu Ile Pro Lys Gln Lys Val Thr
                100                 105                 110

Gly Ser Leu Cys Ile Arg Met Asp Gln Ala Ile Met Asp Lys Asp Ile
            115                 120                 125

Ile Leu Lys Ala Asn Phe Ser Val Ile Phe Asn Arg Leu Glu Ala Leu
        130                 135                 140

Ile Leu Leu Arg Ala Phe Thr Asp Glu Gly Ala Ile Val Gly Glu Ile
145                 150                 155                 160

Ser Pro Leu Ala Ser Leu Ala Gly His Thr Glu Glu Asp Val Lys Asn
                165                 170                 175

Ala Ile Gly Val Leu Ile Gly Gly Leu Glu Trp Asn Asp Asn Thr Val
            180                 185                 190
```

Arg Val Ser Glu Thr Leu Gln Arg Phe Thr Trp Arg Ser Ser Asp Glu
        195                 200                 205

Asn Gly Arg Ala Ala Leu Pro Ala Lys Gln Lys Arg Lys Met Glu Arg
210                 215                 220

Thr Ile Glu Pro Glu Val
225                 230

<210> SEQ ID NO 43
<211> LENGTH: 230
<212> TYPE: PRT
<213> ORGANISM: Artificial
<220> FEATURE:
<223> OTHER INFORMATION: H7N7 Netherlands-SH2-mt Y89F

<400> SEQUENCE: 43

Met Asp Ser Asn Thr Val Ser Ser Phe Gln Val Asp Cys Phe Leu Trp
1 5 10 15

His Val Arg Lys Arg Phe Ala Asp Gln Glu Leu Gly Asp Ala Pro Phe
20 25 30

Leu Asp Arg Leu Arg Arg Asp Gln Lys Ser Leu Arg Gly Arg Gly Ser
35 40 45

Thr Leu Gly Leu Asp Ile Glu Thr Ala Thr Arg Ala Gly Lys Gln Ile
50 55 60

Val Glu Arg Ile Leu Glu Glu Glu Ser Asp Glu Ala Leu Lys Met Thr
65 70 75 80

Ile Ala Ser Val Leu Ala Ser Arg Phe Leu Thr Asp Met Thr Leu Glu
85 90 95

Glu Met Ser Arg Asp Trp Phe Met Leu Met Pro Lys Gln Lys Val Ala
100 105 110

Gly Ser Leu Cys Ile Arg Met Asp Gln Ala Ile Met Asp Arg Asn Ile
115 120 125

Ile Leu Lys Ala Asn Phe Ser Val Val Phe Asp Arg Leu Glu Thr Leu
130 135 140

Ile Leu Leu Arg Ala Phe Thr Glu Glu Gly Ala Ile Val Gly Glu Ile
145 150 155 160

Ser Pro Leu Pro Ser Leu Pro Gly His Thr Asp Glu Asp Val Lys Asn
165 170 175

Ala Ile Gly Val Leu Ile Gly Gly Leu Glu Trp Asn Asp Asn Thr Val
180 185 190

Arg Val Ser Glu Thr Leu Gln Arg Phe Ala Trp Arg Ser Ser Asn Glu
195 200 205

Asp Gly Arg Pro Pro Leu Pro Pro Lys Gln Lys Arg Lys Met Ala Arg
210 215 220

Thr Ile Glu Ser Glu Val
225 230

<210> SEQ ID NO 44
<211> LENGTH: 230
<212> TYPE: PRT
<213> ORGANISM: Artificial
<220> FEATURE:
<223> OTHER INFORMATION: H7N7 Netherlands-SH3-motif1-mt P164A P167A

<400> SEQUENCE: 44

Met Asp Ser Asn Thr Val Ser Ser Phe Gln Val Asp Cys Phe Leu Trp
1 5 10 15

His Val Arg Lys Arg Phe Ala Asp Gln Glu Leu Gly Asp Ala Pro Phe
20 25 30

```
Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Glu Ala Leu Lys Met Thr
65                  70                  75                  80

Ile Ala Ser Val Leu Ala Ser Arg Tyr Leu Thr Asp Met Thr Leu Glu
                85                  90                  95

Glu Met Ser Arg Asp Trp Phe Met Leu Met Pro Lys Gln Lys Val Ala
            100                 105                 110

Gly Ser Leu Cys Ile Arg Met Asp Gln Ala Ile Met Asp Arg Asn Ile
        115                 120                 125

Ile Leu Lys Ala Asn Phe Ser Val Val Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Ala Ser Leu Ala Gly His Thr Asp Glu Asp Val Lys Asn
                165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
        195                 200                 205

Asp Gly Arg Pro Pro Leu Pro Pro Lys Gln Lys Arg Lys Met Ala Arg
    210                 215                 220

Thr Ile Glu Ser Glu Val
225                 230

<210> SEQ ID NO 45
<211> LENGTH: 230
<212> TYPE: PRT
<213> ORGANISM: Artificial
<220> FEATURE:
<223> OTHER INFORMATION: H7N7 Netherlands-SH3-motif2-mt P212A P213A
      P216A

<400> SEQUENCE: 45

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Glu Ala Leu Lys Met Thr
65                  70                  75                  80

Ile Ala Ser Val Leu Ala Ser Arg Tyr Leu Thr Asp Met Thr Leu Glu
                85                  90                  95

Glu Met Ser Arg Asp Trp Phe Met Leu Met Pro Lys Gln Lys Val Ala
            100                 105                 110

Gly Ser Leu Cys Ile Arg Met Asp Gln Ala Ile Met Asp Arg Asn Ile
        115                 120                 125

Ile Leu Lys Ala Asn Phe Ser Val Val Phe Asp Arg Leu Glu Thr Leu
    130                 135                 140

Ile Leu Leu Arg Ala Phe Thr Glu Glu Gly Ala Ile Val Gly Glu Ile
```

```
                145                 150                 155                 160
Ser Pro Leu Pro Ser Leu Pro Gly His Thr Asp Glu Asp Val Lys Asn
            165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
            195                 200                 205

Asp Gly Arg Ala Ala Leu Pro Ala Lys Gln Lys Arg Lys Met Ala Arg
            210                 215                 220

Thr Ile Glu Ser Glu Val
225                 230

<210> SEQ ID NO 46
<211> LENGTH: 230
<212> TYPE: PRT
<213> ORGANISM: Artificial
<220> FEATURE:
<223> OTHER INFORMATION: H7N7 Netherlands-SH3-motif1/2-mt P164A P167A
      P212A P213A P216A

<400> SEQUENCE: 46

Met Asp Ser Asn Thr Val Ser Ser Phe Gln Val Asp Cys Phe Leu Trp
1               5                   10                  15

His Val Arg Lys Arg Phe Ala Asp Gln Glu Leu Gly Asp Ala Pro Phe
            20                  25                  30

Leu Asp Arg Leu Arg Arg Asp Gln Lys Ser Leu Arg Gly Arg Gly Ser
        35                  40                  45

Thr Leu Gly Leu Asp Ile Glu Thr Ala Thr Arg Ala Gly Lys Gln Ile
    50                  55                  60

Val Glu Arg Ile Leu Glu Glu Ser Asp Glu Ala Leu Lys Met Thr
65                  70                  75                  80

Ile Ala Ser Val Leu Ala Ser Arg Tyr Leu Thr Asp Met Thr Leu Glu
                85                  90                  95

Glu Met Ser Arg Asp Trp Phe Met Leu Met Pro Lys Gln Lys Val Ala
            100                 105                 110

Gly Ser Leu Cys Ile Arg Met Asp Gln Ala Ile Met Asp Arg Asn Ile
        115                 120                 125

Ile Leu Lys Ala Asn Phe Ser Val Val Phe Asp Arg Leu Glu Thr Leu
    130                 135                 140

Ile Leu Leu Arg Ala Phe Thr Glu Glu Gly Ala Ile Val Gly Glu Ile
145                 150                 155                 160

Ser Pro Leu Ala Ser Leu Ala Gly His Thr Asp Glu Asp Val Lys Asn
            165                 170                 175

Ala Ile Gly Val Leu Ile Gly Gly Leu Glu Trp Asn Asp Asn Thr Val
            180                 185                 190

Arg Val Ser Glu Thr Leu Gln Arg Phe Ala Trp Arg Ser Ser Asn Glu
            195                 200                 205

Asp Gly Arg Ala Ala Leu Pro Ala Lys Gln Lys Arg Lys Met Ala Arg
            210                 215                 220

Thr Ile Glu Ser Glu Val
225                 230

<210> SEQ ID NO 47
<211> LENGTH: 230
<212> TYPE: PRT
<213> ORGANISM: Artificial
<220> FEATURE:
```

<223> OTHER INFORMATION: H7N7 Netherlands-SH2/SH3-mt Y89F P164A P167A
    P212A P213

```
<220> FEATURE:
<223> OTHER INFORMATION: primer

<400> SEQUENCE: 50
ggcctctgta cctgcgtcta gatttctaac tgacatgact c                              41

<210> SEQ ID NO 51
<211> LENGTH: 41
<212> TYPE: DNA
<213> ORGANISM: Artificial
<220> FEATURE:
<223> OTHER INFORMATION: primer

<400> SEQUENCE: 51
gagtcatgtc agttagaaat ctagacgcag gtacagaggc c                              41

<210> SEQ ID NO 52
<211> LENGTH: 40
<212> TYPE: DNA
<213> ORGANISM: Artificial
<220> FEATURE:
<223> OTHER INFORMATION: primer

<400> SEQUENCE: 52
atgagaatgg gagatctgca ctcactgcaa aacagaaacg                                40

<210> SEQ ID NO 53
<211> LENGTH: 40
<212> TYPE: DNA
<213> ORGANISM: Artificial
<220> FEATURE:
<223> OTHER INFORMATION: primer

<400> SEQUENCE: 53
cgtttctgtt ttgcagtgag tgcagatctc ccattctcat                                40

<210> SEQ ID NO 54
<211> LENGTH: 48
<212> TYPE: DNA
<213> ORGANISM: Artificial
<220> FEATURE:
<223> OTHER INFORMATION: primer

<400> SEQUENCE: 54
aattgttggc gaaatttctg cattggcttc tcttgcagga catactgc                       48

<210> SEQ ID NO 55
<211> LENGTH: 47
<212> TYPE: DNA
<213> ORGANISM: Artificial
<220> FEATURE:
<223> OTHER INFORMATION: primer

<400> SEQUENCE: 55
tcagcagtat gtcctgcaag agaagccaat gcagaaattt cgccaac                        47

<210> SEQ ID NO 56
<211> LENGTH: 31
<212> TYPE: DNA
<213> ORGANISM: Artificial
<220> FEATURE:
<223> OTHER INFORMATION: primer

<400> SEQUENCE: 56
acgtgctagc atggatccaa acactgtgtc a                                         31
```

```
<210> SEQ ID NO 57
<211> LENGTH: 31
<212> TYPE: DNA
<213> ORGANISM: Artificial
<220> FEATURE:
<223> OTHER INFORMATION: primer

<400> SEQUENCE: 57
ctgactcgag ctaaataagc tgaaacgaga a                              31
```